US008672885B2

(12) United States Patent
Kriesel et al.

(10) Patent No.: US 8,672,885 B2
(45) Date of Patent: *Mar. 18, 2014

(54) FLUID DISPENSING DEVICE

(76) Inventors: Marshall S. Kriesel, St. Paul, MN (US);
Joshua W. Kriesel, San Francisco, CA (US)

(*) Notice: Subject to any disclaimer, the term of this patent is extended or adjusted under 35 U.S.C. 154(b) by 15 days.

This patent is subject to a terminal disclaimer.

(21) Appl. No.: 12/925,980

(22) Filed: Nov. 3, 2010

(65) Prior Publication Data

US 2011/0092904 A1    Apr. 21, 2011

Related U.S. Application Data

(62) Division of application No. 11/725,222, filed on Mar. 14, 2007, now Pat. No. 7,828,772.

(60) Provisional application No. 60/783,182, filed on Mar. 15, 2006.

(51) Int. Cl.
| | | |
|---|---|---|
| A61M 5/20 | (2006.01) | |
| A61M 37/00 | (2006.01) | |
| A61M 5/00 | (2006.01) | |
| A61M 5/14 | (2006.01) | |
| A61K 9/22 | (2006.01) | |

(52) U.S. Cl.
USPC ........... 604/134; 604/131; 604/246; 604/247; 604/256; 604/890.1

(58) Field of Classification Search
USPC ......... 604/131, 134–136, 151, 153, 207, 211, 604/246–248, 256, 260, 890.1, 891.1
See application file for complete search history.

(56) References Cited

U.S. PATENT DOCUMENTS

| | | | | |
|---|---|---|---|---|
| RE27,155 E | * | 7/1971 | Hansen | 425/524 |
| 3,731,681 A | * | 5/1973 | Blackshear et al. | 604/141 |
| 3,884,228 A | * | 5/1975 | Hahn | 604/131 |
| 4,381,006 A | * | 4/1983 | Genese | 604/135 |
| 4,525,165 A | * | 6/1985 | Fischell | 604/131 |
| 4,557,728 A | * | 12/1985 | Sealfon et al. | 604/134 |
| 4,608,042 A | * | 8/1986 | Vanderveen et al. | 604/81 |
| 4,681,566 A | * | 7/1987 | Fenton et al. | 604/135 |
| 4,755,172 A | * | 7/1988 | Baldwin | 604/131 |
| 4,772,263 A | * | 9/1988 | Dorman et al. | 604/132 |
| 4,850,807 A | * | 7/1989 | Frantz | 417/63 |
| 4,863,429 A | * | 9/1989 | Baldwin | 604/135 |
| 5,007,556 A | * | 4/1991 | Lover | 222/386.5 |
| 5,014,750 A | * | 5/1991 | Winchell et al. | 138/43 |
| 5,098,377 A | * | 3/1992 | Borsanyi et al. | 604/30 |
| 5,100,389 A | * | 3/1992 | Vaillancourt | 604/135 |
| 5,176,641 A | * | 1/1993 | Idriss | 604/133 |
| 5,205,820 A | * | 4/1993 | Kriesel | 604/85 |
| 5,226,551 A | * | 7/1993 | Robbins, III | 220/8 |
| 5,236,418 A | * | 8/1993 | Kriesel | 604/85 |
| 5,290,259 A | * | 3/1994 | Fischer | 604/218 |
| 5,306,257 A | * | 4/1994 | Zdeb | 604/131 |

(Continued)

*Primary Examiner* — Victoria P Shumate
(74) *Attorney, Agent, or Firm* — James E. Brunton

(57) ABSTRACT

A compact fluid dispenser for use in controllably dispensing fluid medicaments, such as antibiotics, blood clotting agents, analgesics, and like medicinal agents from collapsible containers at a uniform rate. The dispenser includes a novel stored energy source that is provided in the form of a compressible-expandable member that functions to continuously and uniformly expel fluid from the device reservoir. The apparatus further includes a novel fluid flow control assembly that precisely controls the flow of the medicament solutions from the device reservoir to the patient.

5 Claims, 68 Drawing Sheets

(56) References Cited

U.S. PATENT DOCUMENTS

| | | | |
|---|---|---|---|
| 5,314,405 A * | 5/1994 | Kriesel et al. | 604/8 |
| 5,333,761 A * | 8/1994 | Davis et al. | 222/212 |
| 5,336,188 A * | 8/1994 | Kriesel | 604/132 |
| 5,346,476 A * | 9/1994 | Elson | 604/135 |
| 5,380,287 A * | 1/1995 | Kikuchi et al. | 604/135 |
| 5,411,480 A * | 5/1995 | Kriesel | 604/133 |
| 5,419,771 A * | 5/1995 | Kriesel | 604/132 |
| 5,484,410 A * | 1/1996 | Kriesel et al. | 604/89 |
| 5,499,968 A * | 3/1996 | Milijasevic et al. | 604/30 |
| 5,509,906 A * | 4/1996 | Poynter | 604/212 |
| 5,514,090 A * | 5/1996 | Kriesel et al. | 604/85 |
| 5,545,139 A * | 8/1996 | Kriesel | 604/132 |
| 5,573,129 A * | 11/1996 | Nagata et al. | 215/382 |
| 5,620,420 A * | 4/1997 | Kriesel | 604/133 |
| 5,632,315 A * | 5/1997 | Rose | 141/329 |
| 5,632,406 A * | 5/1997 | Robbins, III | 220/666 |
| 5,693,018 A * | 12/1997 | Kriesel et al. | 604/132 |
| 5,693,019 A * | 12/1997 | Kriesel | 604/132 |
| 5,720,729 A * | 2/1998 | Kriesel | 604/132 |
| 5,721,382 A * | 2/1998 | Kriesel et al. | 73/861.47 |
| 5,735,818 A * | 4/1998 | Kriesel et al. | 604/132 |
| 5,741,242 A * | 4/1998 | Kriesel | 604/403 |
| 5,743,879 A * | 4/1998 | Kriesel | 604/132 |
| 5,766,149 A * | 6/1998 | Kriesel et al. | 604/89 |
| 5,779,676 A * | 7/1998 | Kriesel et al. | 604/132 |
| 5,807,323 A * | 9/1998 | Kriesel et al. | 604/89 |
| 5,836,484 A * | 11/1998 | Gerber | 222/494 |
| 5,858,005 A * | 1/1999 | Kriesel | 604/180 |
| 5,885,250 A * | 3/1999 | Kriesel et al. | 604/132 |
| 5,897,530 A * | 4/1999 | Jackson | 604/132 |
| 5,921,962 A * | 7/1999 | Kriesel et al. | 604/132 |
| 5,925,017 A * | 7/1999 | Kriesel et al. | 604/132 |
| 5,957,891 A * | 9/1999 | Kriesel et al. | 604/132 |
| 5,993,425 A * | 11/1999 | Kriesel | 604/191 |
| 6,010,482 A * | 1/2000 | Kriesel et al. | 604/131 |
| 6,027,472 A * | 2/2000 | Kriesel et al. | 604/89 |
| 6,030,363 A * | 2/2000 | Kriesel | 604/132 |
| 6,045,533 A * | 4/2000 | Kriesel et al. | 604/132 |
| 6,050,400 A * | 4/2000 | Taskis et al. | 206/204 |
| 6,063,059 A * | 5/2000 | Kriesel | 604/133 |
| 6,068,613 A * | 5/2000 | Kriesel et al. | 604/132 |
| 6,068,614 A * | 5/2000 | Kimber et al. | 604/200 |
| 6,086,561 A * | 7/2000 | Kriesel et al. | 604/133 |
| 6,090,071 A * | 7/2000 | Kriesel | 604/131 |
| 6,095,491 A * | 8/2000 | Kriesel | 251/206 |
| 6,126,637 A * | 10/2000 | Kriesel et al. | 604/132 |
| 6,126,642 A * | 10/2000 | Kriesel et al. | 604/207 |
| 6,152,898 A * | 11/2000 | Olsen | 604/93.01 |
| 6,159,180 A * | 12/2000 | Kriesel et al. | 604/132 |
| 6,176,845 B1 * | 1/2001 | Kriesel et al. | 604/132 |
| 6,183,441 B1 * | 2/2001 | Kriesel et al. | 604/132 |
| 6,190,359 B1 * | 2/2001 | Heruth | 604/131 |
| 6,210,368 B1 * | 4/2001 | Rogers | 604/131 |
| 6,236,624 B1 * | 5/2001 | Kriesel et al. | 368/65 |
| 6,245,041 B1 * | 6/2001 | Kriesel | 604/131 |
| 6,258,062 B1 * | 7/2001 | Thielen et al. | 604/141 |
| 6,270,481 B1 * | 8/2001 | Mason et al. | 604/181 |
| 6,273,133 B1 * | 8/2001 | Williamson et al. | 137/625.32 |
| 6,277,095 B1 * | 8/2001 | Kriesel et al. | 604/132 |
| 6,293,159 B1 * | 9/2001 | Kriesel et al. | 73/861.47 |
| 6,319,235 B1 * | 11/2001 | Yoshino | 604/216 |
| 6,355,019 B1 * | 3/2002 | Kriesel et al. | 604/132 |
| 6,391,006 B1 * | 5/2002 | Kriesel et al. | 604/132 |
| 6,394,980 B2 * | 5/2002 | Kriesell et al. | 604/132 |
| 6,398,760 B1 * | 6/2002 | Danby | 604/132 |
| 6,416,495 B1 * | 7/2002 | Kriesel et al. | 604/132 |
| 6,485,461 B1 * | 11/2002 | Mason et al. | 604/132 |
| 6,537,249 B2 * | 3/2003 | Kriesell et al. | 604/131 |
| 6,542,350 B1 * | 4/2003 | Rogers | 361/284 |
| 6,569,125 B2 * | 5/2003 | Jepson et al. | 604/201 |
| 6,645,175 B2 * | 11/2003 | Kriesel et al. | 604/132 |
| 6,669,668 B1 * | 12/2003 | Kleeman et al. | 604/131 |
| 6,679,304 B1 * | 1/2004 | Vacca | 141/313 |
| 7,029,455 B2 * | 4/2006 | Flaherty | 604/131 |
| 7,108,151 B2 * | 9/2006 | Higuchi | 220/666 |
| 2001/0054627 A1 * | 12/2001 | Lin et al. | 222/386.5 |
| 2005/0038387 A1 * | 2/2005 | Kriesel et al. | 604/133 |
| 2006/0030819 A1 * | 2/2006 | Young et al. | 604/187 |

\* cited by examiner

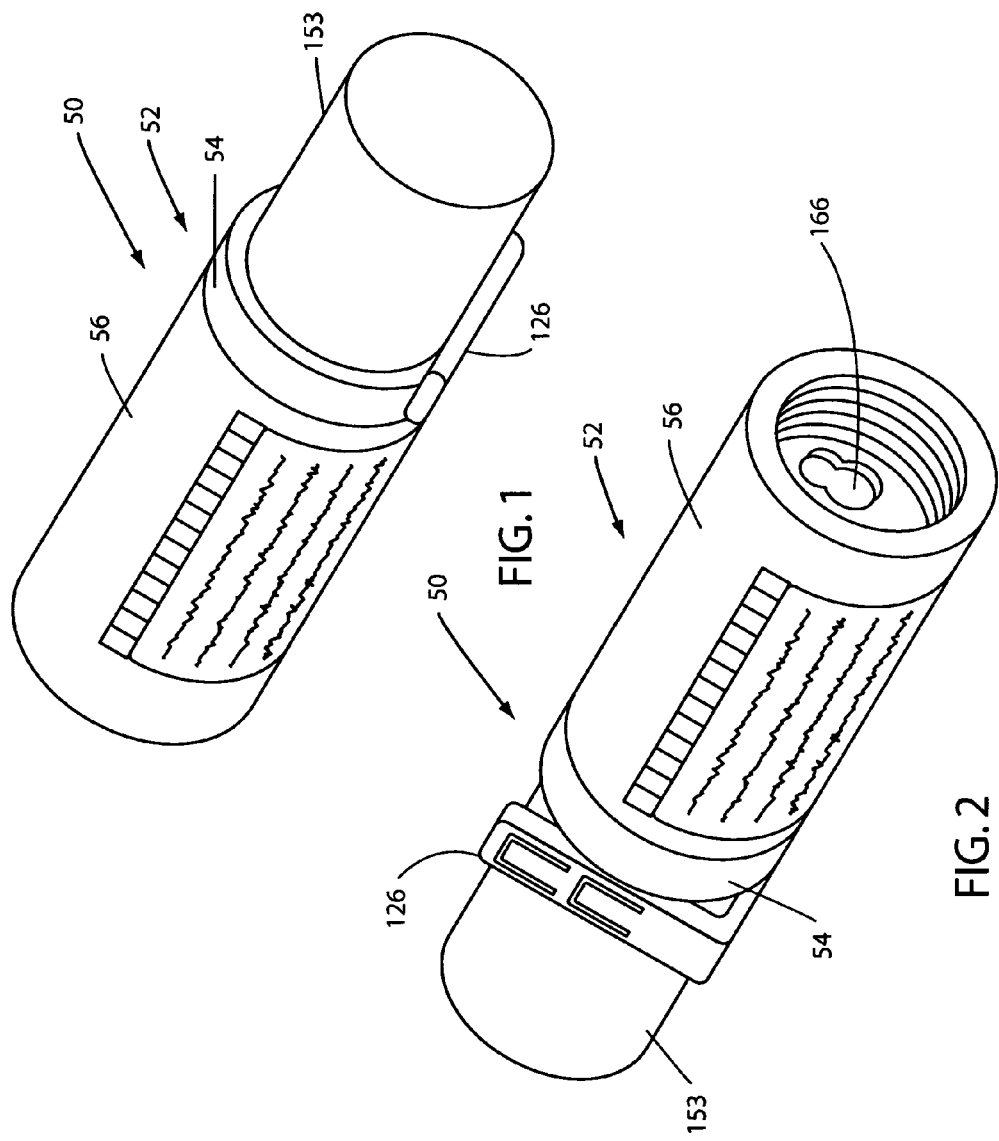

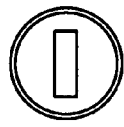
FIG. 14
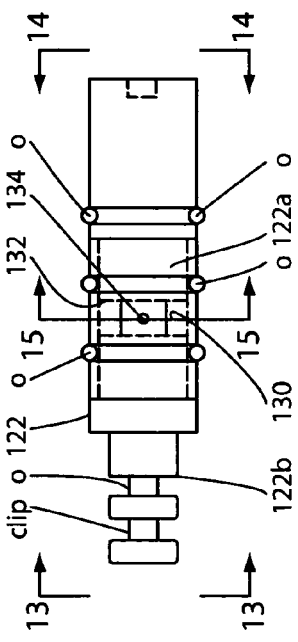
FIG. 12
FIG. 13
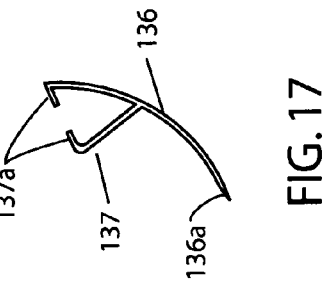
FIG. 17
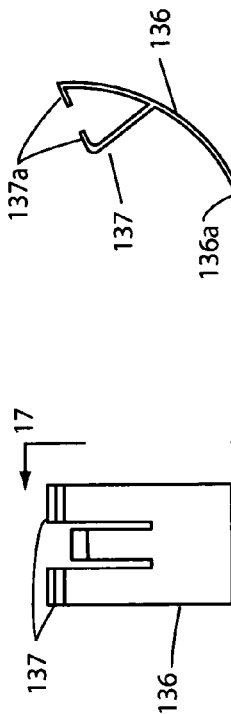
FIG. 16
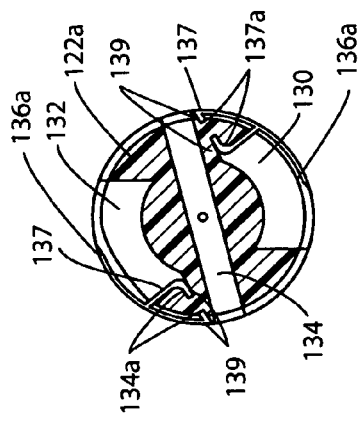
FIG. 15

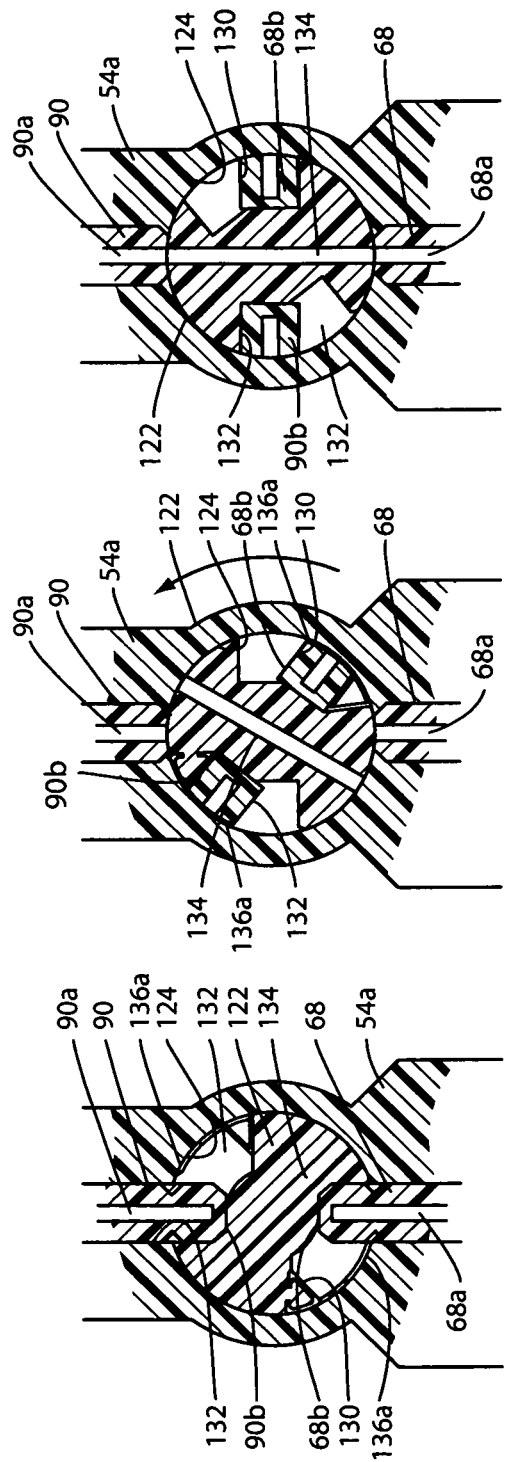

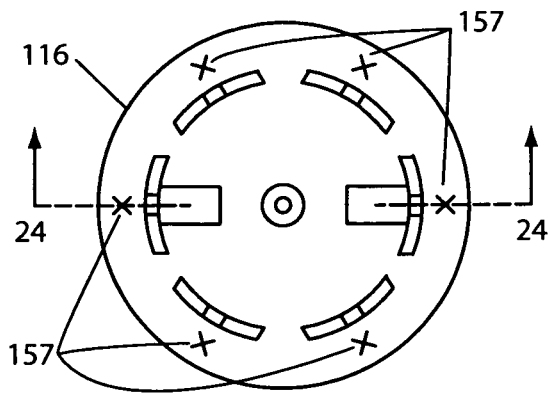
FIG. 23
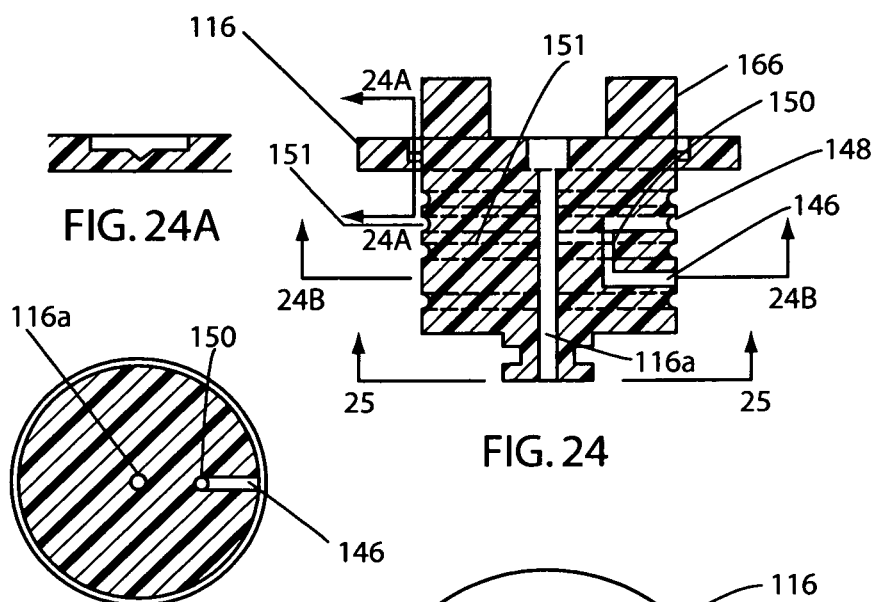
FIG. 24A
FIG. 24B
FIG. 24
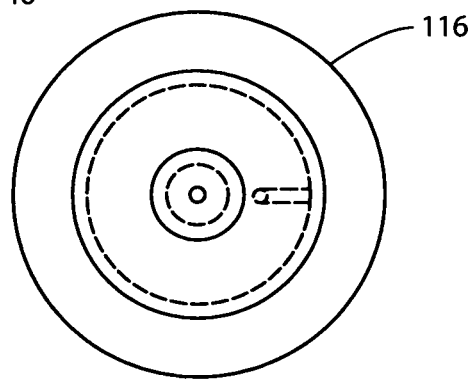
FIG. 25

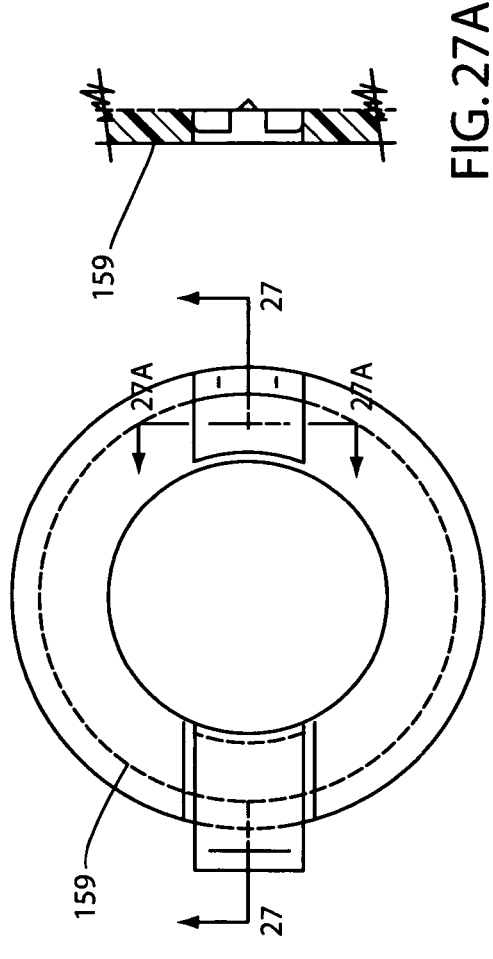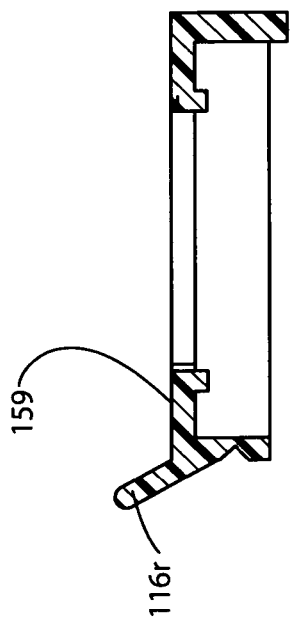
FIG. 27A
FIG. 26
FIG. 27

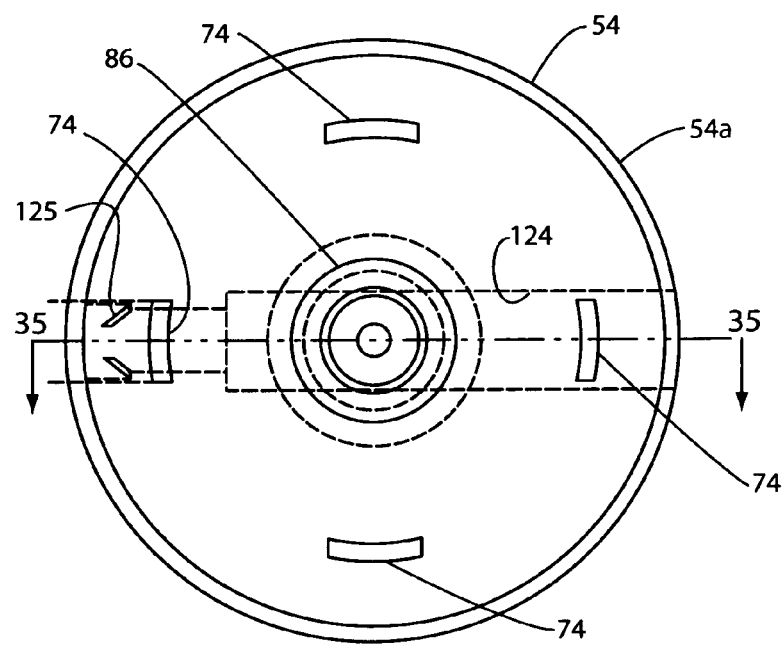
FIG. 34
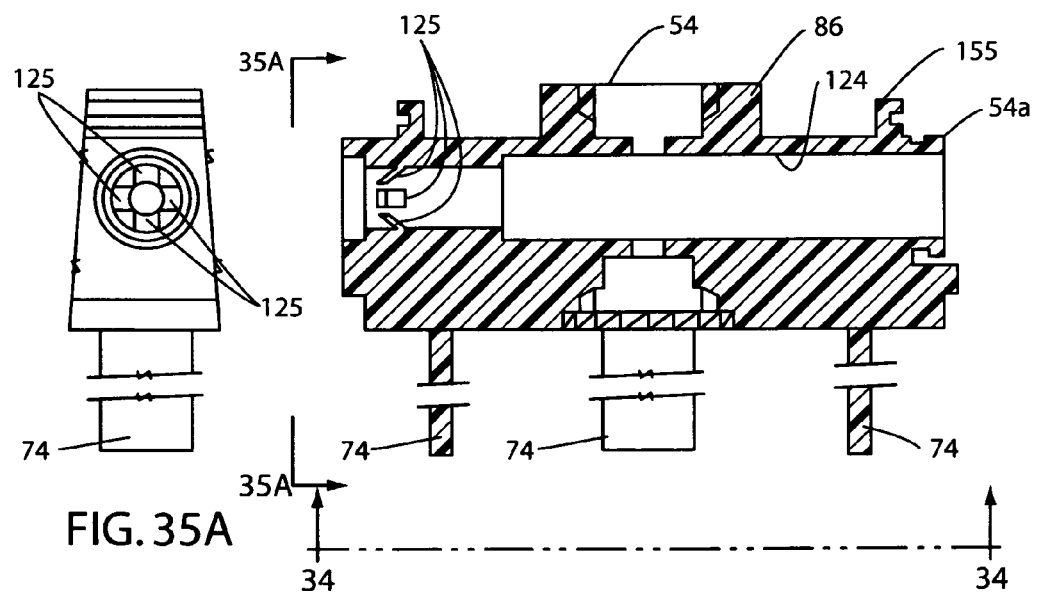
FIG. 35A
FIG. 35

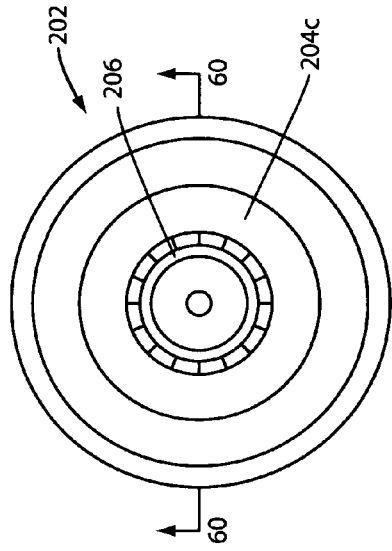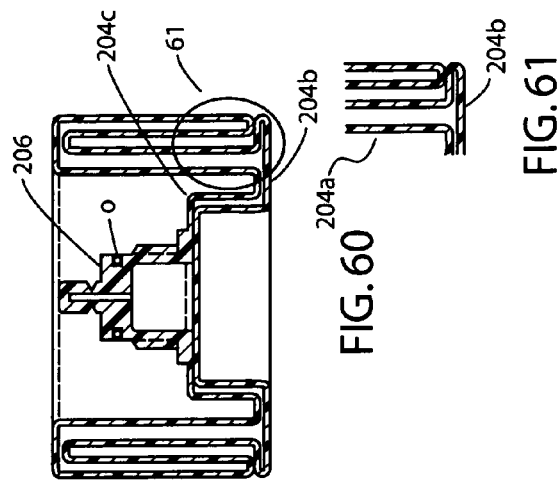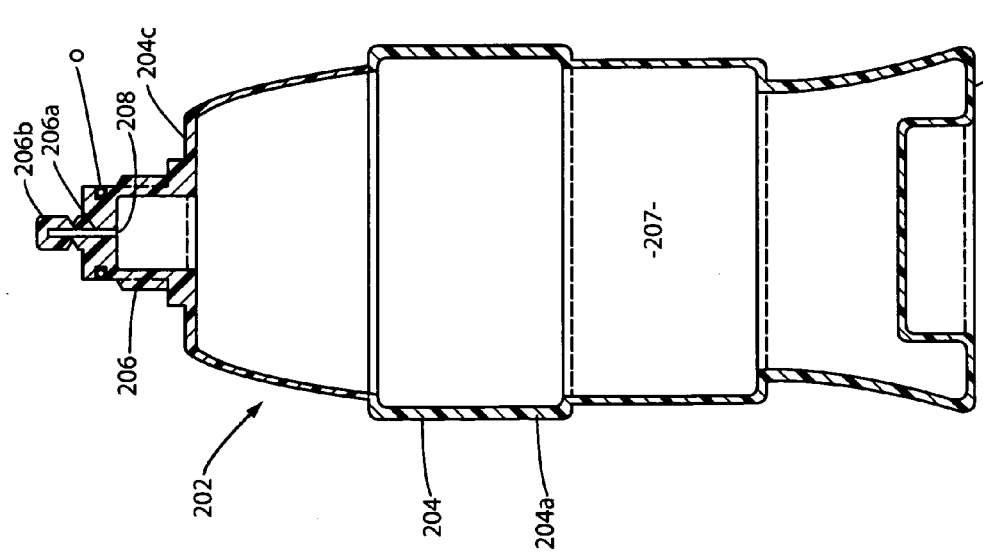

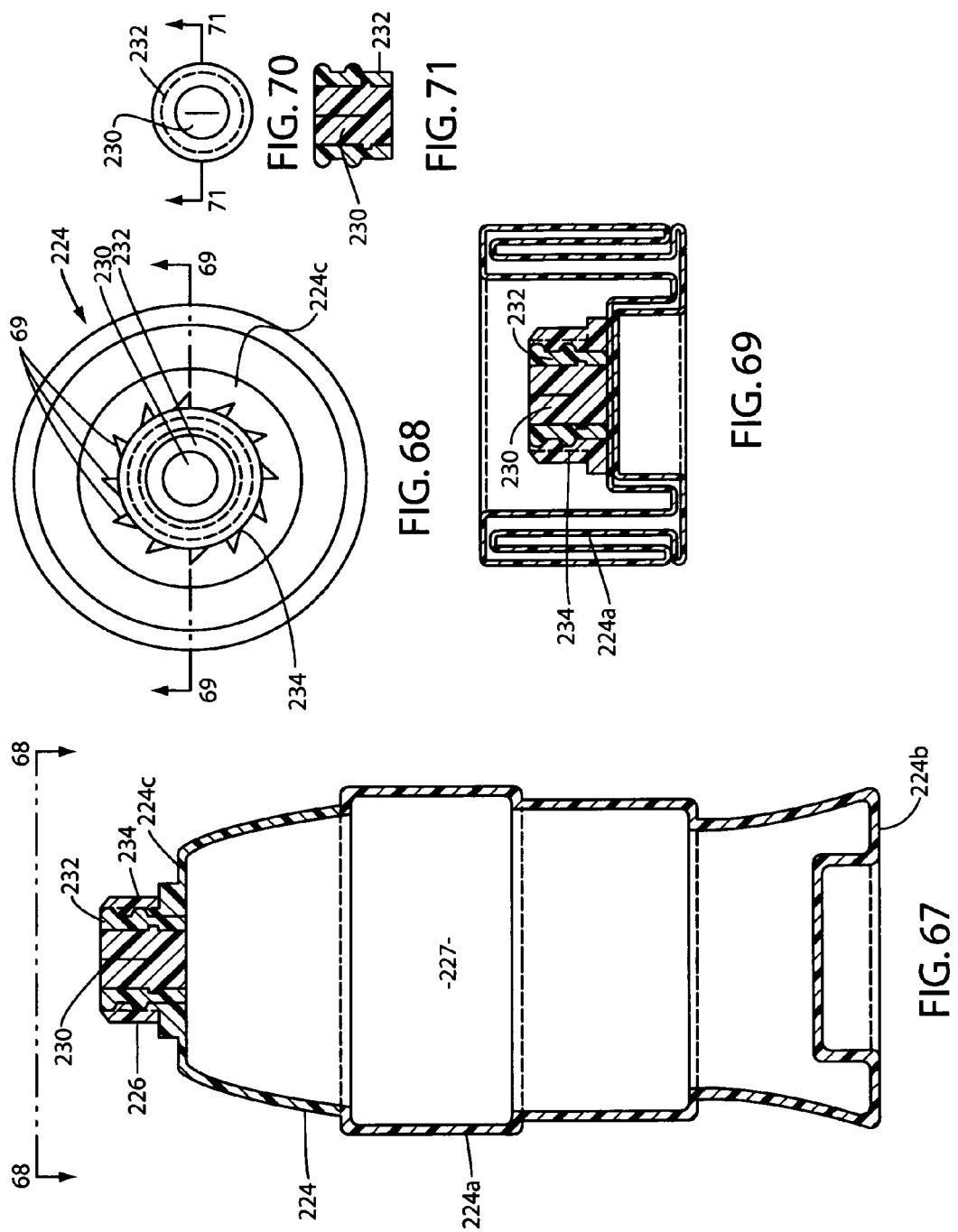

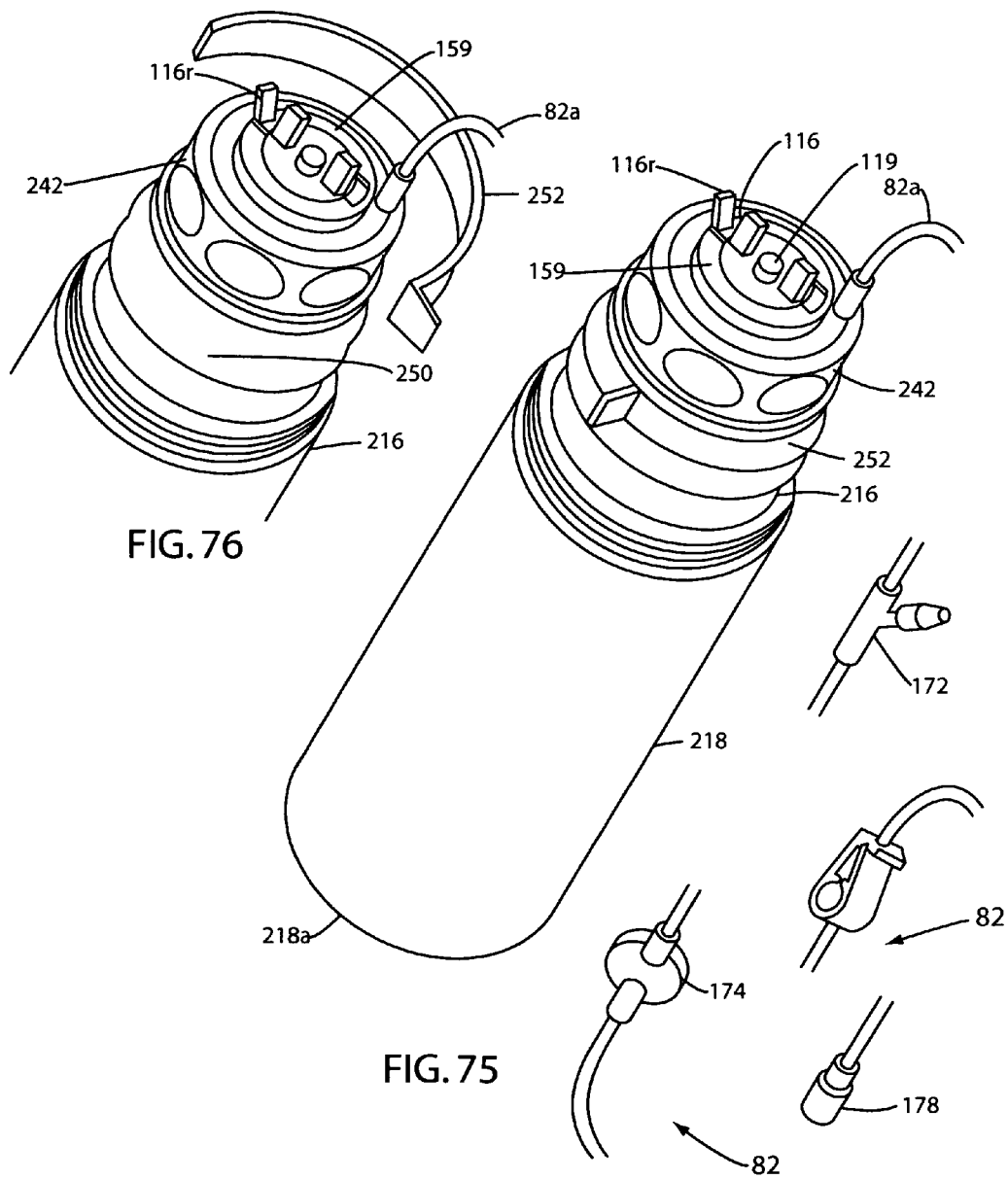

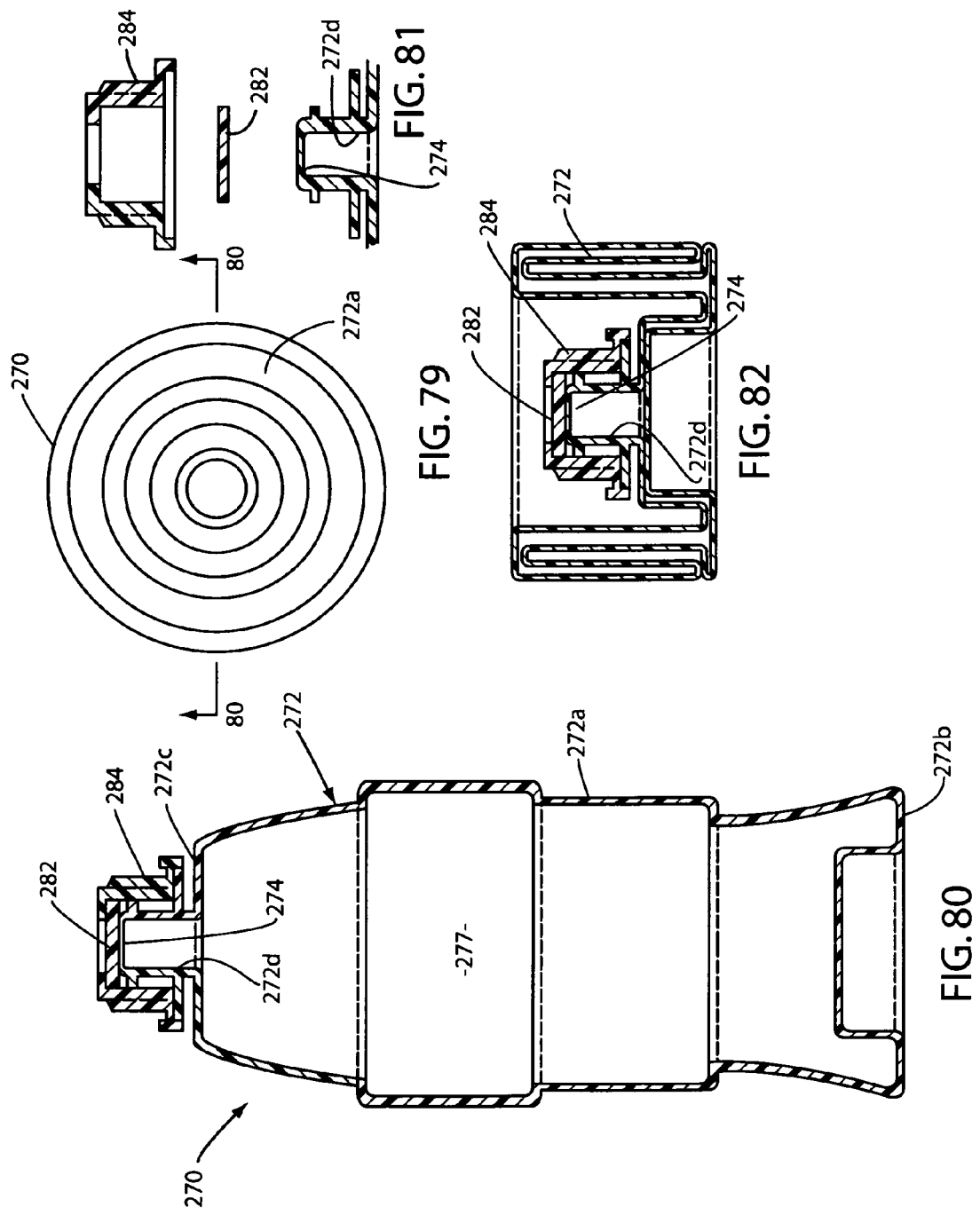

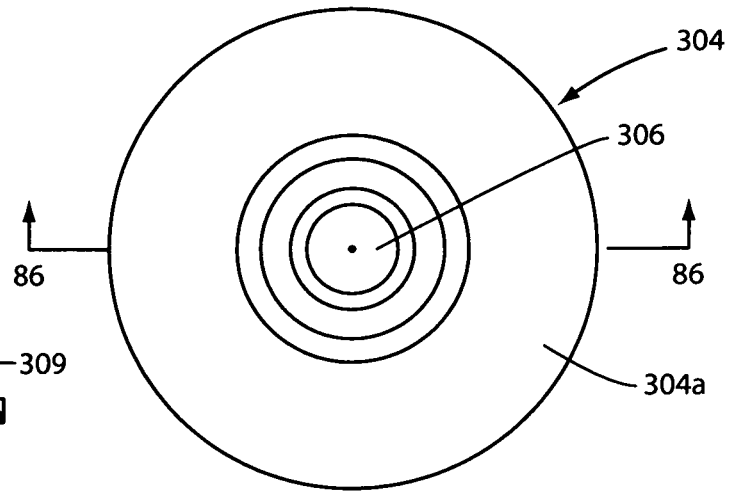
FIG. 85
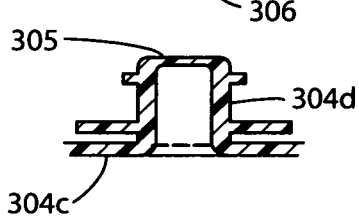
FIG. 87
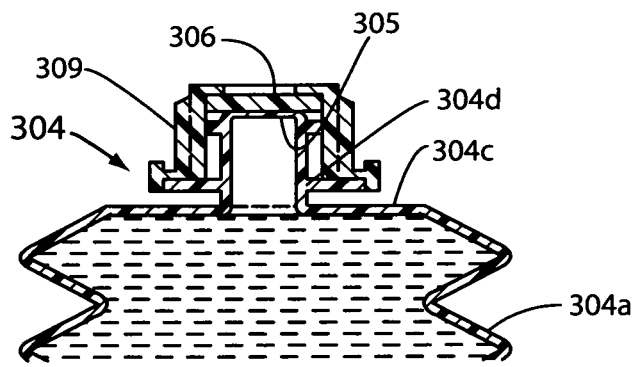
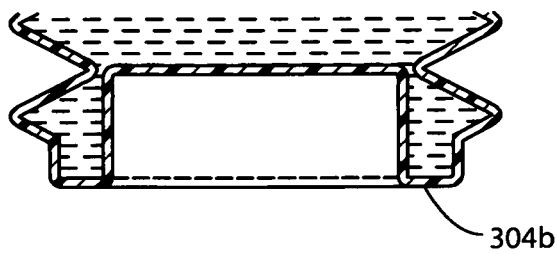
FIG. 86

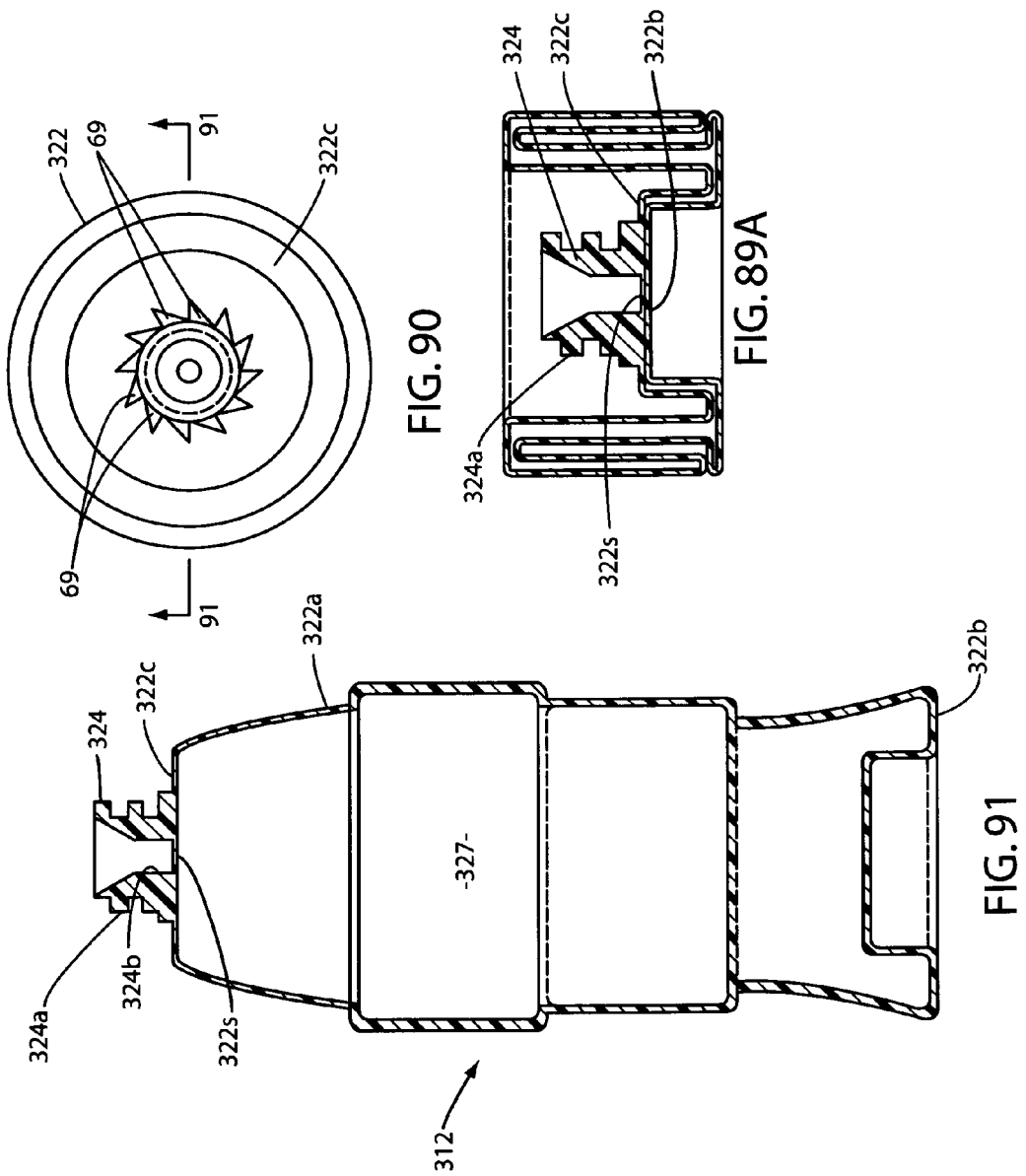

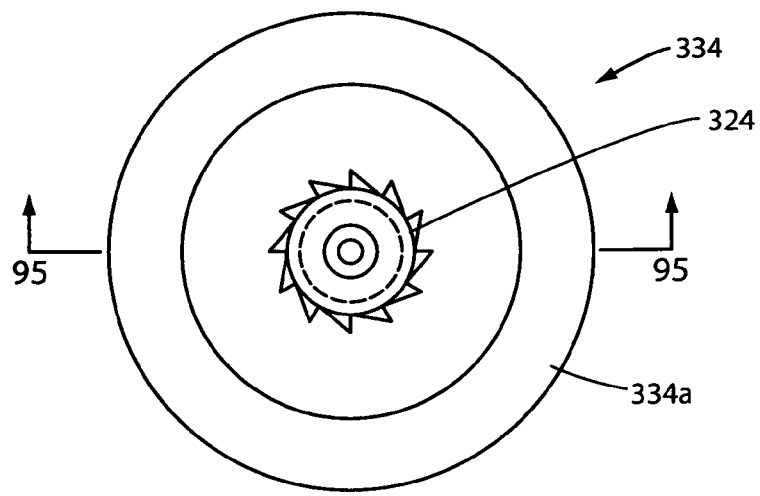
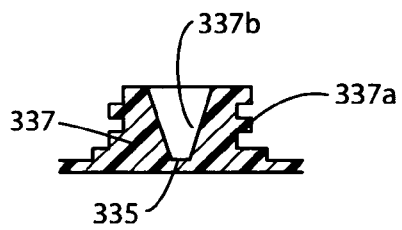
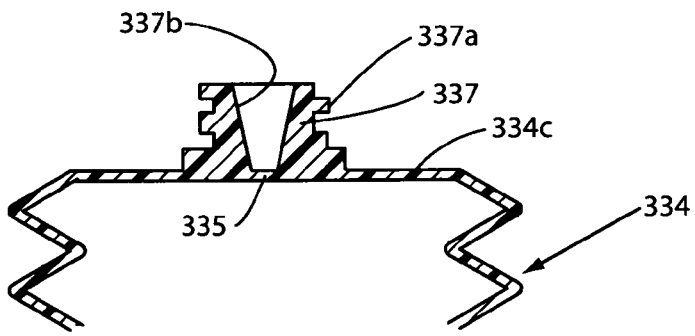
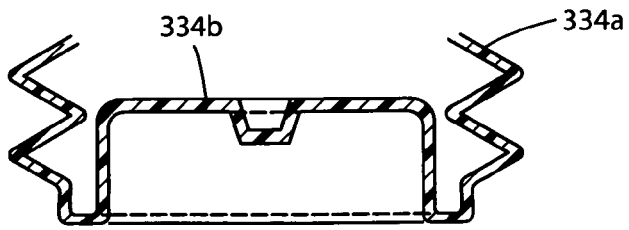
FIG. 94
FIG. 96
-337-
FIG. 95

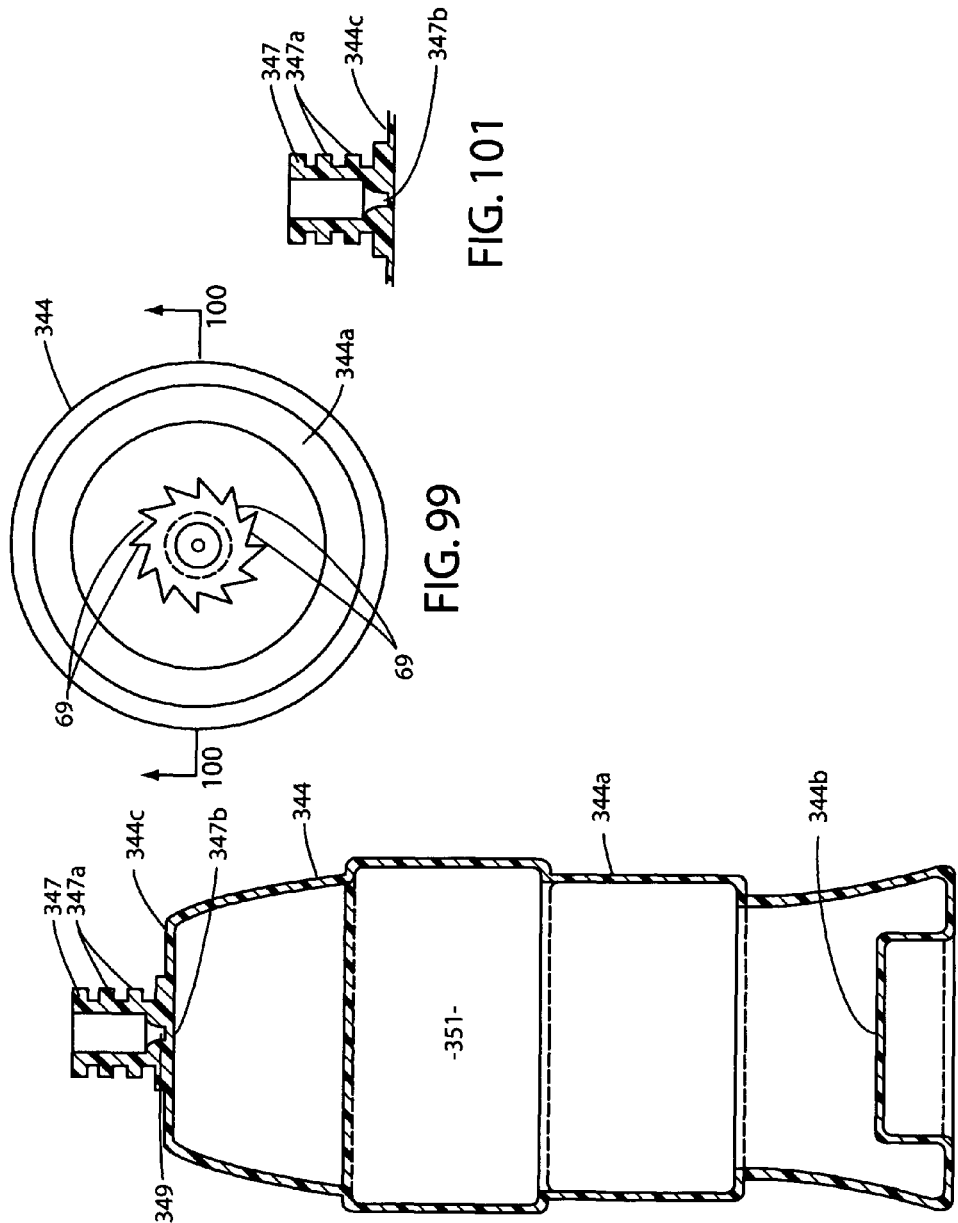

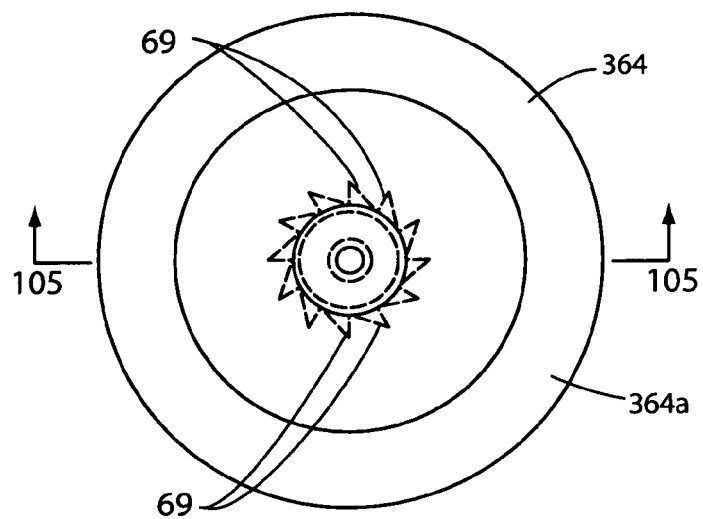
FIG. 104
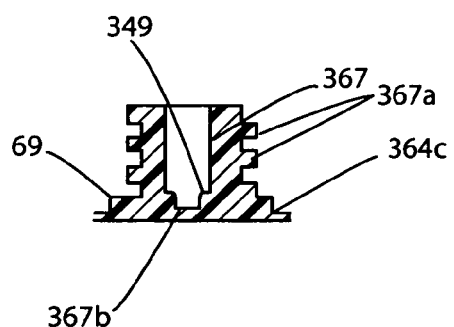
FIG. 106
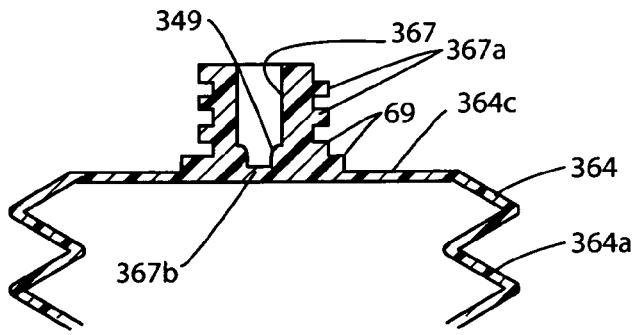
-367-
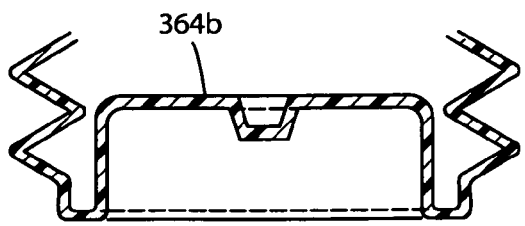
FIG. 105

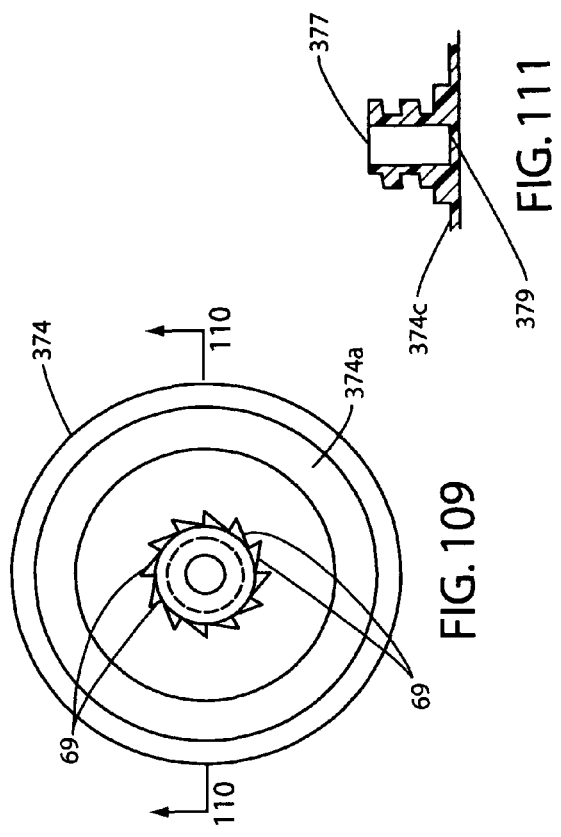
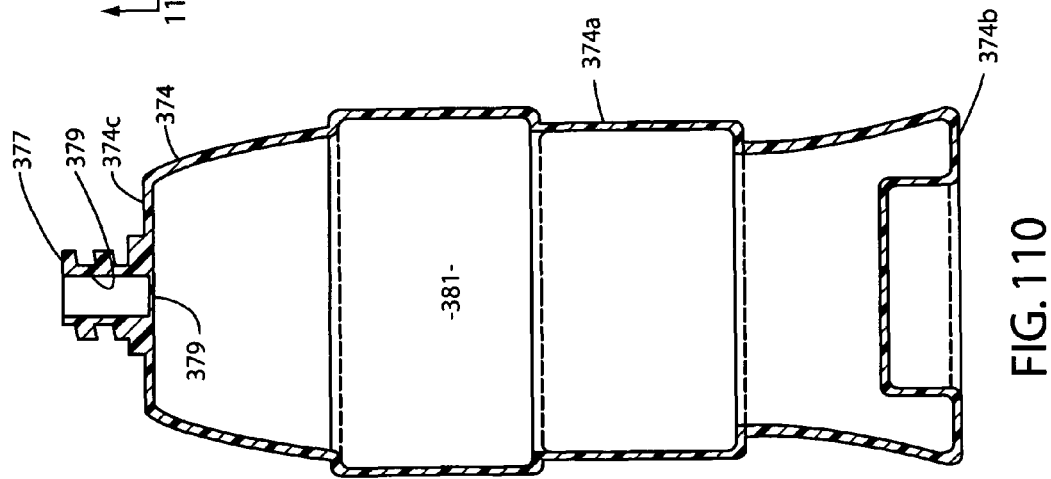

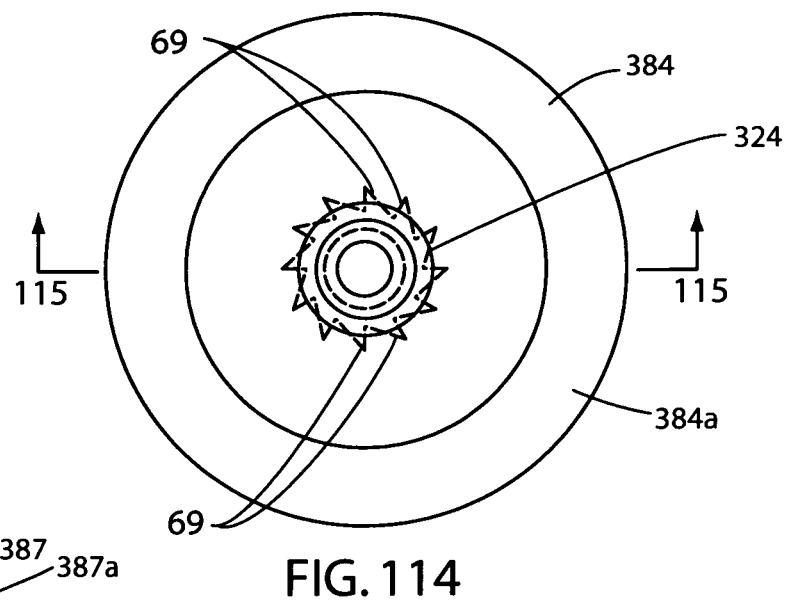
FIG. 114
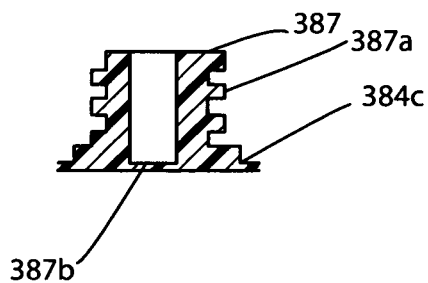
FIG. 116
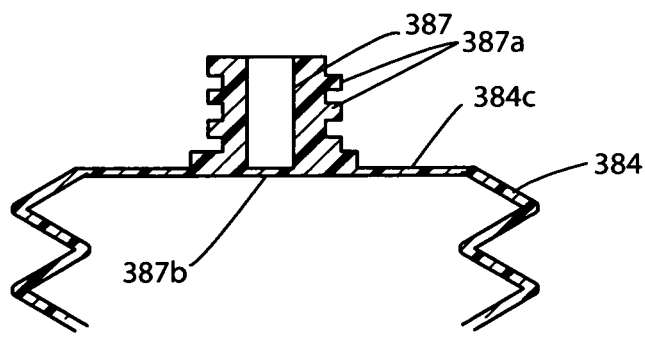
-389-
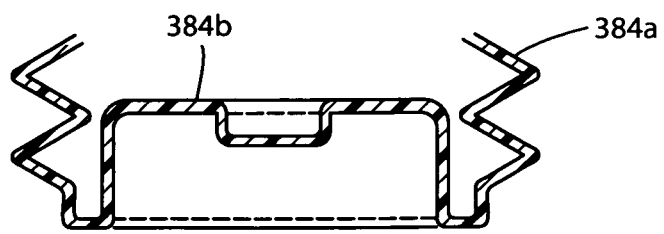
FIG. 115

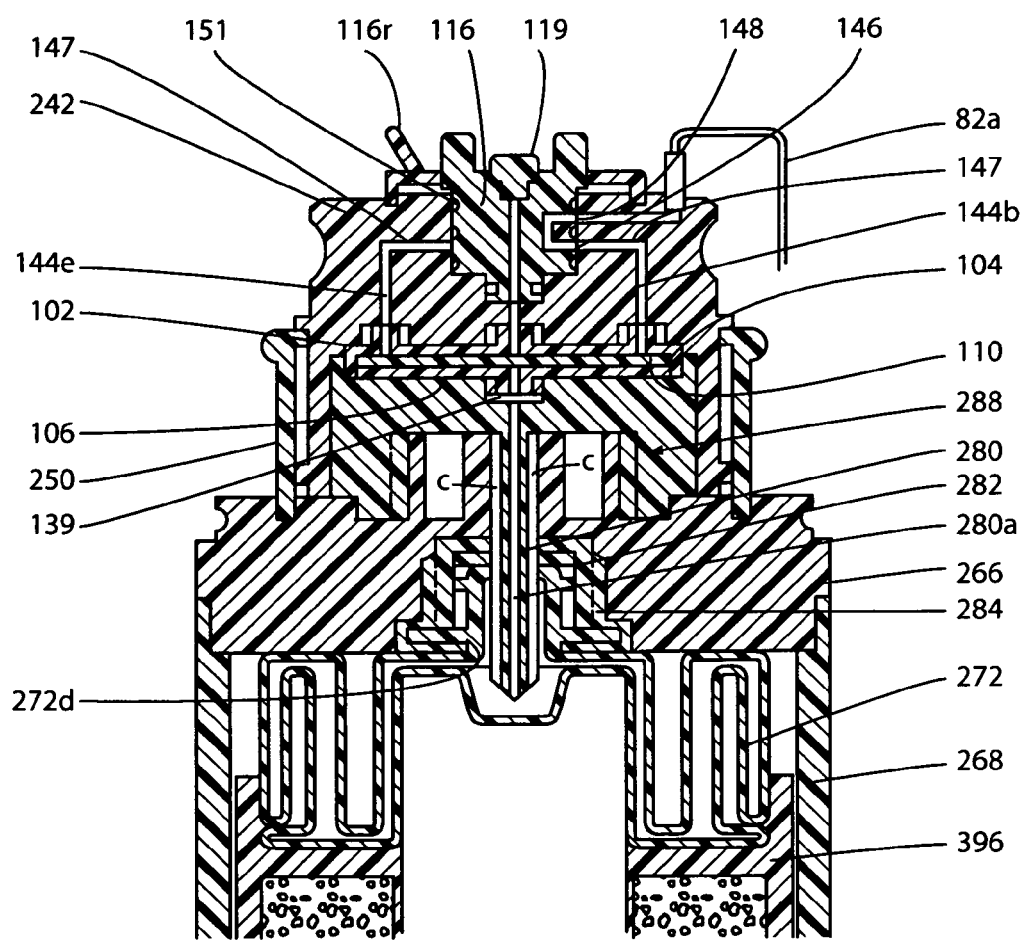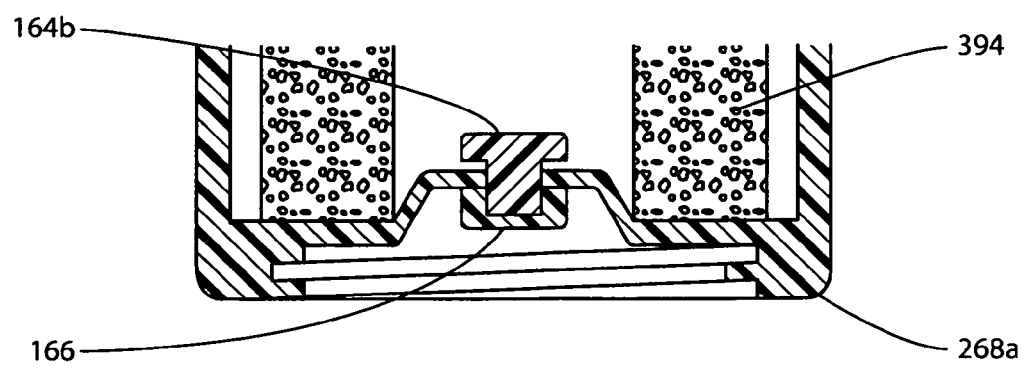
FIG. 118

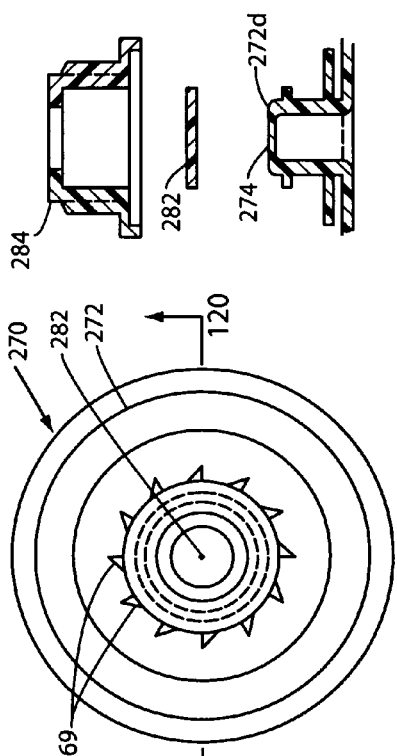
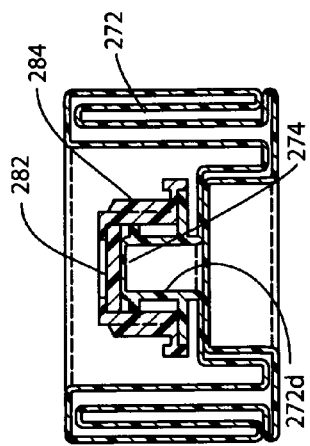
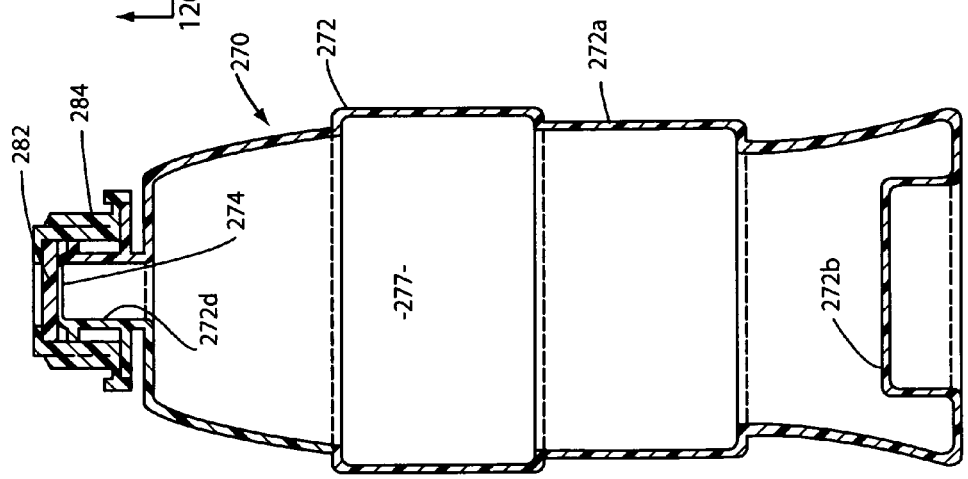

FLUID DISPENSING DEVICE

CROSS-REFERENCE TO RELATED APPLICATIONS

This is a divisional application of application U.S. Ser. No. 11/725,222 filed Mar. 14, 2007 (now U.S. Pat. No. 7,828,772) which claimed the benefit of provisional application U.S. Ser. No. 60/783,182 filed Mar. 15, 2006.

STATEMENT REGARDING FEDERALLY SPONSORED RESEARCH OR DEVELOPMENT

Not Applicable

INCORPORATION-BY-REFERENCE OF MATERIAL SUBMITTED ON A COMPACT DISC

Not Applicable

BACKGROUND OF THE INVENTION

1. Field of the Invention

The present invention relates generally to fluid dispensing devices. More particularly, the invention concerns medicament dispensers for dispensing medicinal fluids to ambulatory patients.

2. Description of Related Art Including Information Disclosed Under 37 CFR 1.97 and 1.98

A number of different types of medicament dispensers for dispensing medicaments to ambulatory patients have been suggested in the past. Many of the devices seek either to improve or to replace the traditional gravity flow and hypodermic syringe methods which have been the standard for delivery of liquid medicaments for many years.

The prior art gravity flow methods typically involve the use of intravenous administration sets and the familiar flexible solution bag suspended above the patient. Such gravametric methods are cumbersome, imprecise and require bed confinement of the patient. Periodic monitoring of the apparatus by the nurse or doctor is required to detect malfunctions of the infusion apparatus. Accordingly, the prior art devices are not well suited for use in those instances where the patient must be transported to a remote facility for treatment.

As will be fully appreciated from the discussion that follows, the devices of the present invention are particularly useful in ambulatory situations. The ability to quickly and efficaciously treat wounded soldiers, especially in unpredictable or remote care settings, can significantly improve chances for patient survival and recovery. Accurate intravenous (IV) drug and fluid delivery technologies for controlling pain, preventing infection, and providing a means for IV access for rapid infusions during patient transport are needed to treat almost all serious injuries.

It is imperative that battlefield medics begin administering life saving medications as soon as possible after a casualty occurs. The continuous maintenance of these treatments is vital until higher echelon medical facilities can be reached. A compact, portable and ready to use infusion device that could be easily brought into the battlefield would allow medics to begin drug and resuscitation agent infusions immediately. Additionally, it would free them to attend to other seriously wounded patients who may require more hands-on care in the trauma environment following triage. In most serious trauma situations on the battlefield, IV drug delivery is required to treat fluid resuscitation, as well as both pain and infection. Drug infusion devices currently available can impede administration of IV infusions in remote care settings.

Expensive electronic infusion pumps are not a practical field solution because of their weight and cumbersome size. Moreover, today's procedures for starting IV infusions on the battlefield are often dangerous because the attending medic must complete several time consuming steps. The labor intensive nature of current gravity solution bag modalities can prevent medics from attending to other patients also suffering from life threatening injuries. In some cases, patients themselves have been forced to hold flexible infusion bags elevated, in order to receive the medication by gravity drip.

With regard to the prior art, one of the most versatile and unique fluid delivery apparatus developed in recent years is that developed by one of the present inventors and described in U.S. Pat. No. 5,205,820. The components of this novel fluid delivery apparatus generally include: a base assembly, an elastomeric membrane serving as a stored energy means, fluid flow channels for filling and delivery, flow control means, a cover, and an ullage which comprises a part of the base assembly.

Another prior art patent issued to one of the present applicants, namely U.S. Pat. No. 5,743,879, discloses an injectable medicament dispenser for use in controllably dispensing fluid medicaments such as insulin, anti-infectives, analgesics, oncolytics, cardiac drugs biopharmaceuticals, and the like from a pre-filled container at a uniform rate. The dispenser, which is quite dissimilar in construction and operation from that of the present invention, includes a stored energy source in the form of a compressively deformable, polymeric elastomeric member that provides the force necessary to controllably discharge the medicament from a pre-filled container, which is housed within the body of the device. After having been deformed, the polymeric, elastomeric member will return to its starting configuration in a highly predictable manner.

BRIEF SUMMARY OF THE INVENTION

By way of brief summary, one form of the dispensing device of the present invention for dispensing medicaments to a patient comprises a supporting structure; a carriage assembly interconnected with the supporting structure for movement between a first position and a second position; a pre-filled collapsible container carried by the carriage assembly, the collapsible container having accessing means for accessing the reservoir comprising a frangible member in the form of a pierceable member or a shearable member. The device also includes a guide means connected to the supporting structure for guiding travel of the carriage assembly between the first position and said second positions; a stored energy source operably associated with the carriage assembly for moving the carriage assembly between the first and second positions; and an administration set, including an administration line interconnected with the outlet port of the collapsible reservoir.

With the forgoing in mind, it is an object of the present invention to provide a compact fluid dispenser for use in controllably dispensing fluid medicaments to ambulatory patients, such as, antibiotics, blood clotting agents, analgesics, KVO, artificial blood substitutes, resuscitation fluids, nutritional solutions, biologics, and like agents from pre-filled containers at a uniform rate.

Another object of the invention is to provide a small, compact pre-filled fluid dispenser that is aseptically filled and sealed at the time of manufacture.

Another object of the invention is to provide a fluid dispenser of simple construction that can be used in the field with a minimum amount of training.

Another object of the invention is to allow infusion therapy to be initiated quickly and easily on the battlefield so that the attending medic or medical professional can more efficiently deal with triage situations in austere environments.

Another object of the invention is to provide a dispenser in which a stored energy source is provided in the form of a compressible, expandable or retractable member of novel construction that provides the force necessary to continuously and uniformly expel fluid from the device reservoir.

Another object of the invention is to provide a dispenser of the class described which includes a fluid flow control assembly that precisely controls the flow of the medicament solution to the patient.

Another object of the invention is to provide a dispenser that includes precise variable flow rate selection.

Another object of the invention is to provide a fluid dispenser of simple construction, which embodies a collapsible, pre-filled, sealed drug container that contains the beneficial agents to be delivered to the patient. Uniquely, the container is formed as a unitary structure that includes a collapsible side wall and pierceable closure wall that isolates the beneficial agents contained within the container reservoir from external contaminants.

Another object of the invention is to provide a fluid dispenser as described in the preceding paragraph, which embodies a collapsible, pre-filled drug container that includes an integrally formed, sealed reservoir that contains the beneficial agents to be delivered to the patient and is provided with access assemblies of various configurations that enable ready access to the sealed reservoir be penetrating assemblies various configurations.

Another object of the invention is to provide a fluid dispenser of the class described which is compact, lightweight, is easy for ambulatory patients to use, is fully disposable, transportable, and is extremely reliable in operation.

Another object of the invention is to provide a fluid dispenser as described in the preceding paragraphs that is easy and inexpensive to manufacture in large quantities.

BRIEF DESCRIPTION OF SEVERAL VIEWS OF THE DRAWINGS

FIG. 1 is a generally perspective top view of one form of the fluid dispensing device of the present invention for dispensing medicaments to a patient.

FIG. 2 is a generally perspective bottom view of the fluid dispensing device shown in FIG. 1.

FIG. 12 is a side elevational view of one form of the control shaft of the flow control means of the invention.

FIG. 13 is a view taken along lines 13-13 of FIG. 12.

FIG. 14 is a view taken along lines 14-14 of FIG. 12.

FIG. 15 is an enlarged cross-sectional view taken along lines 15-15 of FIG. 12.

FIG. 16 is an enlarged front view of one form of the spring knife of the invention that is carried within cavities formed in the control shaft shown in FIG. 12.

FIG. 17 is a view taken along lines 17-17 of FIG. 16.

FIG. 18 is an enlarged cross-sectional view of a portion of the support structure and of the control shaft of the device illustrating the appearance of the components in their starting position.

FIG. 19 is a cross-sectional view similar to FIG. 18 but showing the appearance of the components after the initial rotation of the control shaft from a first position to a second position.

FIG. 20 is a cross-sectional view similar to FIG. 19 but showing the appearance of the components after further rotation of the control shaft from the second position to a third position.

FIG. 23 is a top plan view of one form of the selector member of the device for selecting the rate of fluid flow toward the patient.

FIG. 24 is a cross-sectional view taken along lines 24-24 of FIG. 23.

FIG. 24A is a view taken along lines 24A-24A of FIG. 24.

FIG. 24B is a cross-sectional view taken along lines 24B-24B of FIG. 24.

FIG. 25 is a view taken along lines 25-25 of FIG. 24.

FIG. 26 is a top plan view of the retainer member of the device which functions to retain the selector member in position.

FIG. 27 is a cross-sectional view taken along lines 27-27 of FIG. 26.

FIG. 27A is a cross-sectional view taken along lines 27A-27A of FIG. 26.

FIG. 34 is a top plan view of a portion of the supporting structure of the device shown in FIG. 1.

FIG. 35 is a cross-sectional view taken along lines 35-35 of FIG. 34.

FIG. 35A is a view taken along lines 35A-35A of FIG. 35.

FIG. 58 is a cross-sectional view of the collapsible container of this alternate embodiment of the invention.

FIG. 59 is a top plan view of the collapsible container.

FIG. 60 is a cross-sectional view taken along lines 60-60 of FIG. 59.

FIG. 61 is a cross-sectional view of the area designated as "61" in FIG. 60.

FIG. 67 is a cross-sectional view of the collapsible container of this latest form of the invention.

FIG. 68 is a top plan view of the collapsible container shown in FIG. 67.

FIG. 69 is a cross-sectional view taken along lines 69-69 of FIG. 68.

FIG. 70 is a top plan view of the pierceable septum of the collapsible container shown in FIG. 67.

FIG. 71 is a cross-sectional view taken along lines 71-71 of FIG. 70.

FIG. 75 is a generally perspective view of this latest embodiment of the invention as it appears with a top cover of the device removed.

FIG. 76 is an enlarged, foreshortened, longitudinal, cross-sectional view of the fluid dispensing device of this latest embodiment the invention illustrating the removal of the tear off strip of the device.

FIG. 79 is a top plan view of the collapsible container of this alternate embodiment of the invention.

FIG. 80 is a cross-sectional view taken along lines 80-80 of FIG. 79.

FIG. 81 is an exploded, cross-sectional view of the reservoir access assembly of this latest form of the invention.

FIG. 82 is a fragmentary, cross-sectional view of the collapsible container as it appears in the collapsed configuration.

FIG. 85 is a top plan view of the collapsible container of this alternate embodiment of the invention.

FIG. 86 is a foreshortened, cross-sectional view taken along lines 86-86 of FIG. 85.

FIG. 87 is an exploded, cross-sectional view of the reservoir access assembly of this latest form of the invention.

FIG. 89A is a fragmentary, cross-sectional view of the collapsible container as it appears in the collapsed configuration.

FIG. 90 is a top plan view of the collapsible container of this alternate embodiment of the invention.

FIG. 91 is a cross-sectional view taken along lines 91-91 of FIG. 90.

FIG. 94 is a top plan view of the collapsible container of this alternate embodiment of the invention.

FIG. 95 is a foreshortened, cross-sectional view taken along lines 95-95 of FIG. 94.

FIG. 96 is a cross-sectional view of the Luer-like reservoir access assembly of this latest form of the invention.

FIG. 99 is a top plan view of the collapsible container of this alternate embodiment of the invention.

FIG. 100 is a cross-sectional view taken along lines 100-100 of FIG. 99.

FIG. 101 is a cross-sectional view of the Luer-like reservoir access assembly of this latest form of the invention.

FIG. 104 is a top plan view of the collapsible container of this alternate embodiment of the invention.

FIG. 105 is a foreshortened, cross-sectional view taken along lines 105-105 of FIG. 104.

FIG. 106 is a cross-sectional view of the Luer-like reservoir access assembly of this latest form of the invention.

FIG. 109 is a top plan view of the collapsible container of this alternate embodiment of the invention.

FIG. 110 is a cross-sectional view taken along lines 110-110 of FIG. 109.

FIG. 111 is a cross-sectional view of the Luer-like reservoir access assembly of this latest form of the invention.

FIG. 114 is a top plan view of the collapsible container of this alternate embodiment of the invention.

FIG. 115 is a foreshortened, cross-sectional view taken along lines 115-115 of FIG. 114.

FIG. 116 is a cross-sectional view of the Luer-like reservoir access assembly of this latest form of the invention.

FIG. 117 is a foreshortened, longitudinal, cross-sectional view of still another alternate form of the fluid dispensing device of the invention.

FIG. 118 is a foreshortened longitudinal, cross-sectional view similar to FIG. 117, but showing the various components of the device as they appear following delivery to the patient of the fluid contained within the device reservoir.

FIG. 119 is a top plan view of the collapsible container of this alternate embodiment of the invention.

FIG. 120 is a cross-sectional view taken along lines 120-120 of FIG. 119.

FIG. 121 is a cross-sectional, exploded view of the reservoir access assembly of this latest form of the invention.

FIG. 122 is a fragmentary, cross-sectional view of the collapsible container as it appears in the collapsed configuration.

FIG. 123 is a foreshortened, longitudinal, cross-sectional view of yet another alternate form of the fluid dispensing device of the invention.

FIG. 124 is a foreshortened longitudinal, cross-sectional view similar to FIG. 123, but showing the various components of the device as they appear following delivery to the patient of the fluid contained within the device reservoir.

FIG. 125 is a top plan view of the collapsible container of this alternate embodiment of the invention.

Figure 125:
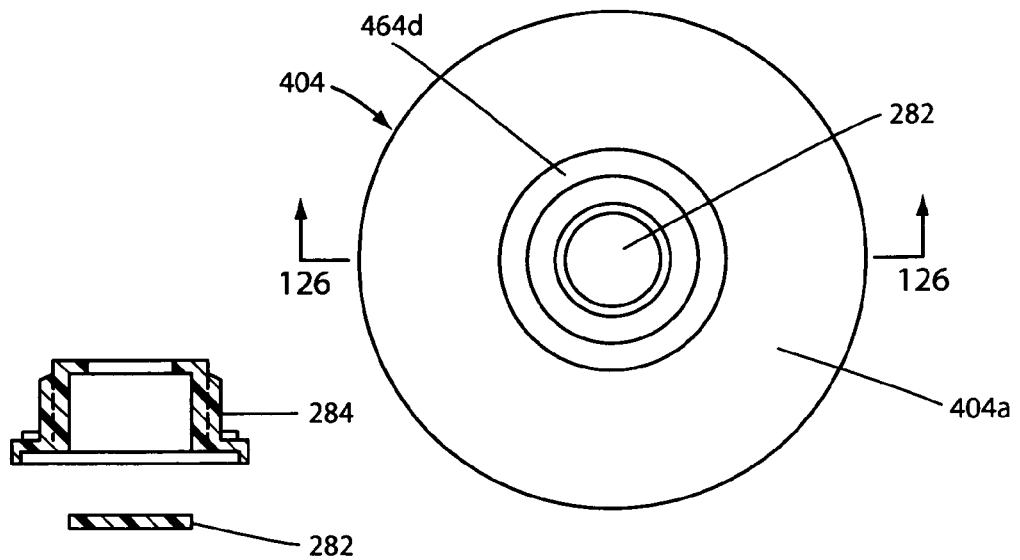
Figure 126:
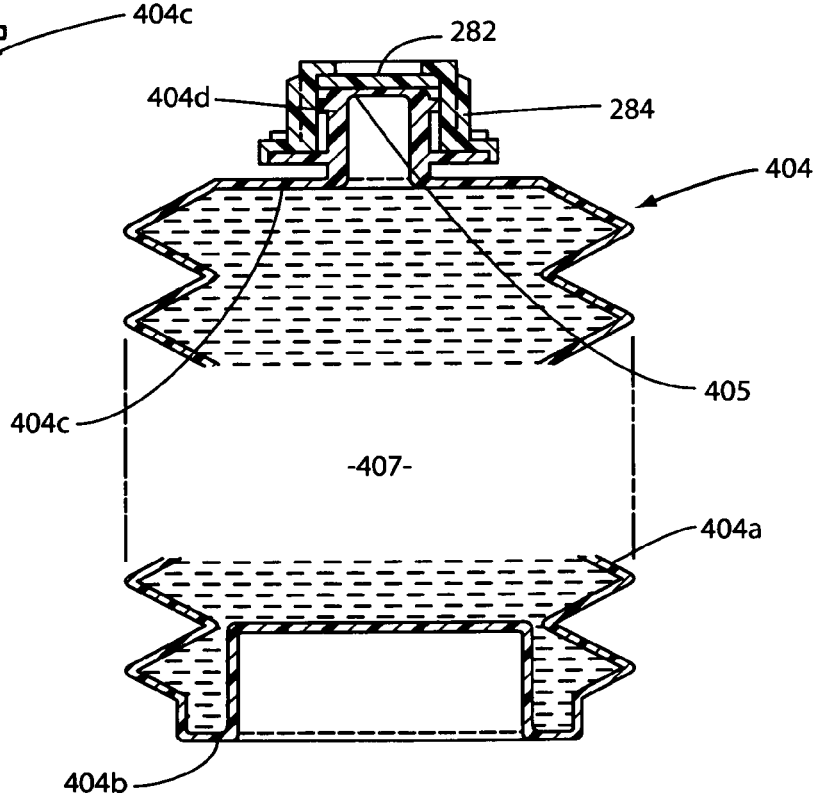

FIG. 126 is a foreshortened, cross-sectional view taken along lines 126-126 of FIG. 125.

Figure 127:
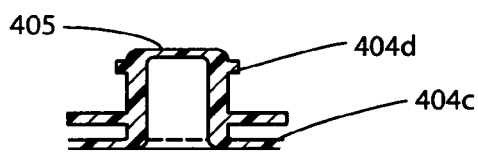

FIG. 127 is a cross-sectional view of the Luer-like reservoir access assembly of this latest form of the invention.

Figure 128:
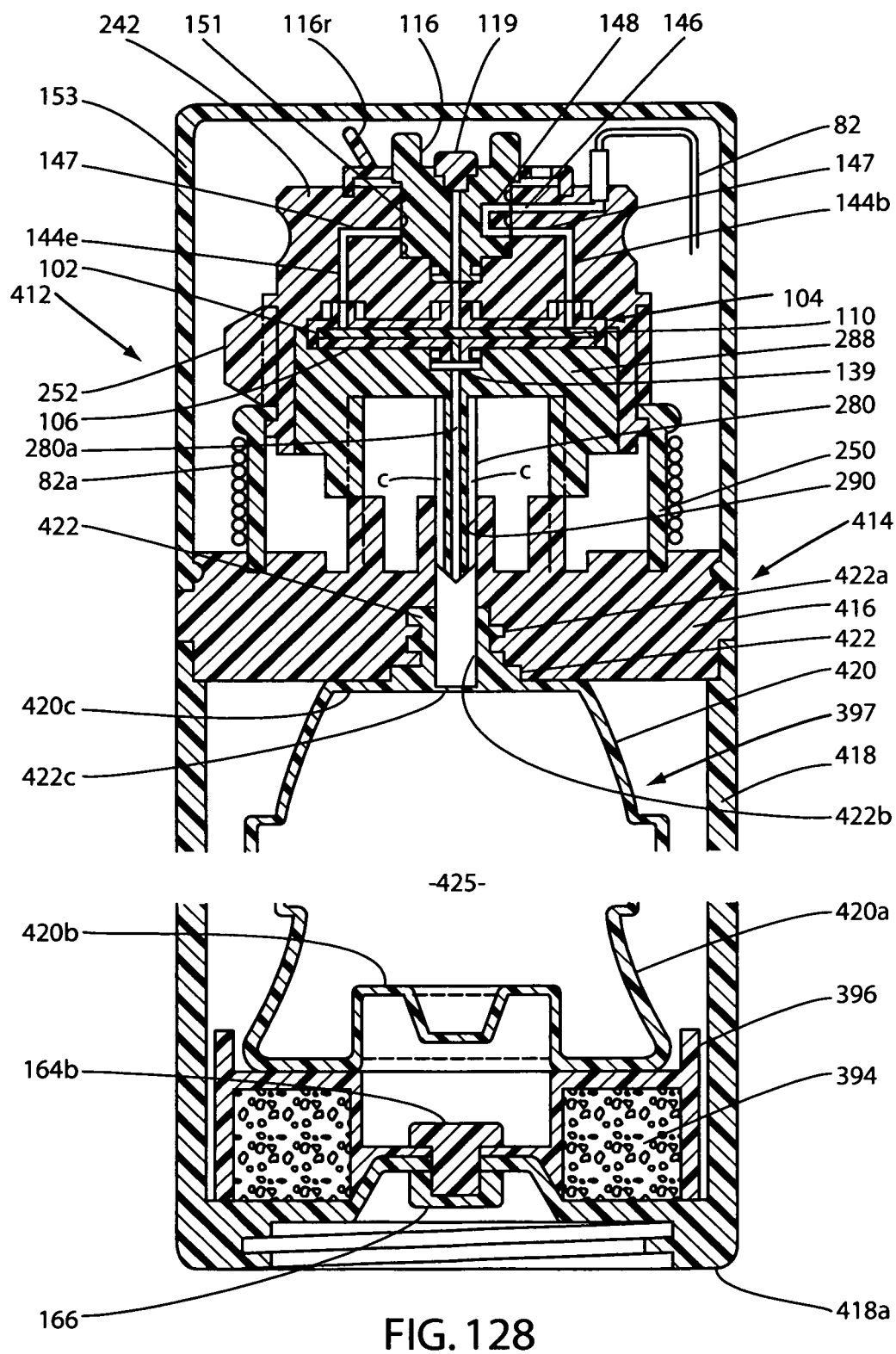

FIG. 128 is a foreshortened, longitudinal, cross-sectional view of still another alternate form of the fluid dispensing device of the invention.

Figure 129:
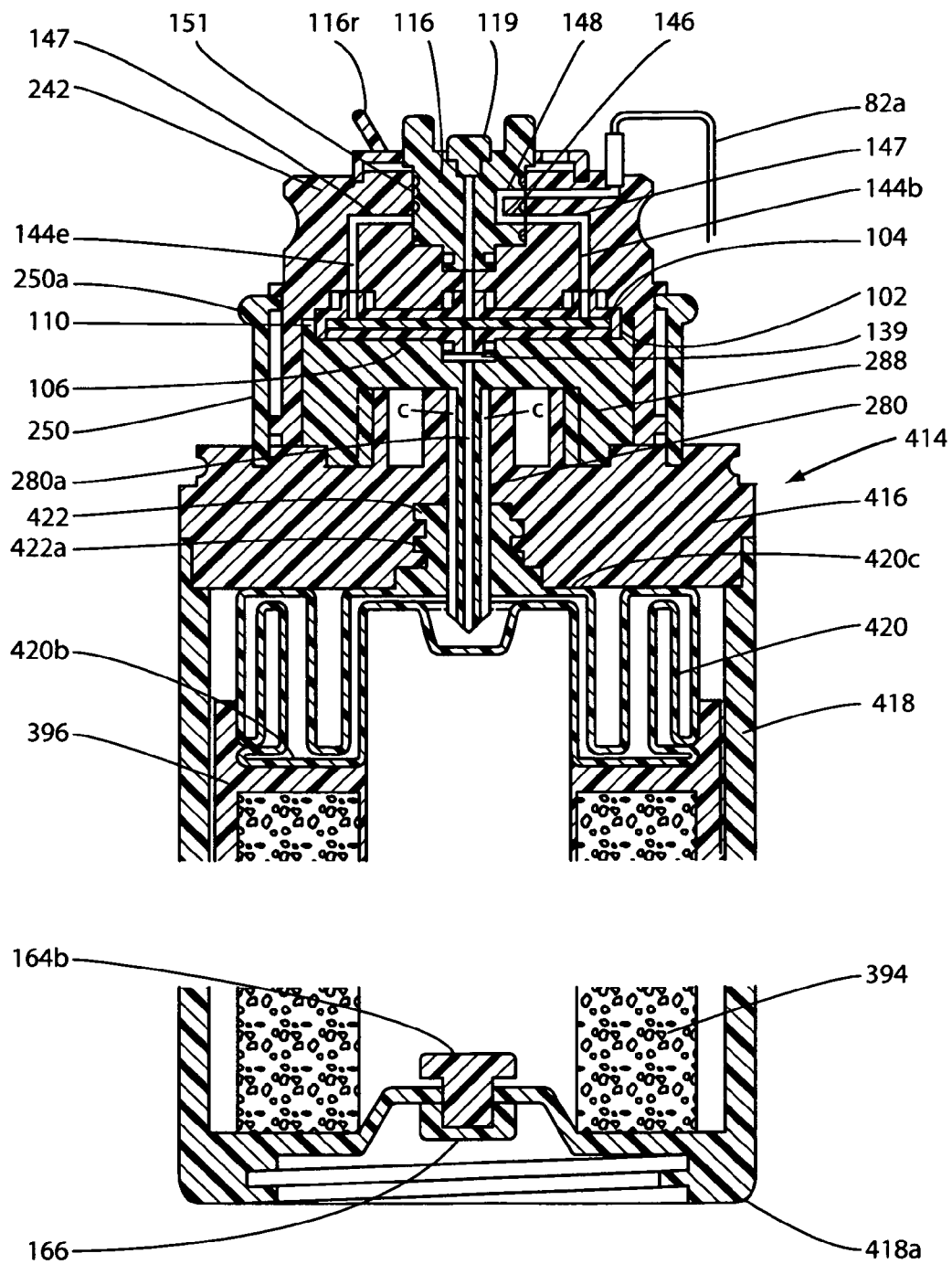

FIG. 129 is a foreshortened longitudinal, cross-sectional view similar to FIG. 128, but showing the various components of the device as they appear following delivery to the patient of the fluid contained within the device reservoir.

Figure 130:
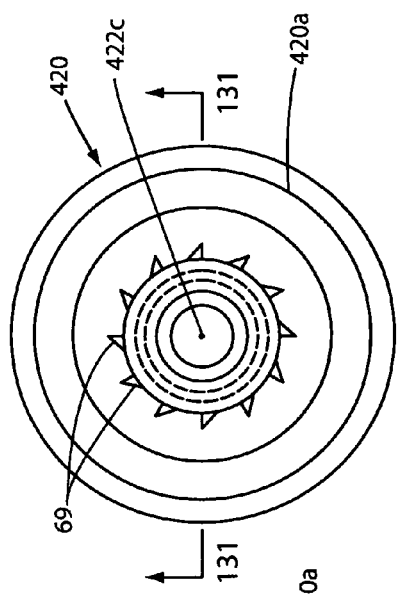

FIG. 130 is a top plan view of the collapsible container of this alternate embodiment of the invention.

Figure 131:
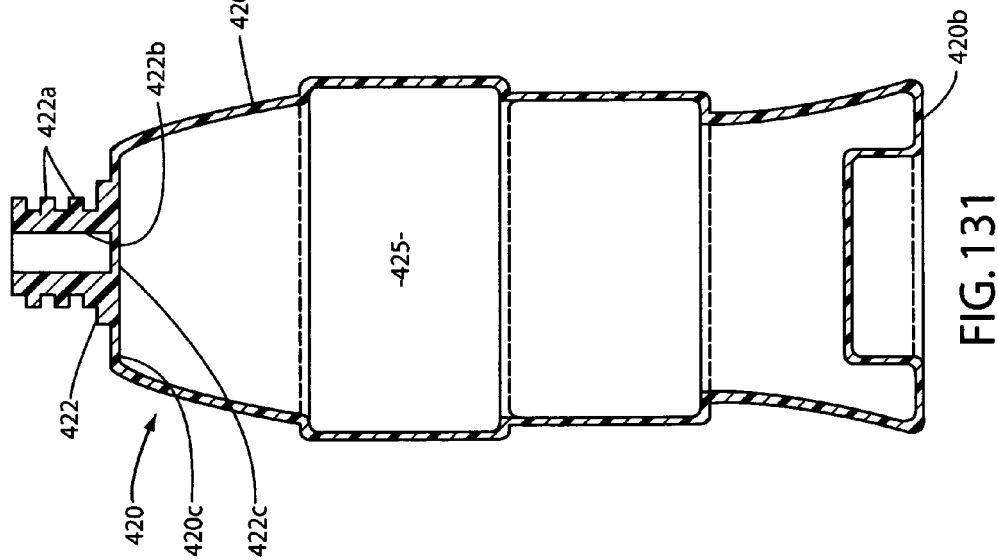

FIG. 131 is a cross-sectional view taken along lines 131-131 of FIG. 130.

Figure 132:
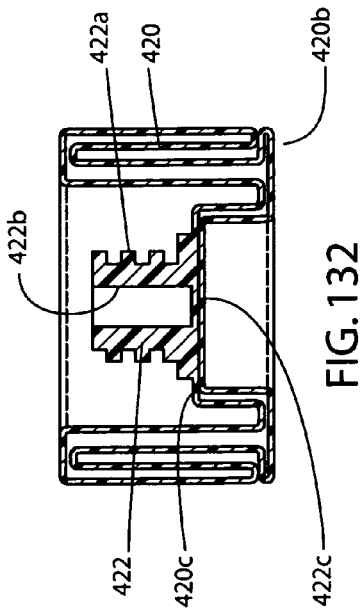

FIG. 132 is a fragmentary, cross-sectional view of the collapsible container as it appears in the collapsed configuration.

Figure 133:
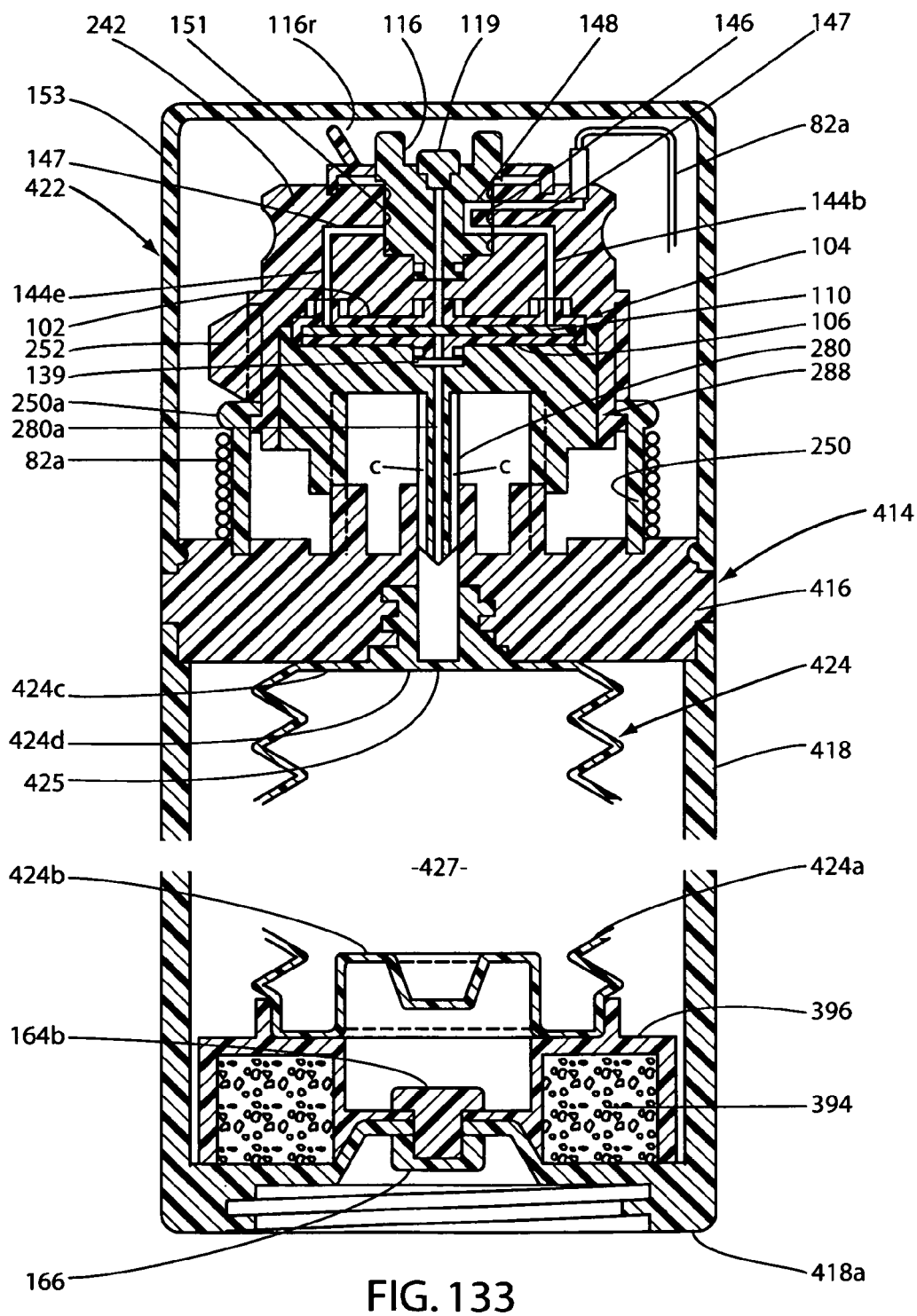

FIG. 133 is a foreshortened, longitudinal, cross-sectional view of still another alternate form of the fluid dispensing device of the invention.

Figure 134:
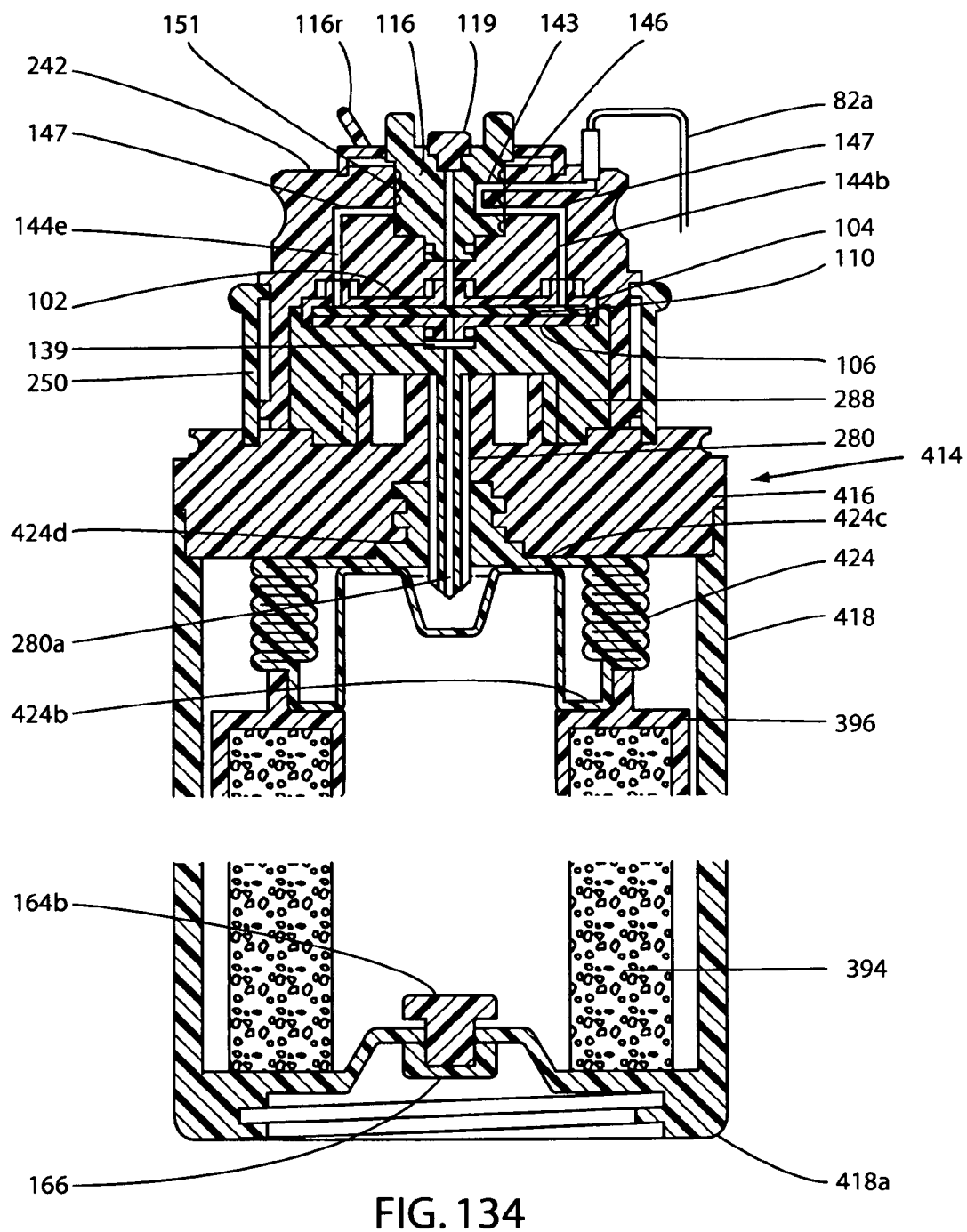

FIG. 134 is a foreshortened longitudinal, cross-sectional view similar to FIG. 133, but showing the various components of the device as they appear following delivery to the patient of the fluid contained within the device reservoir.

DETAILED DESCRIPTION OF THE INVENTION

Definitions

As used herein, the following terms have the following meanings:

Unitary Container

A closed container formed from a single component.

Continuous/Uninterrupted Wall.

A wall having no break in uniformity or continuity.

Biologic

A virus, therapeutic serum, toxin, antitoxin, vaccine, blood, blood component or derivative, allergenic product, or analogous product applicable to the prevention, treatment or cure of diseases or injuries of the human or animal body.

Hermetically Sealed Container

A container that is designed and intended to be secure against the entry of microorganisms and to maintain the safety and quality of its contents after pressurizing.

Drug

As defined by the Food, Drug and Cosmetic Act, drugs are "articles (other than food) intended for the use in the diagnosis, cure, mitigation, treatment, or prevention of disease in man or other animals, or to affect the structure or any function."

Drug Product

A finished dosage form (e.g. tablet, capsule, or solution) that contains the active drug ingredient usually combined with inactive ingredients.

Artificial Blood Substitutes

Blood Substitutes are used to fill fluid volume and/or carry oxygen and other gases in the cardiovascular system. These include volume expanders for inert products, and oxygen therapeutics for oxygen-carrying products.

Resuscitation Fluids

Infusion of hyperosmotic-hyperoncotic solutions such as hypertonic saline dextran (HSD) as used for resuscitation of traumatic shock and perioperative volume support or as an adjunct to other conventional isotonic crystalloid solutions. Where hypotension is caused by myocardial depression, pathological vasodilatation and extravascation of circulating volume due to widespread capillary leak, a resuscitative effort is attempted to correct the absolute and relative hypovolemia by refilling the vascular tree. Here resuscitation with a small volume of hypertonic-hyperoncotic solution allows systemic and splanchnic hemodynamic and oxygen transport recovery, without an increase in pulmonary artery pressure. Alternate types of normotonic, hyperoncotic, hypertonic, and hypertonic-hyperoncotic solutions can be used for systemic hemodynamic recovery.

KVO

KVO—keeping-the-vein-open in an IV set up; is a phrase that refers to the flow rate of a maintenance IV line established as a prophylactic access.

Nutritionals

Dietary supplemental enteral nutrition support feeding solutions used for nasoenteric application typically used in nasogastric, nasoduodenal, nasojejunal, or intravenous routes of administration.

Beneficial Agent

The term beneficial agent can include any substance or compound that is biologically active and includes any physiologically or pharmacologically active substance that produces a localized or systemic effect in humans or animals and that can be delivered by the present invention to produce a beneficial and useful result.

Diluent

A liquid that which dilutes, as in an inert solution used to dilute a medicament. An inert liquid carrier of a beneficial agent.

Device

An instrument, apparatus, implement, machine, contrivance, implant, in vitro reagent, or other similar or related article, including any component, part or accessory, which is intended for use in the diagnosis, cure, treatment or prevention of disease. A device does not achieve its intended purpose through chemical action in the body and is not dependent upon being metabolized to achieve its purpose.

Apparatus

An appliance or device for a particular purpose: An integrated group of materials or devices used for a particular purpose. The totality of means by which a designated function is performed or a specific task executed; a group of body parts that work together to perform a given function.

Reservoir

A receptacle or chamber for storing a fluid. A part of a machine, device, where liquid is stored.

Liquid Container

A receptacle for holding a liquid. A fluid dispenser that is carried or transported.

Collapsible

To cause to fold, break down, or fall down or inward or as in bent-over or doubled-up so that one part lies on another.

Collapsible Container

A dispensing device in which one or more walls of the container are made of a material, which will deform (collapse) when pressure is applied thereto; or a dispensing device having a collapsible or telescoping wall structure.

Aseptic Processing

The term 'aseptic processing' as it is applied in the pharmaceutical industry refers to the assembly of sterilized components and product in a specialized clean environment.

Sterile Product

A sterile product is one that is free from all living organisms, whether in a vegetative or spore state.

Blow-Fill-Seal Process

The concept of aseptic blow-fill-seal (BFS) is that a container is formed, filled, and sealed as a unitary container in a continuous manner without human intervention in a sterile enclosed area inside a machine. The process is multi-stepped, pharmaceutical grade resin is extruded into a tube, which is then formed into a container. A mandrel is inserted into the newly formed container and filled. The container is then sealed, all inside a sterile shrouded chamber. The product is then discharged to a non-sterile area for packaging and distribution.

Integrally Formed

An article of one-piece construction, or several parts that are rigidly secured together, smoothly continuous in form and that any such components making up the part have been then rendered inseparable.

Septum

A word borrowed from the Latin "saeptum" meaning a dividing wall or enclosure; thus, a thin partition or membrane that divides two spaces.

Slit Septum

A septum that is partially slit to aid in cannula penetration.

Penetrating

Tending to penetrate; having the power of entering or piercing.

Cutting

Capable of or designed for incising, shearing, or severing as to cut off from a main body.

Frangible

An article, item or object that is capable of being ruptured or broken, but does not necessarily imply any inherent materials weakness. A material object under load, that demonstrates a mechanical strain rate deformation behavior leading to disintegration.

Luer-Like Connector

A connector used to connect medical devices. Classically, the Luer consists of a tapered barrel and a conical male part that fits into it with or without a seal.

Surface Treatment

The processes of surface treatments, more formally surface engineering, to tailor the surfaces of engineering materials to change, alter or modify the physical surface characteristics and improve the function of the materials properties for its intended purpose.

Spring

A mechanical element that can be deformed by a mechanical force such that the deformation is directly proportional to the force or torque applied to it. An elastic machine component able to deflect under load in a prescribed manner and to recover its initial shape when unloaded. The combination of force and displacement in a deflected spring is energy, which may be stored when moving loads are being arrested.

Constant Force Spring

Constant force springs are a special variety of extension spring. They are tightly coiled wound bands of pre-hardened spring steel or stainless steel strip with built-in curvature so that each turn of the strip wraps tightly on its inner neighbor. When the strip is extended (deflected), the inherent stress resists the loading force, the same as a common extension spring but at a nearly constant (zero) rate. The constant-force spring is well suited to long extensions with no load build-up. In use, the spring is usually mounted with the ID tightly wrapped on a drum and the free end attached to the loading force. Considerable flexibility is possible with constant-force springs because the load capacity can be multiplied by using two or more strips in tandem, or back-to-back. Constant force springs are available in a wide variety of sizes.

Apparatus of the Invention

Referring to the drawings and particularly to FIGS. 1 through 8, one form of the dispensing device of the present invention for dispensing medicaments to a patient is there shown and generally designated by the numeral 50. The dispensing device here includes a supporting structure 52, which includes a connector assembly 54 and a generally cylindrically shaped outer housing 56 that is interconnected with the connector assembly in the manner best seen in FIG. 4 of the drawings. Supporting structure 52 can be constructed from metal, plastic or any suitable material. Outer housing 56 includes a generally cylindrically shaped wall portion 56a and a threaded base portion 56b, the purpose of which will presently be described.

Figure 3:
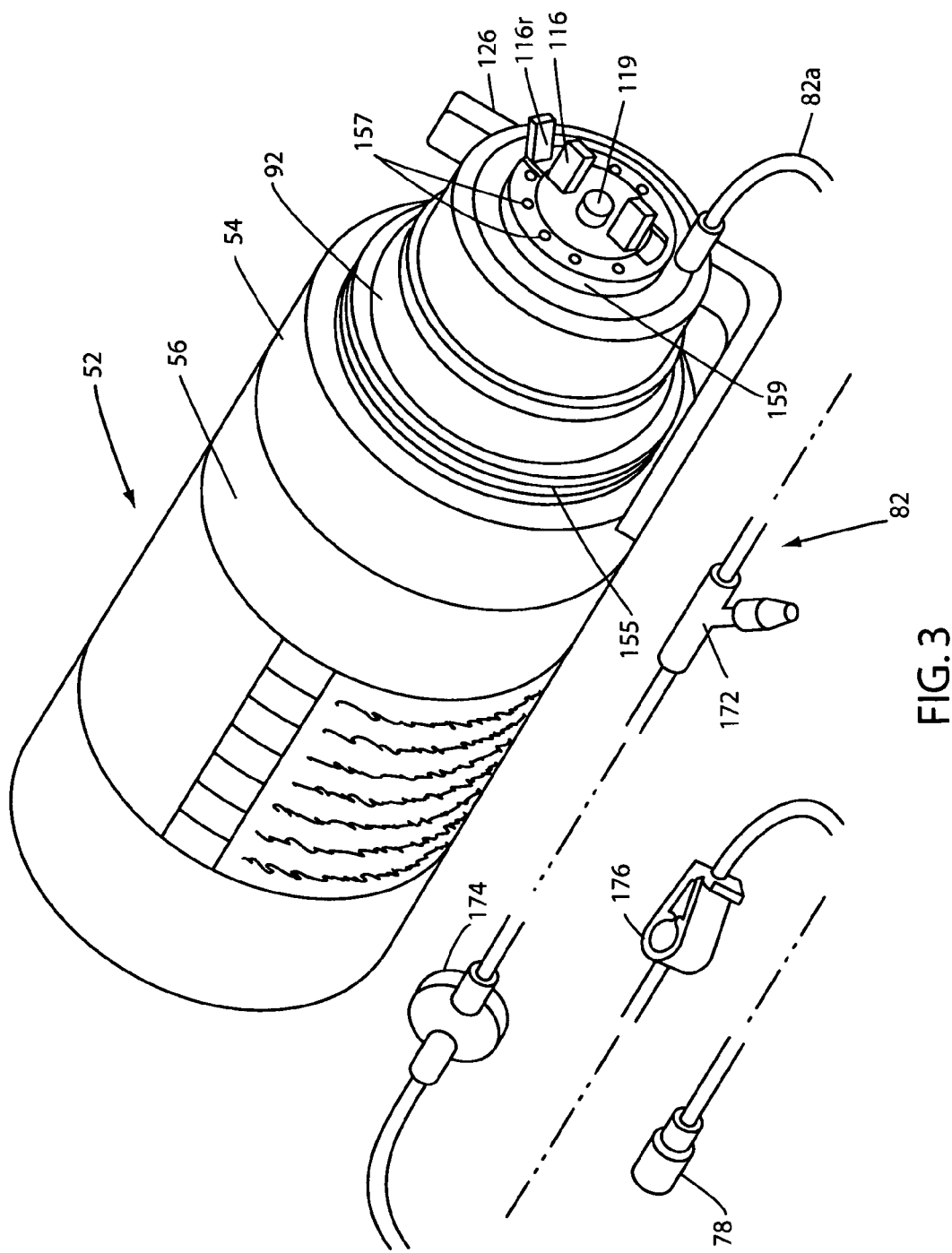
FIG. 3 is a generally perspective view of the fluid dispensing device shown in FIG. 1 as it appears with the top cover of the device removed.
Figure 4:
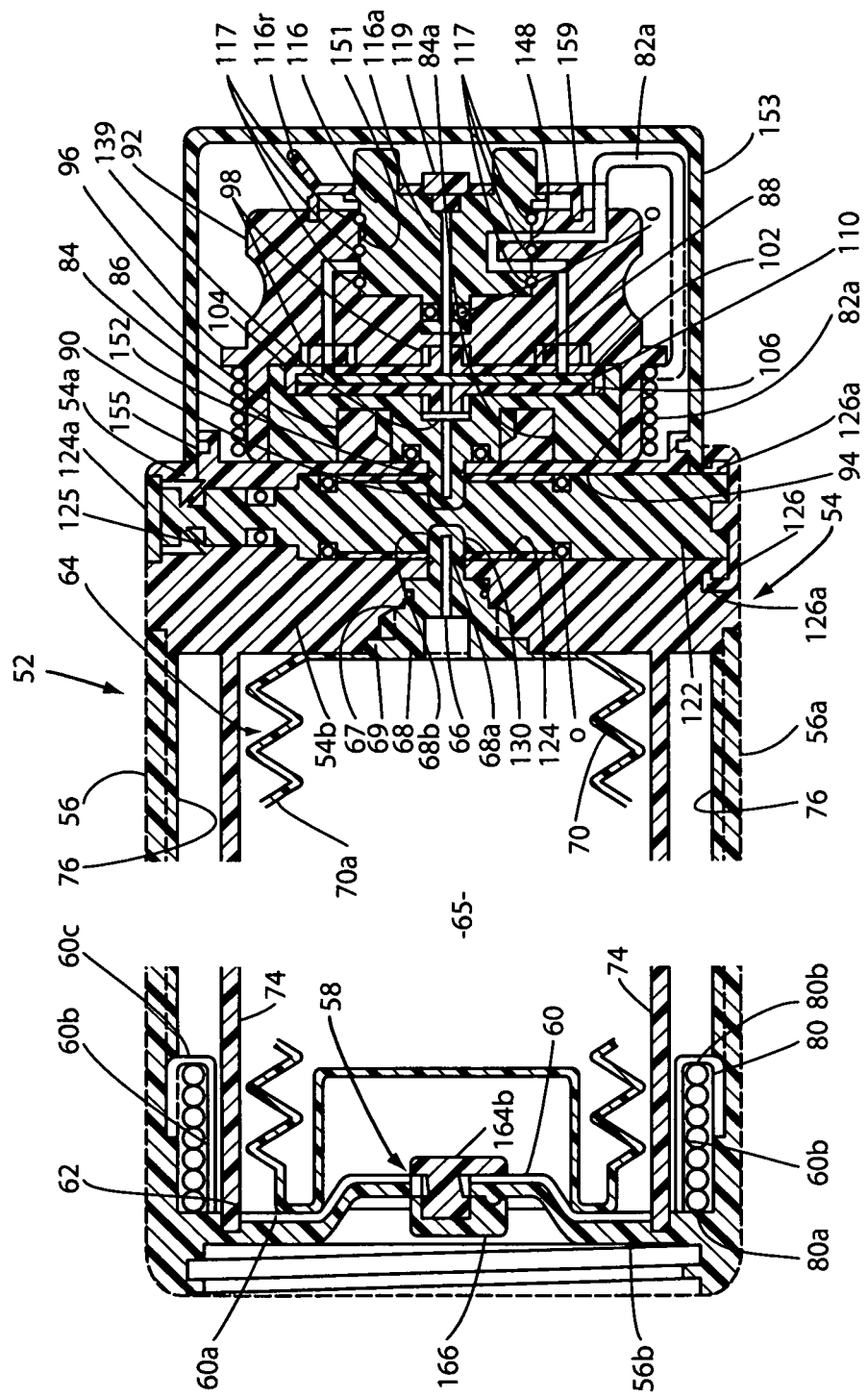
FIG. 4 is an enlarged, foreshortened, longitudinal, cross-sectional view of the pre-filled fluid dispensing device illustrated in FIG. 1.
Figure 5:
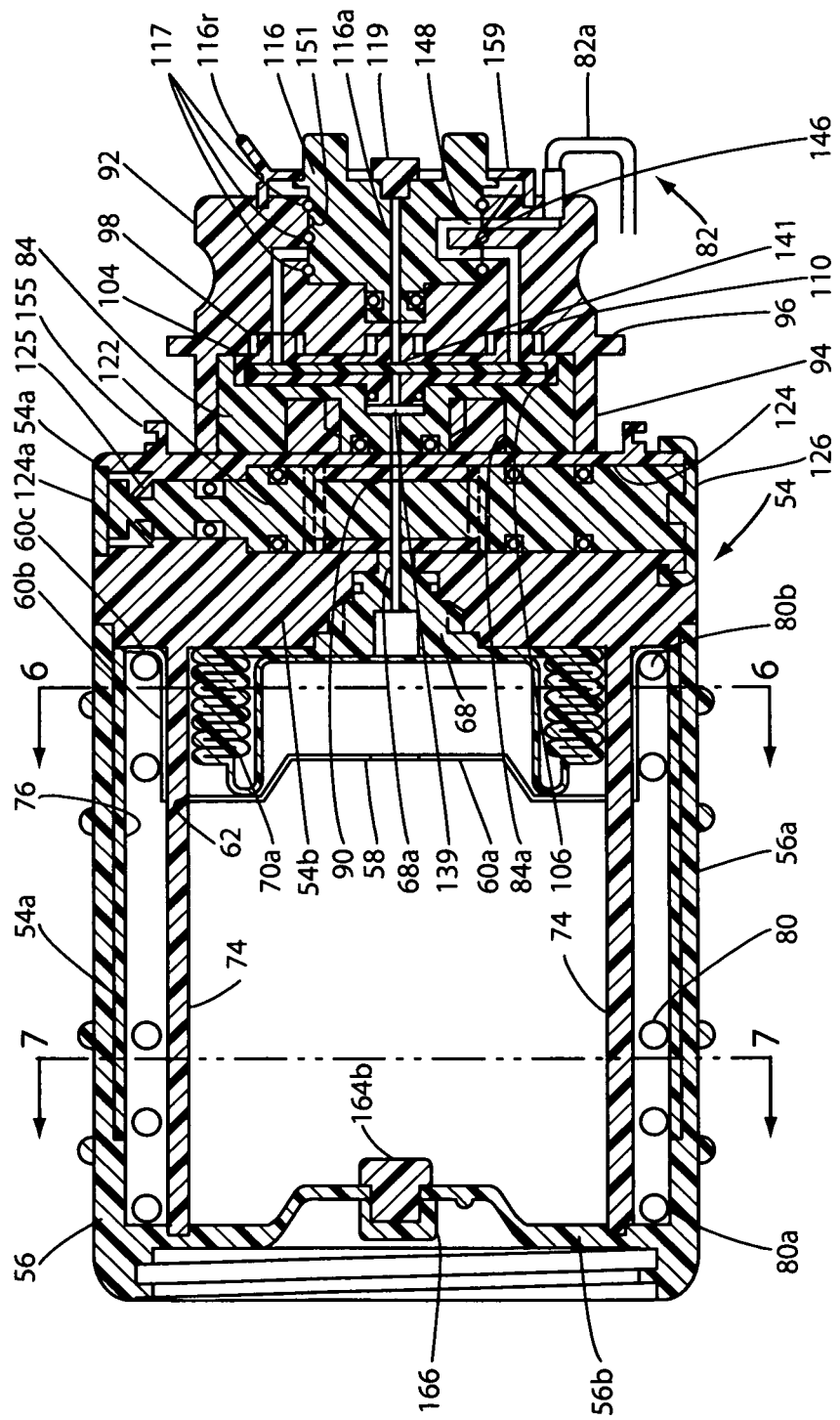
FIG. 5 is a longitudinal, cross-sectional view similar to FIG. 4, but showing the various components of the device as they appear following delivery to the patient of the fluid contained within the device reservoir.

Disposed within wall portion 56a is a carriage assembly 58, which is movable between a first position shown in FIG. 4 and a second position, shown in FIG. 5. As best seen by referring to FIGS. 4 and 7, carriage assembly 58 comprises a carriage 60 having a carriage base 60a that is provided with a plurality of circumferentially spaced openings 62 and a generally cylindrically shaped sidewall 60b which terminates in a radially outwardly extending flange 60c. Carriage assembly 58 is releasably locked in its first position by a novel locking means the character of which will presently be described.

Figures 9, 10, 11:
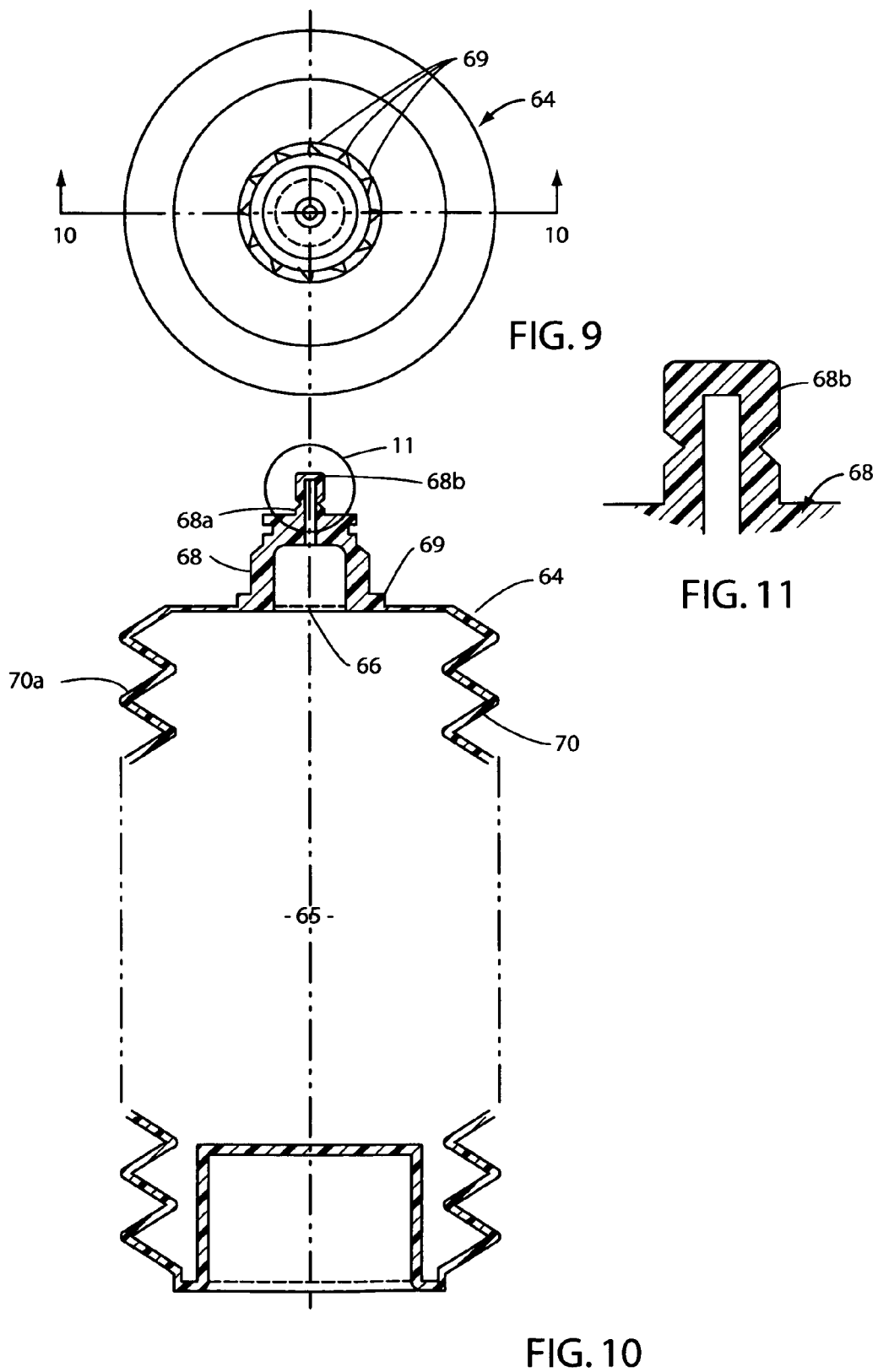
FIG. 9 is a top plan view of the fluid reservoir assembly of the invention.
FIG. 10 is a cross-sectional view taken along lines 10-10 of FIG. 9.
FIG. 11 is an enlarged cross-sectional view of the area designated in FIG. 10 by "11".
Figure 22:
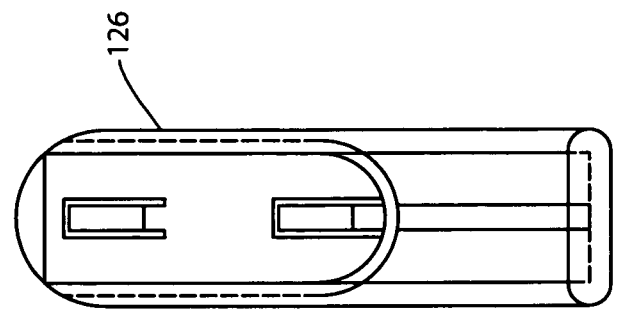
FIG. 22 is a view taken along lines 22-22 of FIG. 21.
Figure 21:
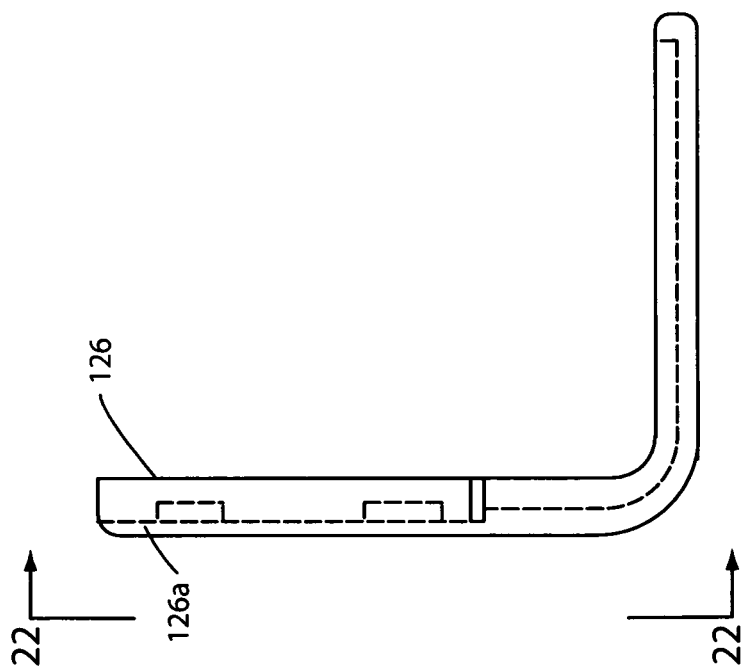
FIG. 21 is a top plan view of the operating handle of the device that is used for rotating the control shaft.
Figure 28:
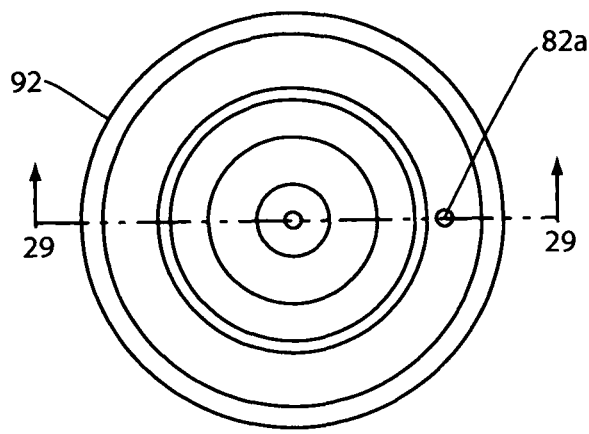
FIG. 28 is a top plan view of the selector member housing of the device.

Carried by carriage assembly 58 is a reservoir defining assembly 64 that defines a fluid reservoir 65. As indicated in FIG. 4, reservoir 65 has a combination inlet/outlet 66 that is formed in a shearable reservoir nipple 68b that comprises a part of the reservoir assembly 64. Nipple 68 is connected to an accordion-like member 70 that also comprises a part of the reservoir assembly 64 (FIGS. 4 and 10). Locking teeth 69 which circumscribe nipple 68 hold the assembly 64 in place. Reservoir assembly 64 can be constructed from low and high density polyethylene and polypropylene and like polymers.

In the preferred form of the invention, nipple 68 is sealably interconnected with member 70 in accordance with an aseptic blow-fill-seal technique. This technique involves the continuous extrusion through an extruder head of a length of parison in the form of a hollow tube between and through two co-acting first or main mold halves. The method includes the step of cutting off the parison below the extruder head and above the main mold halves to create an opening which allows a blowing and filling nozzle assembly to be moved downwardly into the opening in the parison for molding and thereafter filling a molded container.

When the container is filled with the desired amount of liquid, the blowing and filling nozzle assembly is retracted from the opening in the parison. A separate pair of co-acting second or upper sealing mold halves are then moved together around the exposed length of parison to form and seal the container upper portion. The finished container, completely formed, filled, and sealed as a unitary structure is then conveyed out of the apparatus. Reference should also be made to U.S. Pat. No. 6,145,285 issued to Anderson, which discloses an improved method and apparatus for molding containers using aseptic blow-fill-seal techniques. Further information concerning aseptic blow-fill-seal techniques is available from Weiler Engineering of Elgin, Ill.

Figure 6:
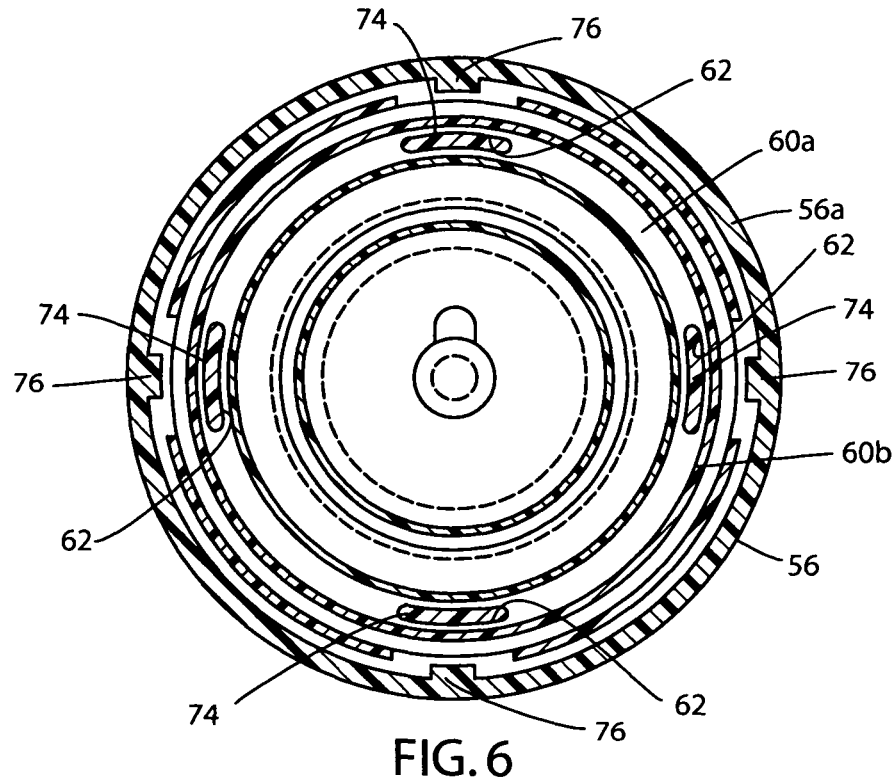
FIG. 6 is a cross-sectional view taken along lines 6-6 of FIG. 5.
Figure 7:
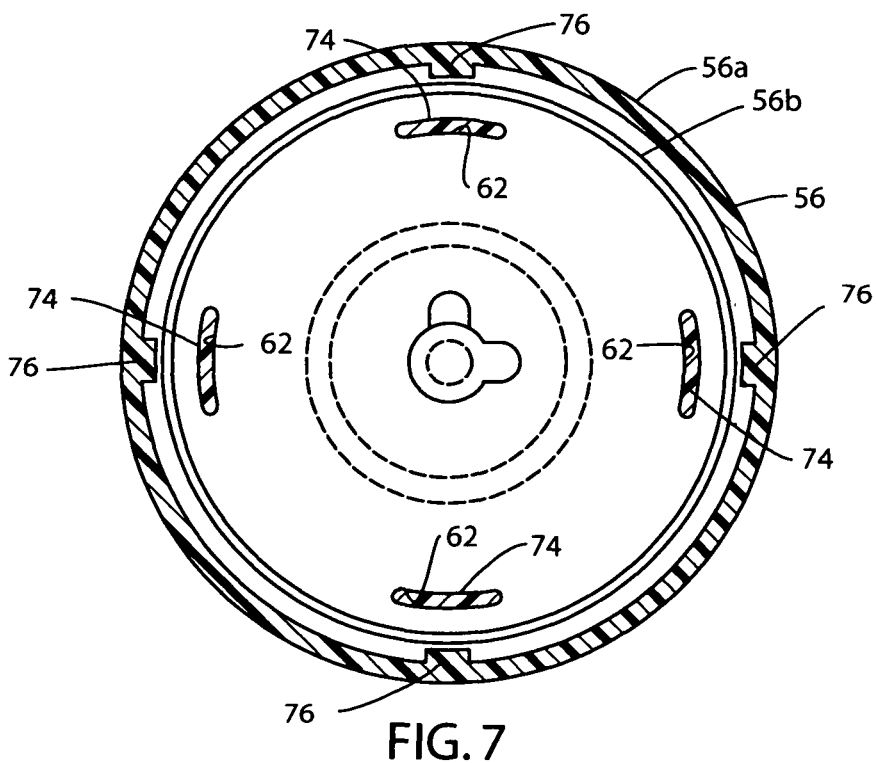
FIG. 7 is a cross-sectional view taken along lines 7-7 of FIG. 5.
Figure 8:
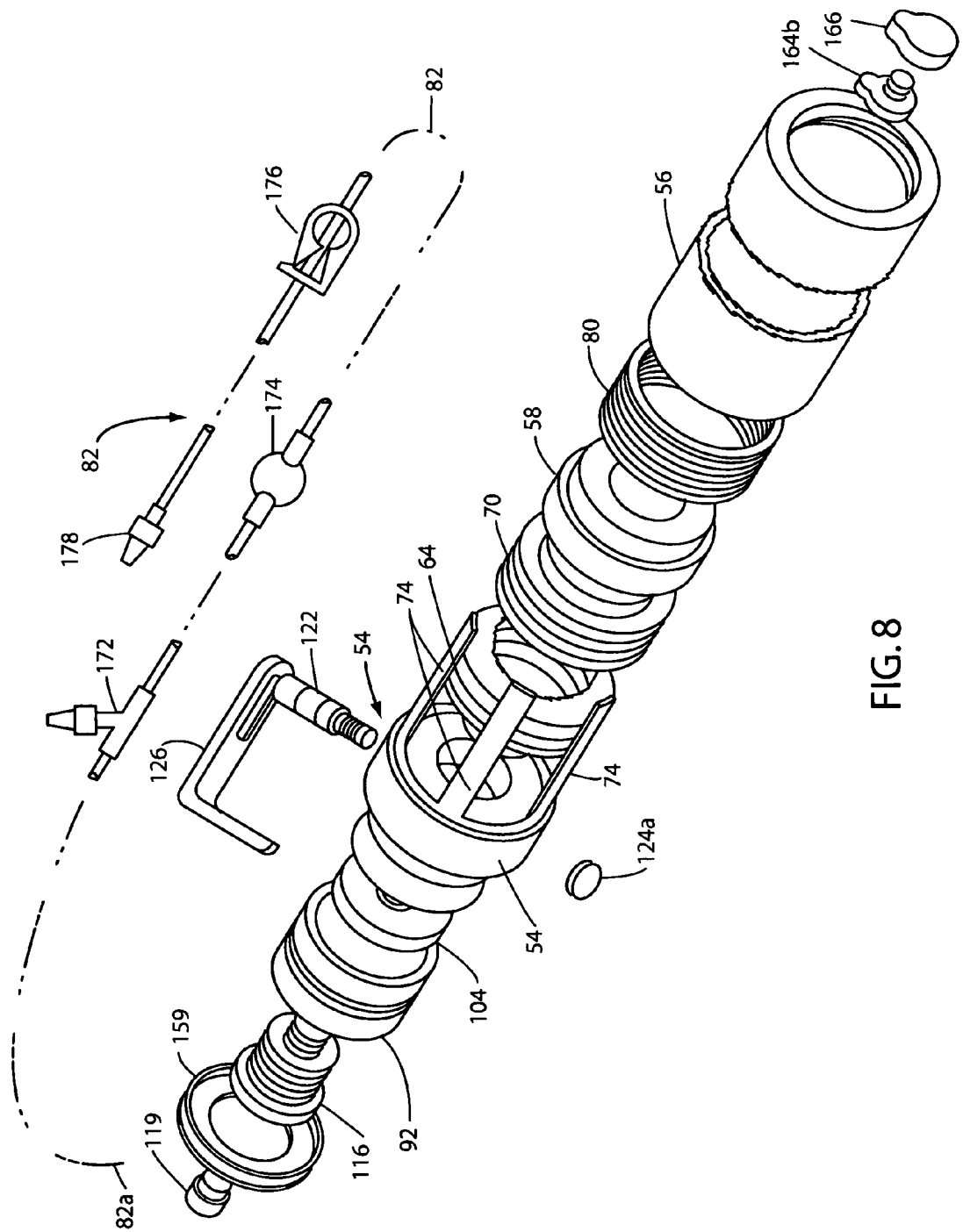
FIG. 8 is a generally perspective, exploded view of the fluid delivery device illustrated in FIG. 3.

An important feature of the present invention resides in the provision of novel guide means for guiding travel of carriage assembly 58 between the first position shown in FIG. 4 and the second position shown in FIG. 5. In the present form of the invention this important guide means comprises a plurality of circumferentially spaced guide members 74 which are connected to and extend outwardly from connector 54b of connector assembly 54 (FIGS. 4, 6 and 7). As indicated in the drawings, guide members 74 are slidably received within openings 62 provided in carriage base 60a so that as the carriage assembly travels from its first position toward its second position, guide members 74 precisely guide its travel. Also forming a part of the guide means of the apparatus of the present invention are a plurality of circumferentially spaced guide ribs 76 that are formed on the inner wall of outer housing 56 (FIGS. 6 and 7).

To controllably move the carriage assembly from its first position to its second position, novel stored energy means are provided. This novel stored energy means, which is operably associated with carriage assembly 58, is here provided in the form of a coiled compression spring 80. As illustrated in FIGS. 4 and 5, one end 80a of the coil spring 80 is disposed in engagement with the threaded base portion 56b of outer housing 56 of the supporting structure and the other end 80b thereof is disposed in engagement with radially outwardly extending flange 60c of carriage 60. With this construction, when the locking means of the invention is manipulated in a manner to unlock the carriage assembly from base portion 56b of the outer housing, spring 80 will move from its retracted position shown in FIG. 4 to its expanded position shown in FIG. 5, and in so doing will controllably move the carriage assembly 58 from its starting position shown in FIG. 4 to its fully deployed, or extended position shown in FIG. 5. As will be described more fully in the paragraphs which follow, as the carriage assembly moves toward its deployed position, the accordion sidewall 70a of the bellows member 70 will move into the collapsed configuration shown in FIG. 5 and in so doing will cause the medicinal fluid contained within the container to be controllably substantially expelled therefrom.

To further control the flow of medicinal fluid from reservoir 65 toward the administration set 82 of the invention and then on to the patient, flow control means are provided. This novel fluid flow control means, which is carried by connector assembly 54 of the supporting structure 52, here comprises two cooperating components, namely a rate control means for controlling the rate of fluid flow from the collapsible reservoir and an operating means for controlling fluid flow between the collapsible reservoir and the rate control means.

Figure 29:
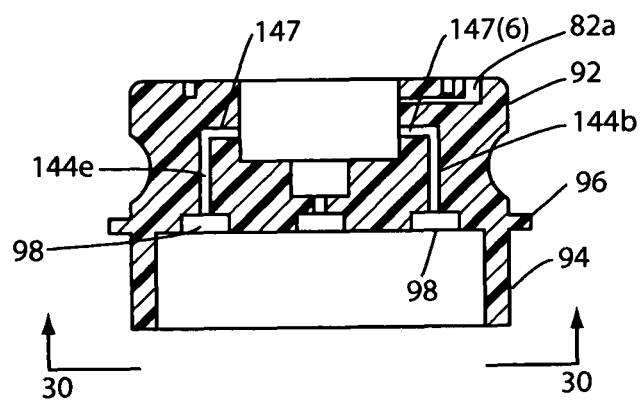
FIG. 29 is a cross-sectional view taken along lines 29-29 of FIG. 28.
Figure 30:
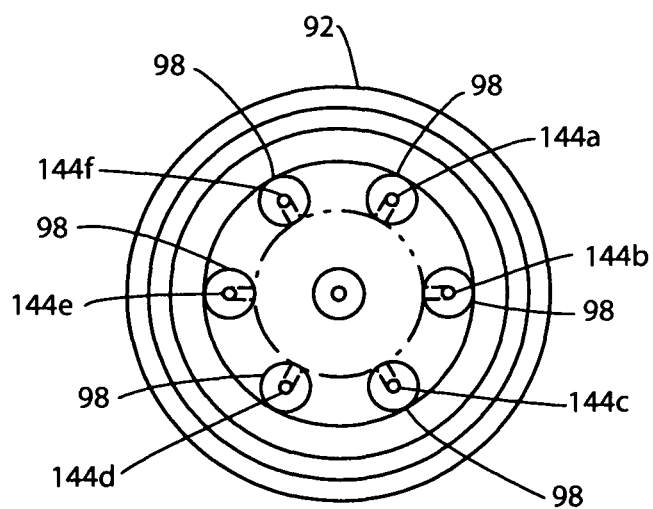
FIG. 30 is a view taken along lines 30-30 of FIG. 29.
Figure 31:
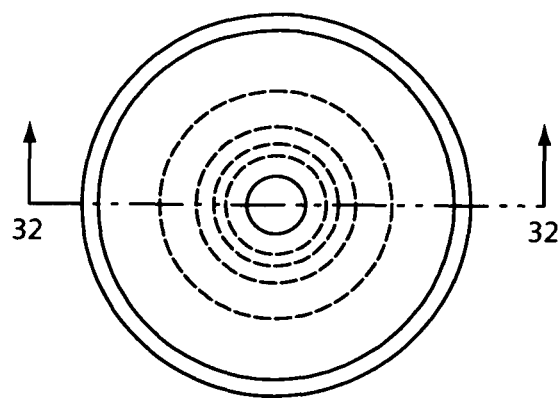
FIG. 31 is a top plan view of the rate control housing of the device which houses the rate control assembly.
Figure 32:
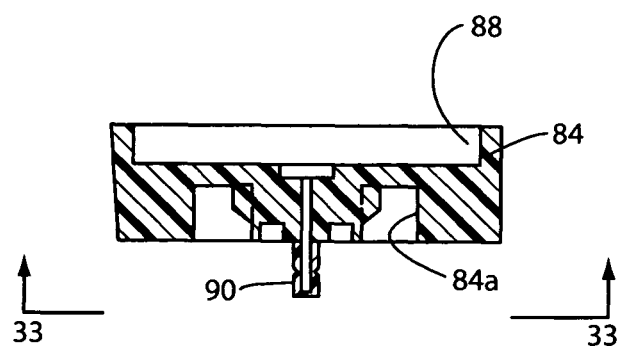
FIG. 32 is a cross-sectional view taken along lines 32-32 of FIG. 31.
Figure 33:
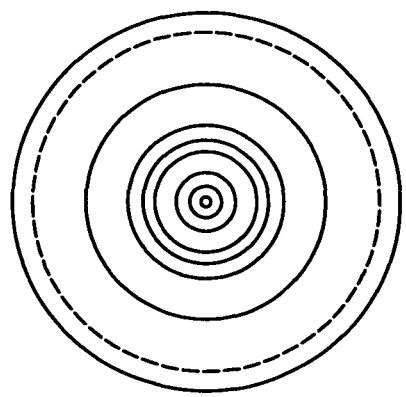
FIG. 33 is a view taken along lines 33-33 of FIG. 32.
Figure 38:
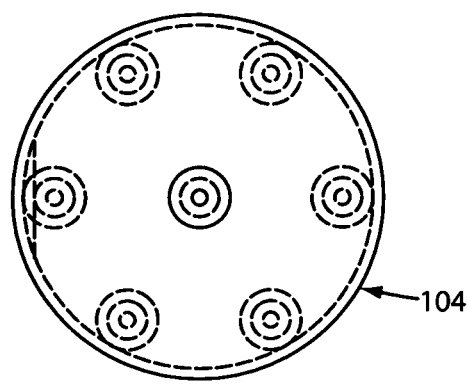
FIG. 38 is a view taken along lines 38-38 of FIG. 37.
Figure 36:
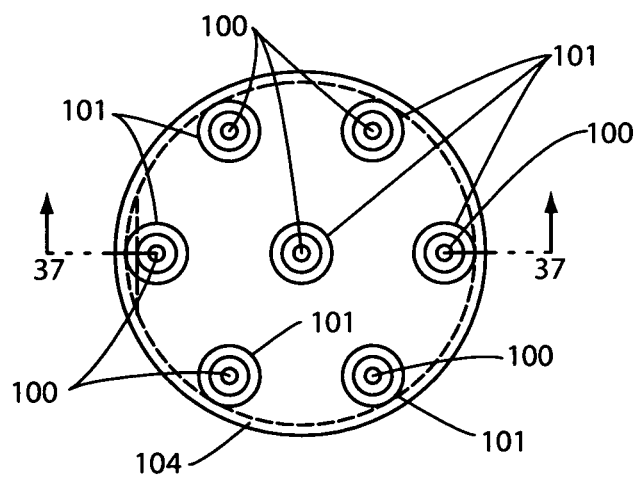
FIG. 36 is a top plan view of the rate control assembly of the present form of the invention.
Figure 37:
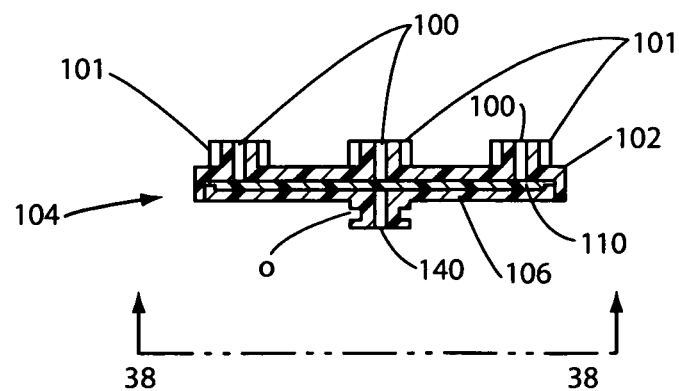
FIG. 37 is a cross-sectional view taken along lines 37-37 of FIG. 36.
Figure 39:
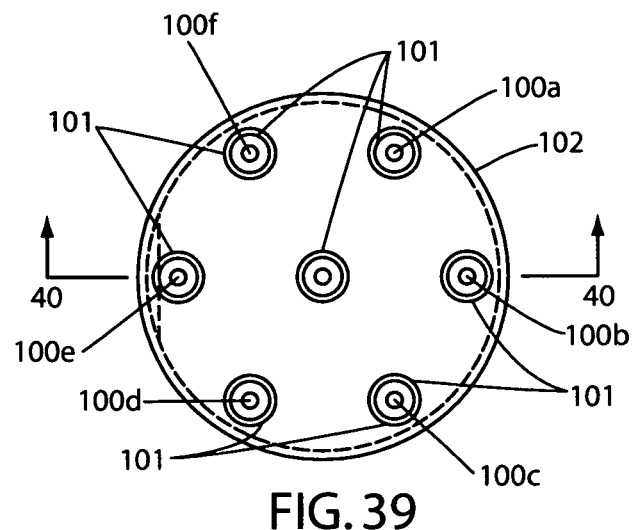
FIG. 39 is a top plan view of the upper cover of the rate control assembly shown in FIG. 36.
Figure 40:
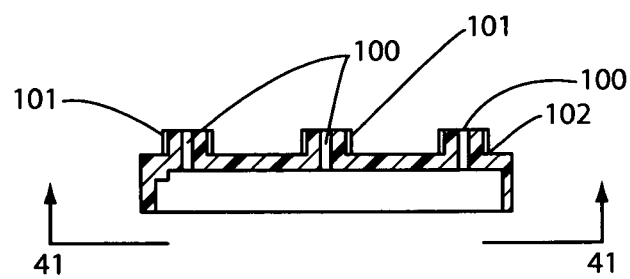
FIG. 40 has a cross-sectional view taken along lines 40-40 of FIG. 39.
Figure 41:
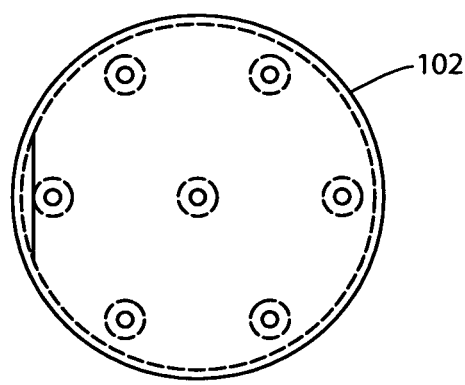
FIG. 41 is a view taken along lines 41-41 of FIG. 40.

Considering first the rate control means of the invention, which is illustrated in FIGS. 31 through 47, this important means comprises a rate control housing 84, which includes a generally annular-shaped cavity 84a (see FIGS. 5 and 32) that closely receives a collar 86 formed on connector 54a of connector assembly 54 (see also FIG. 35). As best seen in FIG. 32, rate control housing 84 includes a rate control cavity 88 and an outwardly extending, shearable nipple 90, the purpose of which will presently be described. Interconnected with a rate control housing 84 is a selector member housing 92, that includes a skirt 94 that circumscribes rate control housing 84 (FIGS. 4 and 29). Selector member housing 92 also includes an outwardly extending flange 96 which defines a cylindrical space about which the administration line 82a of the administration set can be coiled in the manner best seen in FIG. 4. Additionally, selector member housing 92 is provided with a plurality of circumferentially spaced cavities (FIGS. 29 and 30), which are adapted to sealably receive circumferentially spaced-apart outlet ports 100 that are formed on rate control cover 102 of the rate control assembly 104 of the present invention (see FIGS. 36 and 37). In order to ensure a positive seal, the outlet ports 100 are provided with elastomeric collars 101 which are sealably received around the circumferentially spaced-apart outlet ports 100.

As illustrated in FIG. 4, rate control assembly 104, which forms a part of the rate control means of the invention, is closely received within rate control cavity 88 and is held in position therewithin by rate control housing 84. In addition to rate control cover 102, rate control assembly 104 includes a second, mating rate control cover 106 and a novel rate control plate 110 (FIG. 42), that is disposed between covers 102 and 106. As will presently be described, rate control plate 110 can be constructed from a variety of plastic materials and is provided with a plurality of fluid flow channels 112 of different lengths, widths, depths and geometry that are in fluid communication with outlet 66 of collapsible reservoir 65.

As previously discussed, the rate control means of the invention includes selector means for selecting the rate of fluid flow between collapsible reservoir 65 and the administration set 82 of the invention. In addition to the previously identified selector member housing 92, the selector means includes a selector member 116 that is held in position by a retainer member 159, and is rotatably carried by the selector housing (FIG. 4). A plurality of O-rings 117 which circumscribe the body portion of selector member 116, provide a substantially leak-tight seal between the components. Selector member 116 carries a pierceable drug recovery septum 119, which forms a part of the recapture means of the invention and includes an axially extending fluid passageway 116a, that provides fluid communication between septum 119 and the fluid reservoir via rate control assembly 104 and frangible nipple 90. As will be discussed in the paragraphs which follow, selector member 116 is also provided with a plurality of circumferentially extending passageways that communicate with the rate control passageways formed in rate control plate 110 via fluid passageways formed in selector member housing 92 (see FIG. 47A).

Considering next the previously identified operating means of the invention, which is illustrated in FIGS. 12 through 20, this important operating means, which controls fluid flow between collapsible reservoir 64 and the rate control means, here comprises an operating shaft 122 that is rotatably mounted within a generally cylindrically shaped chamber 124 formed in connector 54 of supporting structure 52. Operating shaft 122 can be rotated within chamber 124, which is closed by a cap 124a, by an "L"-shaped operating handle 126 (FIG. 3) between a first position shown in FIG. 18 blocking fluid flow from collapsible reservoir 64 toward administration set 82 and a second position shown in FIG. 20 permitting fluid flow from the reservoir toward the administration set.

Turning particularly to FIGS. 12 and 15, operating shaft 122 can be seen to comprise a body portion 122a and a reduced diameter neck portion 122b. Circumferentially spaced-apart, generally arcuate-shaped cavities 130 and 132, which are formed in body portion 122a, are strategically located to receive the end portions of nipples 68 and 90 when the operating shaft is in held in position within chamber 124 by retainer clips 125 in the manner shown in FIG. 4. Also formed within operating shaft 122 is a transversely extending fluid passageway 134, which, upon rotation of the operating shaft by handle 126, can be moved into alignment with the fluid passageways 68a and 90a of nipples 68 and 90 respectively (see FIG. 20).

Mounted within each of the cavities 130 and 132 is a spring knife 136 which, as indicated in FIGS. 16 and 17, includes a cutting edge 136a formed proximate one extremity and a pair of mounting clips 137 provided proximate the opposite extremity. Tabs 137a of the mounting clips are received within slots 139 formed in body portion 122a so as to secure the spring knives within the arcuate cavities in the manner illustrated in FIG. 15. With this construction, as the operating shaft 122 is rotated by handle 126 from the position shown in FIG. 18 into the position shown in FIG. 19 the spring knives will cleanly sever the sealed tip portions 68b and 90b of the frangible, shearable nipples 68 and 90 respectively. Continued rotation of operating member 122 will move sealed tip portions 68b and 90b into the cavities for rotation therewith (FIG. 19) and will move transverse passageway 134 into alignment with passageways 68a and 90a in a manner shown in FIG. 20. With the operating member in this position fluid can flow freely from reservoir 65 toward the rate control means of the invention via passageways 68a and 90a of nipples 68 and 90.

Figure 42:
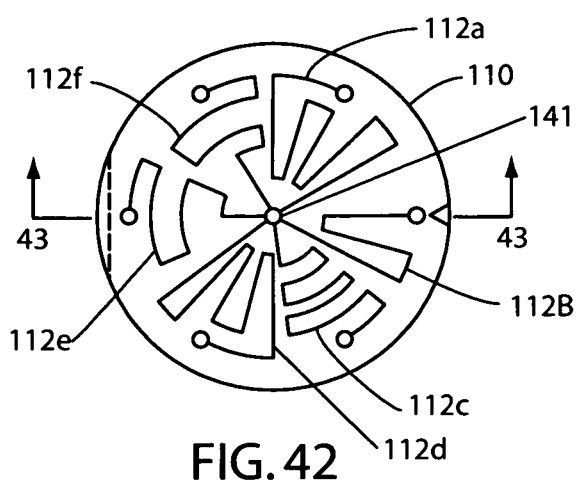
FIG. 42 is a top plan view of one form of the rate control plate of the rate control assembly of the invention.
Figure 43:
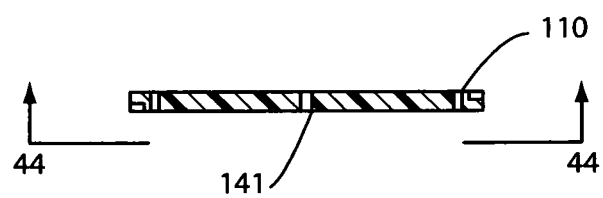
FIG. 43 is a cross-sectional view taken along lines 43-43 of FIG. 42.
Figure 44:
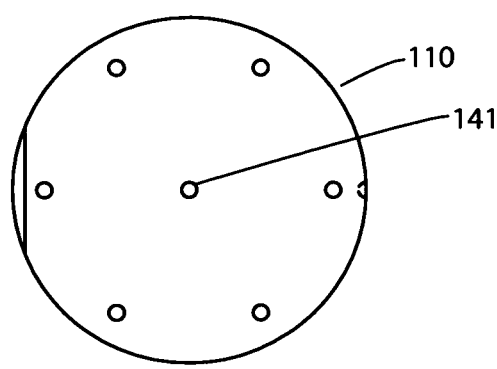
FIG. 44 is a view taken along lines 44-44 of FIG. 43.
Figure 45:
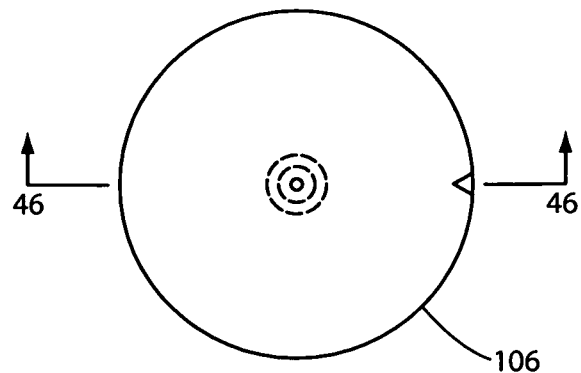
FIG. 45 is a top plan view of the bottom cover of the rate control assembly of the invention.
Figure 46:
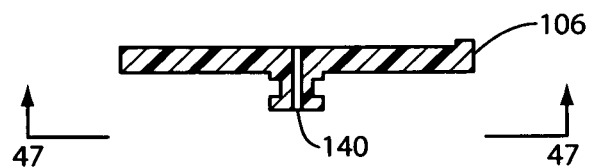
FIG. 46 is a cross-sectional view taken along lines 46-46 of FIG. 45.
Figure 47:
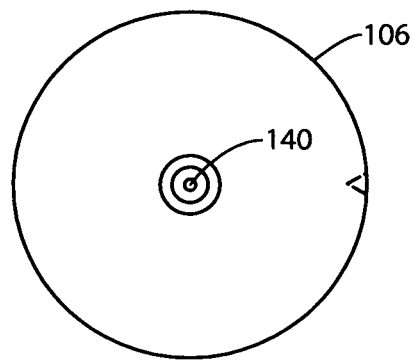
FIG. 47 is a view taken along lines 47-47 of FIG. 46.
Figure 47A:
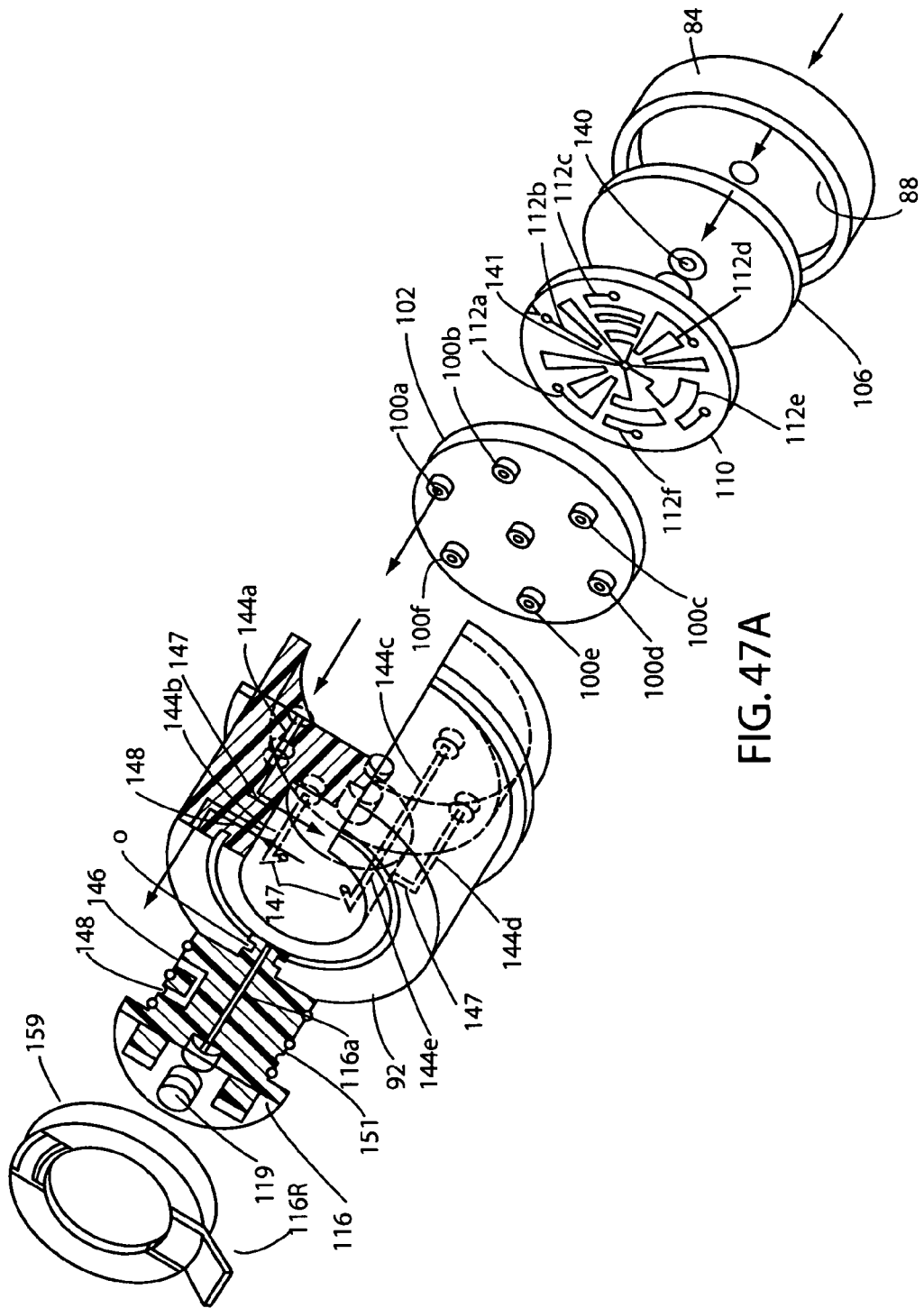
FIG. 47A is an exploded, generally perspective, diagrammatic view of rate control portion of the device of the invention illustrating the manner of fluid flow from the device reservoir toward the administration set of the invention.

From passageway 90a fluid will flow through a conventional particulate filter 139, into inlet 140 of rate control cover 106 of the rate control assembly 104, into inlet 141 of rate control plate 110 and then into the various circuitous fluid channels 112a, 112b, 112c, 112d, 112e and 112f formed in the rate control plate, each of which may be of a different length, width, depth and geometry (see FIGS. 42 and 47A). As each of the channels fills with the medicinal fluid to be dispensed to the patient, the fluid will flow into outlet passageways 100a, 100b, 100c, 100d, 100e and 100f respectively formed in rate control cover 102. From these outlet passageways, the fluid flows into and fills circumferentially spaced-apart fluid passageways 144a, 144b, 144c, 144d, 144e and 144f formed in selector housing 92 (see FIG. 30).

As best seen by referring to FIG. 24, selector member 116 is provided with an inlet passageway 146 and an outlet passageway 148 that is interconnected with inlet passageway 146 by means of an axially extending stub passageway 150 which, in turn, is connected to a circumferentially extending passageway 151 formed in selector member 116 (FIG. 47A). With this construction, by rotating the selector member 116, inlet passageway 146 can be selectively brought into index with one of the radial extensions 147 of the axially extending passageways formed in selector member 92 thereby providing fluid communication between outlet passageway 148 and the selected one of the circuitous flow passageways formed in rate control plate 110 via annular passageway 151 and the selected axially extending passageway formed in the selector housing 92. Since outlet passageway 148 is in fluid communication with the administration set 82 of the invention via passageway 151, the rate of fluid flow toward the patient can be precisely controlled by selecting a rate control passageway of appropriate length that is formed in rate control plate 110.

With the device in the configuration shown in FIGS. 1, 2 and 4, and with the fluid reservoir 65 filled with the medicament to be dispensed to the patient, the dispensing operation can be commenced by removing the top cover 153, which is snapped over a cover connector 155 that protrudes from the structural member 54a. With the cover removed, the administration line 82a of the administration set 82 can be unwrapped from the selector member housing, about which it has been coiled (see FIGS. 3 and 4). Removal of the top cover 153 also exposes the selector member 116 so that the fluid flow rate can be selected by actioning the interlock 116r and rotating the selector member to the desired flow rate indicated by the indicia 157 imprinted on the selector member component 116. With the desired flow rate thusly set, the operating shaft 122 is next rotated through the use of the operating handle 126 from the starting position shown in FIG. 18 to the fully rotated position shown in FIG. 20. In this way, communication is opened between the reservoir outlet 66 and passageway 90a of nipple 90 which, in turn, is in communication with the rate control assembly of the invention.

Figure 48:
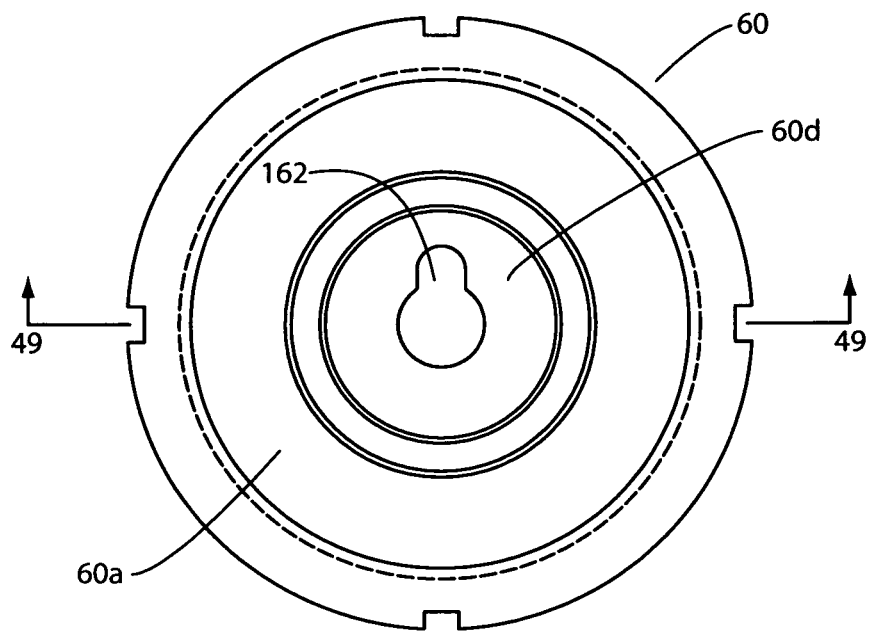
FIG. 48 is a top plan view of the carriage component of the device of the invention which supports the reservoir assembly.
Figure 49:
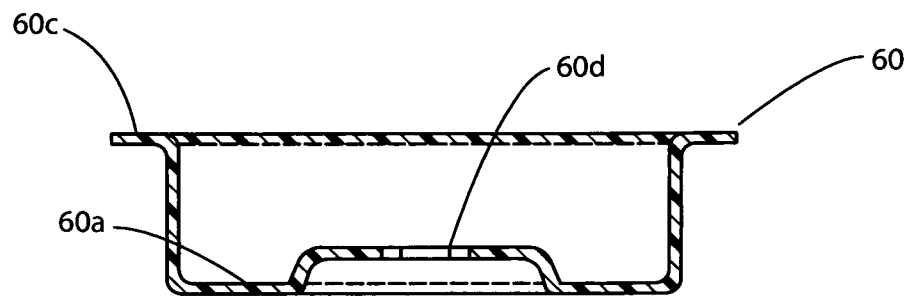
FIG. 49 is a cross-sectional view taken along lines 49-49 of FIG. 48.
Figure 50:
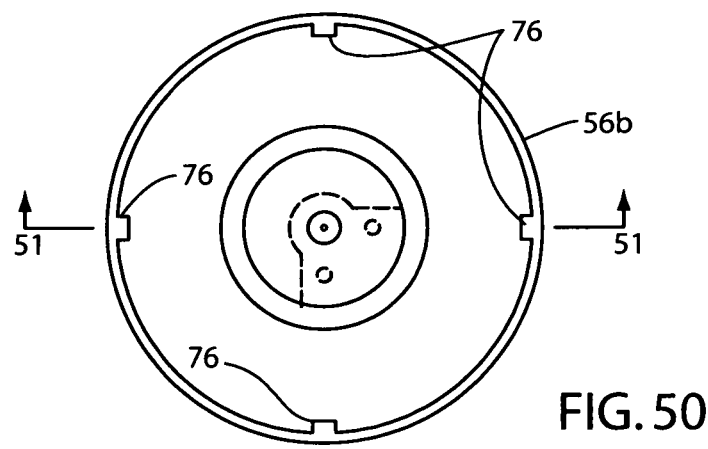
FIG. 50 is a top plan view of a portion of the structural support of the device of the invention which supports the carriage component shown in FIGS. 48 and 49.
Figure 51:
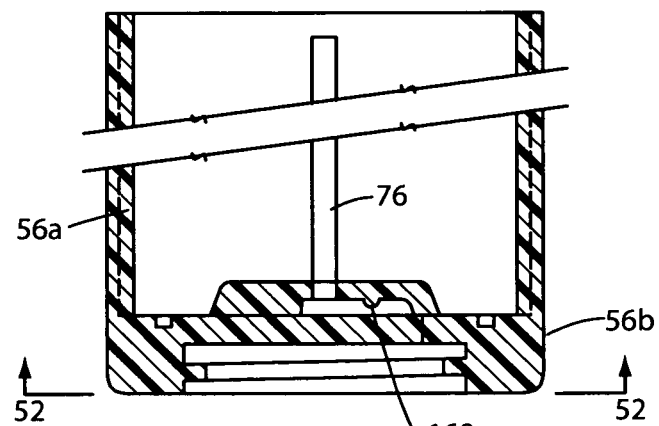
FIG. 51 is a foreshortened, cross-sectional view taken along lines 51-51 of FIG. 50.
Figure 52:
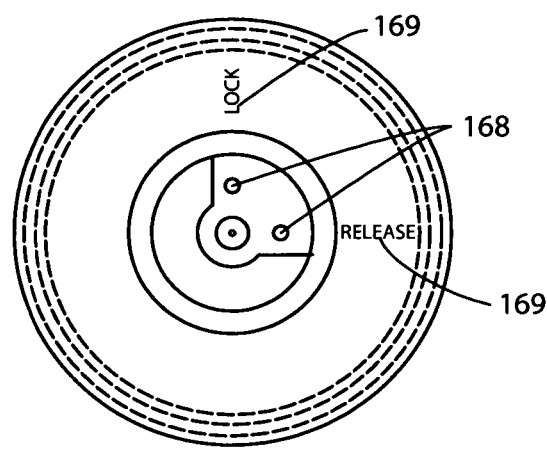
FIG. 52 is a view taken along lines 52-52 of FIG. 51.
Figure 54:
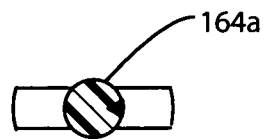
FIG. 54 is a view taken along lines 54-54 of FIG. 53.
Figure 53:
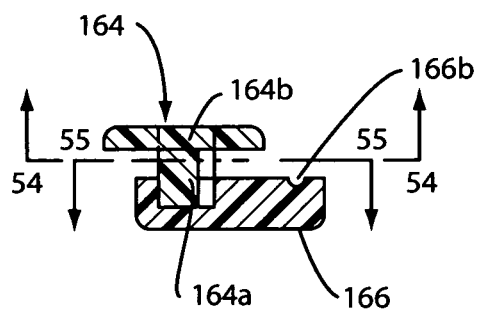
FIG. 53 is cross-sectional view of the locking means of the invention for releasably locking the carriage to the portion of the structural support shown in FIGS. 50 and 51.
Figure 55:
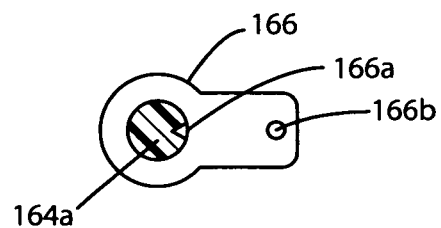
FIG. 55 is a view taken along lines 55-55 of FIG. 53.

Following the controlled rotation of the operating shaft 122, which is interconnected with structural member 54a, the carriage locking means of the invention can be manipulated in a manner to release the carriage 60 from base member 56b in order to permit the stored energy means, or spring 80, to move the carriage from the starting position shown in FIG. 4 to the extended position shown in FIG. 5. In this regard, as best seen in FIGS. 53 and 55, the carriage locking means includes a locking member 164 having a shank portion 164a which extends through a keyhole-shaped opening 162 provided in the carriage base (see FIG. 48) and a generally keyhole-shaped locking portion 164b. The carriage locking means also includes a finger-engaging, operating member 166 that includes a driving rib 166a that is received within a groove formed within shaft 164a. Operating member 166 functions to rotate locking member 164 from a transverse locking position to a release position in alignment with keyhole opening 162 formed in carriage base 60d. As indicated in FIGS. 51 and 52 base 56b of the supporting structure is provided with circumferentially spaced-apart indexing buttons 168 which are received within a button receiving cavity 166b formed in finger-engaging member 166 as the operating member is rotated from a locked position to a release position (FIG. 53). As shown in FIG. 52, to assist the caregiver in performing the carriage release step, base 56b is provided with indicia 169 indicating the locking and release position of the operating member 166.

Following the release of the carriage assembly, the stored energy means, or coiled spring 80, will move the carriage from a position shown in FIG. 4 into the position shown in FIG. 5 and in so doing will urge the fluid contained within reservoir 65 to flow toward reservoir outlet 66, into passageway 134 formed in control member 122 and into passageway 90a of nipple 90. From passageway 90a, fluid will flow into inlet 140 of rate control cover 106 of the rate of control assembly 104, into inlet 141 of rate control plate 110 and then into the various circuitous fluid channels 112a, 112b, 112c, 112d, 112e and 112f formed in the rate control plate. As each of the channels fills with the medicinal fluid to be dispensed to the patient, the fluid will flow into outlet passageways 100a, 100b, 100c, 100d, 100e and 100f respectively formed in rate control cover 102. From these outlet passageways, the fluid will flow into and fill the circumferentially spaced-apart fluid passageways 144a, 144b, 144c, 144d, 144e and 144f formed in selector housing 92 (see FIG. 30).

As previously discussed, by rotating the selector member 116, inlet passageway 146 of selector member 116 can be selectively brought into index with one of the radial extensions 147 of the passageways formed in selector member housing 92 thereby providing fluid communication between outlet passageway 148 and the selected one of the circuitous flow passageways 112 (see FIGS. 24 and 29) formed in rate control plate 110. Since outlet passageway 148 is in fluid communication with the administration set 82 of the invention via passageway 151, the rate of fluid flow toward the patient can be precisely controlled by selecting a rate control passageway of appropriate length that is formed in rate control plate 110 (see FIG. 47A).

In the present form of the invention, administration set 82, which comprises a part of the dispensing means of the invention for delivering medicinal fluids to the patient, includes, in addition to administration line 82a, a conventional "Y"-site injection septum or port 172, a conventional gas vent and particulate filter 174 and a line clamp 176. Provided at the distal end of the administration line is a luer connector 178 of conventional construction (FIG. 3) which enables the device to be interconnected with the patient in a conventional manner.

In those special instances where reservoir 65 has not been filled with the medicament at the time of manufacture, the reservoir can be expeditiously filled in the field by a relatively simple procedure. More particularly, after rotating the control shaft in the manner previously described and to sever the sealed tip portions of the nipples 70 and 90, the medicament to be delivered to the patient can be transferred from a conventional syringe or the like to reservoir 65 via pierceable drug recovery septum 119, fluid passageway 116a, rate control assembly 104 and passageways 90a and 70a of nipples 90 and 70 (see FIGS. 5 and 47A).

Using a conventional syringe, or like device, pierceable septum 119 can also be used to recover any medicament that may remain in reservoir 65 following the fluid delivery step.

Turning now to FIGS. 56 through 62, an alternate form of the dispensing device of the present invention for dispensing medicaments to a patient is there shown and generally designated by the numeral 200. This alternate form of dispensing device is similar in many respects to that shown in FIGS. 1 through 55 and like numerals are used in FIGS. 56 through 62 to identify like components. As before, the dispensing device here includes a supporting structure 52 which includes a connector assembly 54 and a generally cylindrically shaped outer housing 56 that is interconnected with the connector assembly in the manner best seen in FIG. 56 of the drawings.

Figure 56:
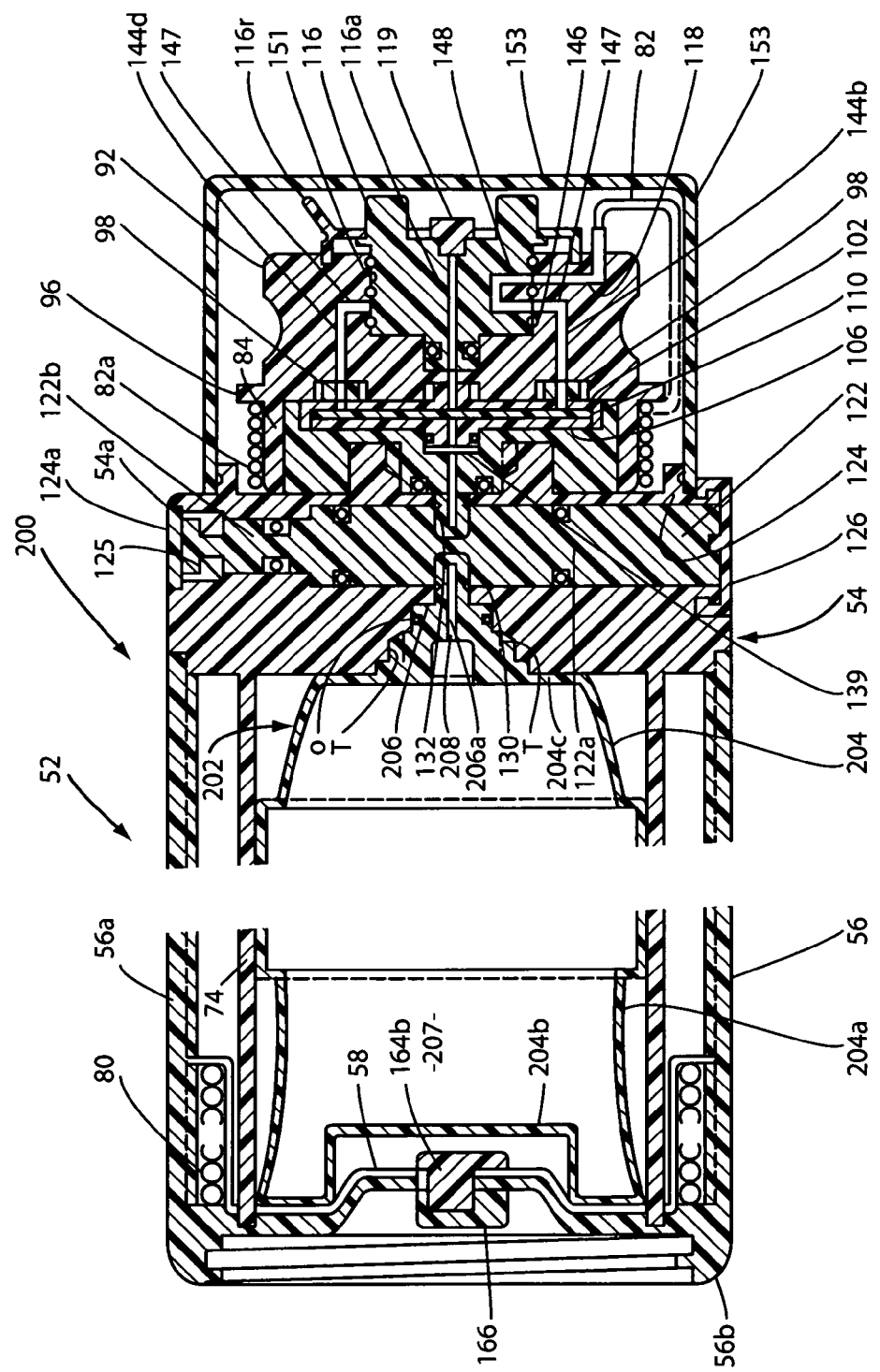
FIG. 56 is an enlarged, foreshortened, longitudinal, cross-sectional view of an alternate form of the fluid dispensing device of the invention.
Figure 57:
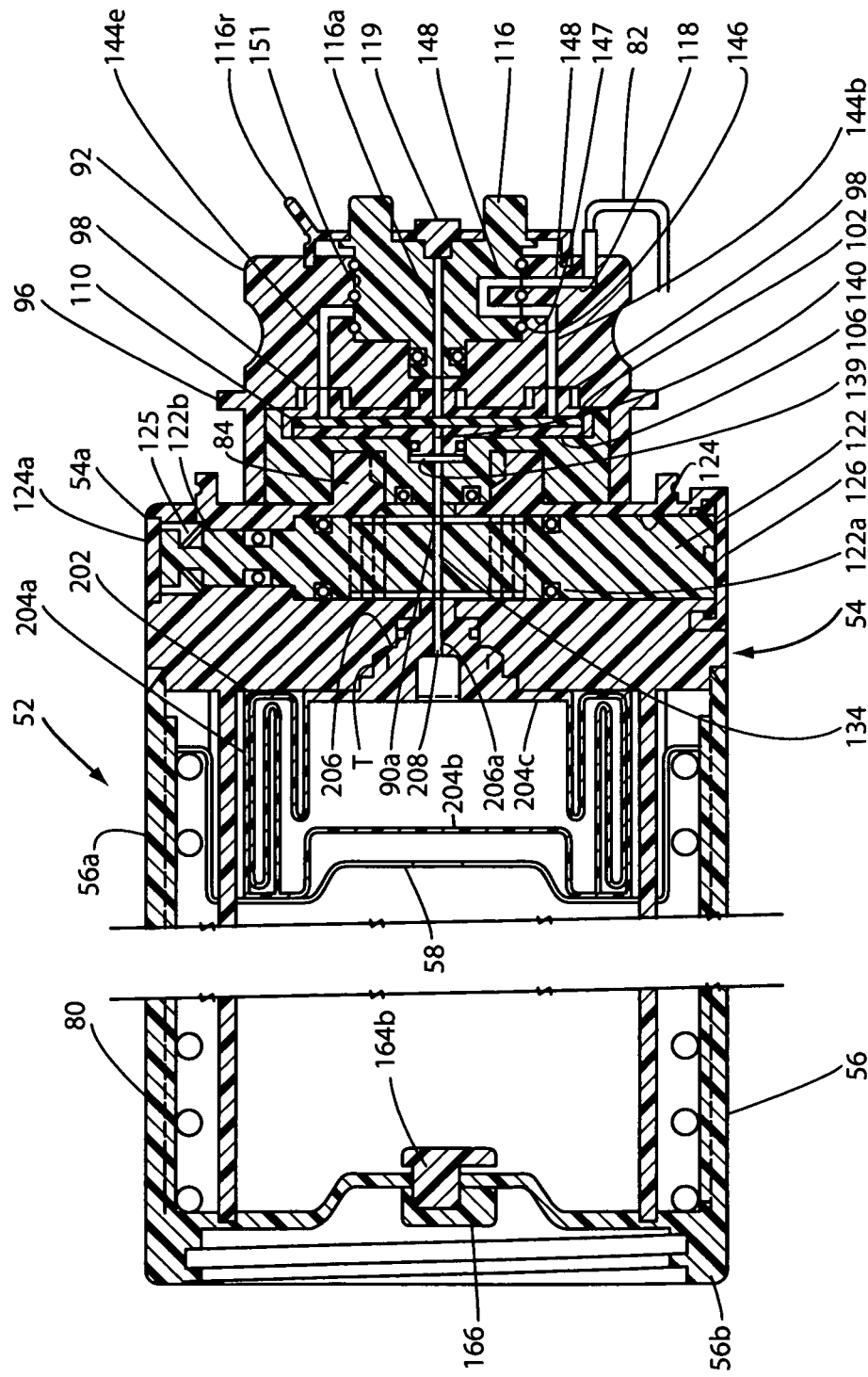
FIG. 57 is a longitudinal, cross-sectional view similar to FIG. 56, but showing the various components of the device as they appear following delivery to the patient of the fluid contained within the device reservoir.
Figure 62:
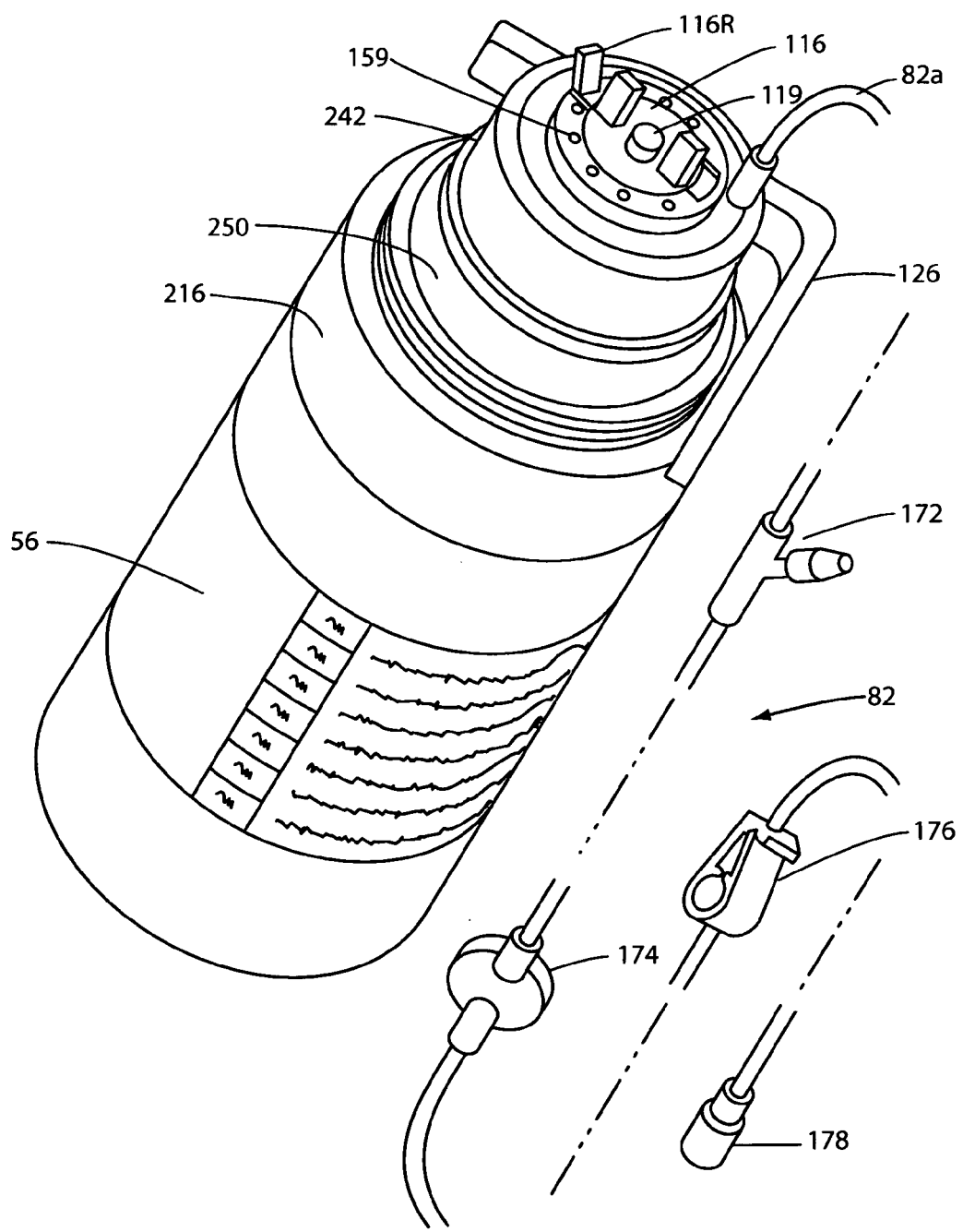
FIG. 62 is a generally perspective view of this alternate embodiment of the invention as it appears with the top cover of the device removed.

Disposed within wall portion 56a is a carriage assembly 58 which is movable between a first position shown in FIG. 56 and a second position shown in FIG. 57. Carriage assembly 58 is of identical construction and operation to that previously described and is releasably locked in its first position by locking means also identical to the locking means previously described herein.

The primary difference between this latest form of dispensing device of the invention and that previously described resides in the provision of a reservoir defining assembly 202 of a totally different construction. Reservoir defining assembly 202 here comprises a collapsible container assembly 204 which is carried by carriage assembly 58 in the manner illustrated in FIG. 56.

As best seen by referring to FIGS. 58 through 61, collapsible container assembly 204 includes a collapsible, telescoping sidewall 204a, an interconnected bottom wall 204b and an interconnected top wall 204c to which a sealed reservoir nipple 206 is integrally formed and sealably interconnected. Collapsible container assembly 204 defines a fluid reservoir 207 having an inlet/outlet that is generally identified by the numeral 208.

In the preferred form of this alternate embodiment of the invention, shearable nipple 206 is integrally formed and sealably interconnected with member top wall 204c in accordance with an aseptic blow-fill-seal technique of the general character previously described to form a unitary structure.

As in the earlier described embodiment of the invention, an important feature of this latest form of the invention resides in the provision of novel guide means for guiding travel of carnage assembly 58 between the first position shown in FIG. 56 and the second position shown in FIG. 57. This important guide means is of identical construction and operation to that previously described herein.

To controllably move the carriage assembly from its first position to its second position, novel stored energy means are provided. This novel stored energy means, which is operably associated with carriage assembly 58, is here provided in the form of a coiled spring 80 which is also identical in construction and operation to that previously described.

As in the earlier described embodiment of the invention, when the locking means of the invention is manipulated in a manner to unlock the carriage assembly from base portion 56*b* of the outer housing, spring 80 will move from its compressed position shown in FIG. 56 to its expanded position shown in FIG. 57 and in so doing will controllably move the carriage assembly from its starting position shown in FIG. 56 to its fully deployed, or extended, position shown in FIG. 57. As the carriage assembly moves toward its deployed position, the collapsible sidewall 204*a* of the collapsible container 204 will move into the collapsed configuration shown in FIGS. 57 and 60. As the collapsible container collapses, the sidewalls will telescope and the medicinal fluid contained within the container will be controllably expelled therefrom.

To further control the flow of medicinal fluid from reservoir 207 toward the administration set 82 of the invention and then on to the patient, flow control means are provided. This novel fluid flow control means, which is identical in construction and operation to that previously described, comprises two cooperating components, namely a rate control means for controlling the rate of fluid flow from the collapsible reservoir and an operating means for controlling fluid flow between the collapsible reservoir and the rate control means. These important components are fully described in the preceding paragraphs.

As in the earlier described embodiment of the invention, the important operating means, which controls fluid flow between collapsible reservoir 207 and the rate control means, here comprises an operating shaft 122 that is rotatably mounted within a generally cylindrically shaped chamber 124 formed in connector 54*a* of supporting structure 52. As before, operating shaft 122 can be rotated within chamber 124 by an "L"-shaped operating handle 126 between a first position blocking fluid flow from collapsible reservoir 207 toward administration set 82 and a second position permitting fluid flow from the reservoir toward the administration set.

As illustrated in FIG. 56, operating shaft 122 includes a body portion 122*a* and a reduced diameter neck portion 122*b*. Circumferentially spaced-apart generally arcuate-shaped cavities 130 and 132, which are formed in body portion 122*a*, are strategically located to receive the end portions of nipples 206 and 90 when the operating shaft is in held in position within chamber 124 by retainer clips 125 in the manner shown in FIG. 56. Also formed within operating shaft 122 is a transversely extending fluid passageway 134 which, upon rotation of the operating shaft by handle 126, can be moved into alignment with the fluid passageways 206*a* and 90*a* of nipples 206 and 90 respectively.

Mounted within each of the cavities 130 and 132 is a spring knife 136, which includes a cutting edge formed proximate one extremity and a pair of mounting clips provided proximate the opposite extremity. As the operating shaft 122 is rotated by the operating handle 126 from it first position into its second position the spring knives will cleanly sever or shear the sealed tip portions 206*b* and 90*b* of nipples 206 and 90 respectively. Continued rotation of operating member will move sealed tip portions 206*b* and 90*b* into the cavities for rotation therewith and will move transverse passageway 134 into alignment with passageways 206*a* and 90*a*. With the operating member in this position fluid can flow freely from reservoir 207 toward the rate control means of the invention via passageways 206*a* and 90*a* of nipples 206 and 90.

From passageway 206*a*, fluid will flow through a conventional particulate filter 139, into inlet 140 of rate control cover 106 of the rate of control assembly 104, into inlet 141 of rate control plate 110 and then into the various circuitous fluid channels of the rate control plate in the manner previously described. The fluid will then flow into the circumferentially spaced-apart fluid passageways formed in the selector housing 92 via rate control cover 102. In operating the device in the manner previously described herein, by rotating the selector member 116, inlet passageway 146 can be selectively brought into index with one of the radial extensions 147 of the axially extending passageways formed in selector member 92, thereby providing fluid communication between outlet passageway 148 and the selected one of the circuitous flow passageways formed in rate control plate 110 via annular passageway 151 and the selected axially extending passageway formed in the selector member housing 92. Since outlet passageway 148 is in fluid communication with the administration set 82 of the invention via the annular grove and passageway 151, the rate of fluid flow toward the patient can be precisely controlled by selecting a rate control passageway of appropriate length, width, depth and geometry that is formed in rate control plate 110.

As before, by using a conventional syringe, or like device, pierceable elastomeric septum 119 can be used to recover any medicament that may remain in reservoir 207 following the fluid delivery step.

Referring next to FIGS. 63 through 76, still another form of the dispensing device of the present invention for dispensing medicaments to a patient is there shown and generally designated by the numeral 212. This alternate form of dispensing device is similar in some respects to that shown in FIGS. 56 through 62 and like numerals are used in FIGS. 63 through 75 to identify like components. Because the flow control means of this latest form of the invention is of different construction and operates in a different way, the dispensing device 212 includes a supporting structure 214, which, is of necessity, somewhat different in construction. More particularly, the supporting structure 214 here comprises a connector assembly 216 and a generally cylindrically shaped outer housing 218 that is interconnected with the connector assembly in the manner best seen in FIG. 63 of the drawings.

Disposed within outer housing 218 is the carriage assembly 58, which is of identical construction and operation to that previously described and is releasably locked in its first position by locking means also identical in construction and operation to the locking means previously described herein. Carried by carriage assembly 58 is a reservoir defining assembly 222, which is of similar construction to reservoir assembly 204 and here includes a collapsible container assembly 224 made from a blow-fill process (as distinguished from a blow-fill-seal process) having a sidewall 224*a*, an interconnected bottom wall 224*b* and an interconnected top wall 224*c* to which the accessing means of the invention for accessing the reservoir of the container assembly. This novel accessing means is here shown as a sealed reservoir insert septum assembly 226 is sealably interconnected (see FIG. 67). Collapsible container assembly 224 defines a fluid reservoir 227 that, in a manner presently to be described, is accessible via a slit septum 230, which has been insert-molded and comprises a part of reservoir sealing means or septum assembly 226. As best seen in FIG. 67, septum 230 is disposed within a generally cylindrically shaped holding ring 232, which, in turn, is disposed within a housing 234 that is sealably interconnected with top wall 224c.

In the preferred form of this alternate embodiment of the invention, reservoir septum assembly 226 is sealably interconnected with top wall 224c in accordance with the previously described aseptic blow-fill-seal technique.

The primary difference between this latest form of dispensing device of the invention and those previously described herein resides in the provision of a totally different operating means for controlling fluid flow between the collapsible reservoir 224 and the rate control means.

Figure 63:
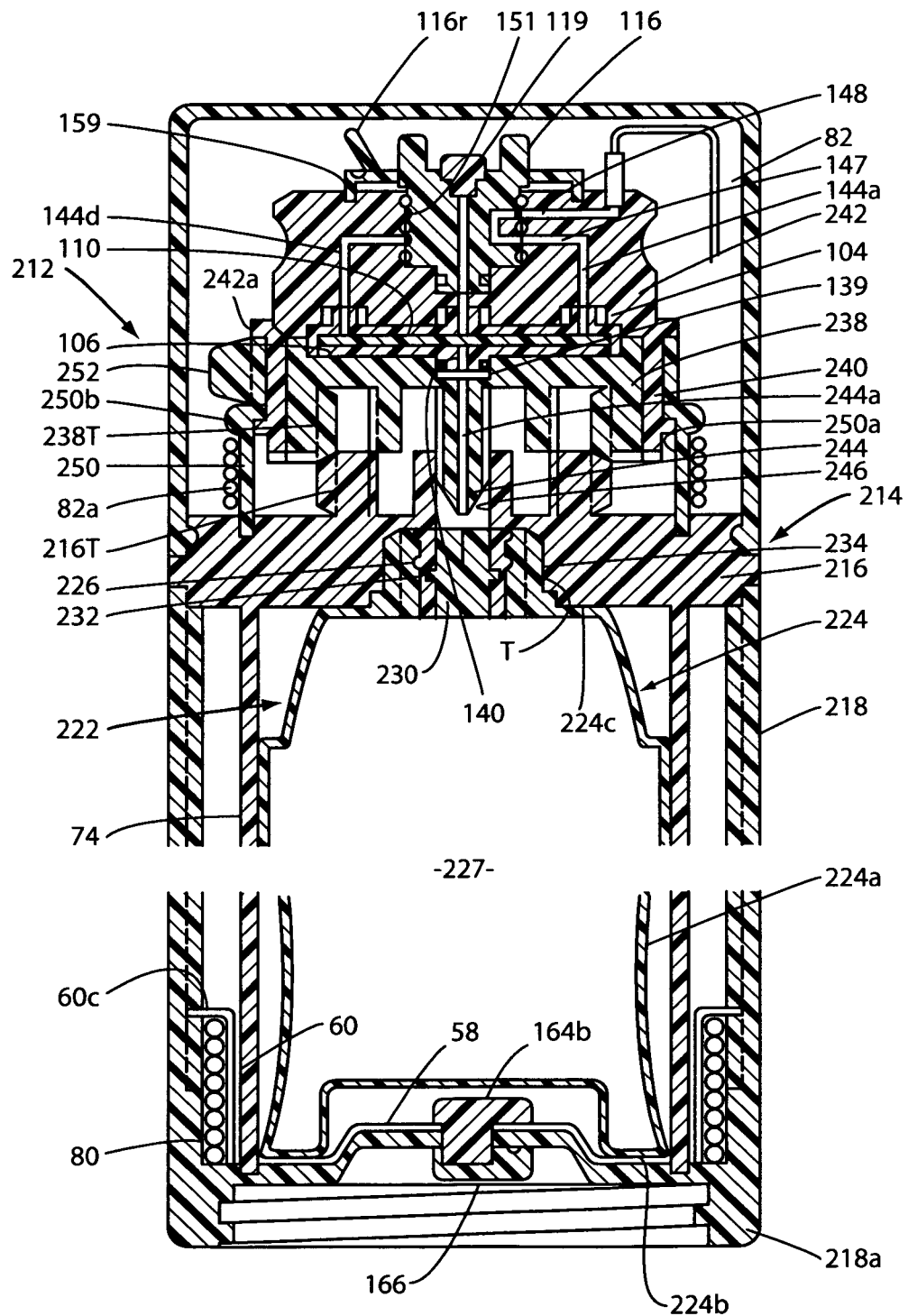
FIG. 63 is a longitudinal cross-sectional view of still another form of the fluid dispensing device of the invention.
Figure 64:
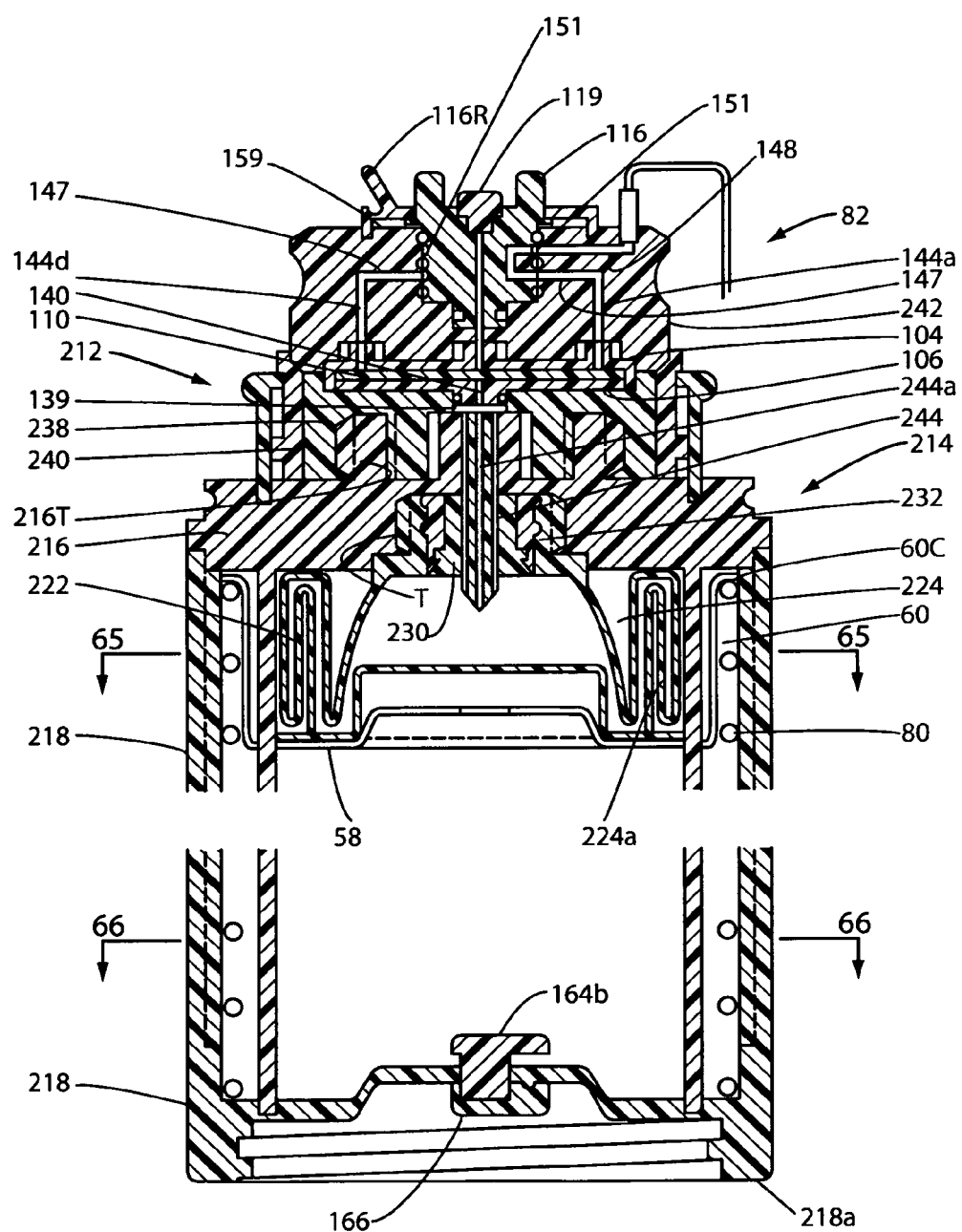
FIG. 64 is a longitudinal cross-sectional view similar to FIG. 63 but showing the various components of the device as they appear following delivery to the patient of the fluid contained within the device reservoir.
Figure 65:
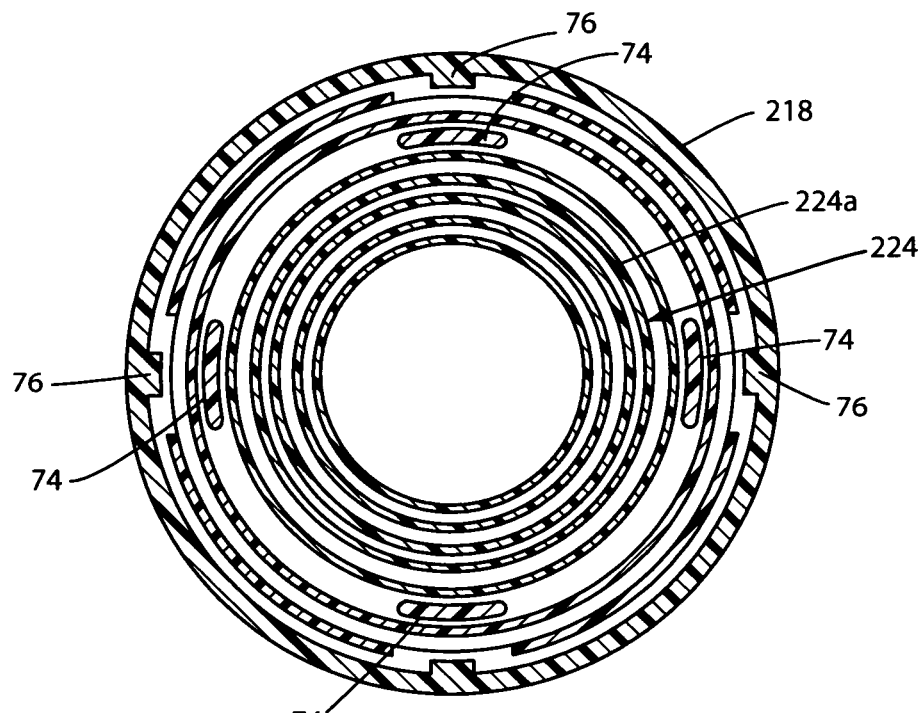
FIG. 65 is a view taken along lines 65-65 of FIG. 64.
Figure 66:
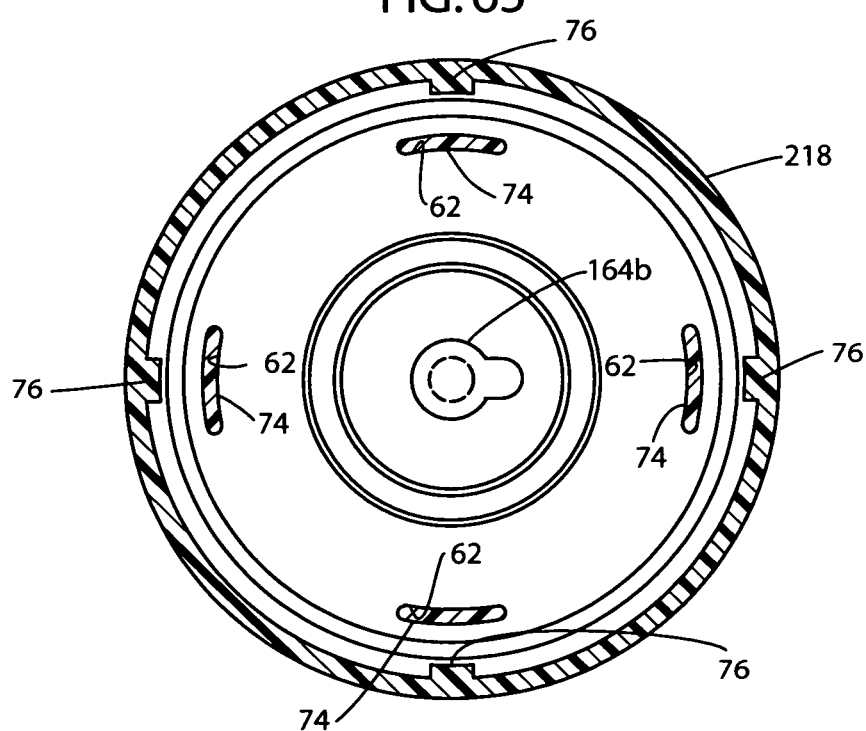
FIG. 66 is a view taken along lines 66-66 of FIG. 64.

As in the earlier described embodiments of the invention, novel guide means are provided for guiding travel of carriage assembly 58 between the first position shown in FIG. 63 and the second position shown in FIG. 64. This important guide means is of identical construction and operation to that previously described herein.

Once again, in order to controllably move the carriage assembly from its first position to its second position, novel stored energy means are provided. This novel stored energy means, which is operably associated with carriage assembly 58, is here provided in the form of a coiled compression spring 80, which is also of identical construction and operation to that previously described.

As in the earlier described embodiments of the invention, when the locking means of the invention is manipulated in a manner to unlock the carriage assembly from base portion 218a of the outer housing 218, spring 80 will move from its retracted position shown in FIG. 63 to its expanded position shown in FIG. 64 and in so doing will controllably move the carriage assembly from its starting position shown in FIG. 63 to its fully deployed or extended position shown in FIG. 64. As the carriage assembly moves toward its deployed position, the collapsible sidewall 224a of the collapsible container 224 will move into the collapsed configuration shown in FIGS. 64 and 69. As the walls of the collapsible container telescopically collapse, the medicinal fluid contained within the container will be controllably expelled therefrom.

To further control the flow of medicinal fluid from reservoir 227 toward the administration set 82 of the invention and then on to the patient, flow control means are provided. Once again, this novel fluid flow control means, comprises two cooperating components, namely a rate control means for controlling the rate of fluid flow from the collapsible reservoir and an operating means for controlling fluid flow between the collapsible reservoir and the rate control means. As previously mentioned, the operating means of this latest form of the invention is a different construction and operation from the previously described operating means. However, the rate control means of this latest form of the invention is similar in construction to that previously described and the rate control assembly of the rate control means is identical in construction and operation to that previously described.

Figure 72:
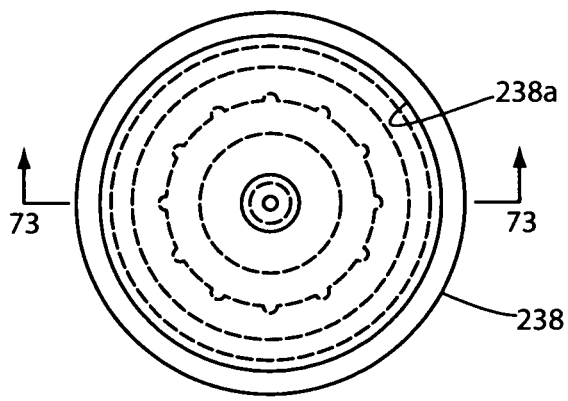
FIG. 72 is a bottom plan view of the septum penetrating assembly of this latest form of the invention.
Figure 73:
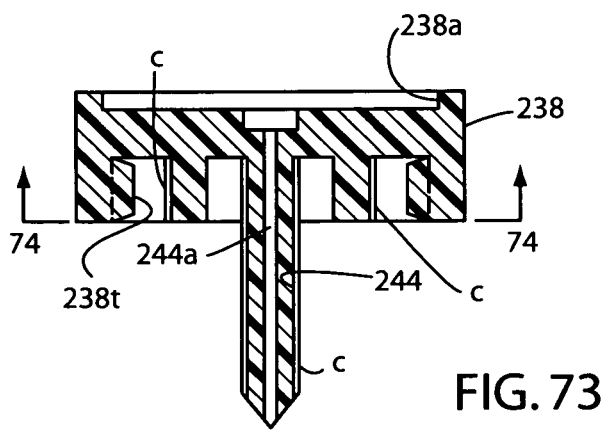
FIG. 73 is a cross-sectional view taken along lines 73-73 of FIG. 72.
Figure 74:
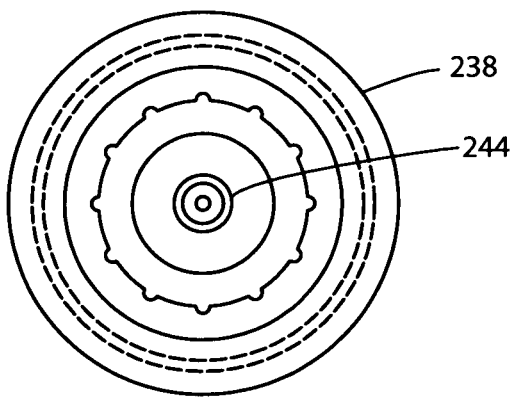
FIG. 74 is a view taken along lines 74-74 of FIG. 73.

The important operating means of this latest embodiment of the invention, which controls fluid flow between reservoir 227 and the rate control means, here comprises a septum penetrating assembly generally designated by the numeral 238 (See FIGS. 72 through 74). Assembly 238, which is disposed within a skirt 240 formed on selector member housing 242, includes internal threads 238t which threadably mate with external threads 216t. Assembly 238 also includes a septum penetrating member 244 which is received within a guide passageway 246 formed on support member 216 (FIG. 63). Assembly 238 also includes a cavity 238a, which closely receives a portion of the rate control assembly 104.

In this latest embodiment of the invention, selector member housing 242, along with septum penetrating assembly 238 is movable within a guide sleeve 250 that extends outwardly from support member 216, from the first position shown in FIG. 63 to the second position shown in FIG. 64. In addition to guiding the travel of the septum penetrating assembly, guide sleeve 250 defines a cylindrical space 250a about which the administration line 82a of the administration set 82 can be coiled in the manner best seen in FIG. 63.

Selector member housing 242 is retained in its first position by a tear strip 252 that is removably receivable between a circumferentially extending rib 242a formed on housing 242 and the upper extremity 250b of guide sleeve 250. When the tear strip 252 is removed in the manner illustrated in FIG. 76, a rotary force exerted on selector member housing 242 will cause the cooperative engagement of the mating threads 238t and 216t to move the housing along with the septum penetrating assembly into the second position shown in FIG. 64 and in so doing will cause the septum penetrating member 244 to pierce the septum in the manner shown in FIG. 64. Piercing of the septum 230 opens a fluid communication path from reservoir 227 to the rate control assembly 104 via a central fluid passageway 244a formed in septum penetrating member 244. From passageway 244a, fluid will flow through conventional particulate filter 139, into inlet 140 of rate control cover 106 of the rate of control assembly 104, into inlet 141 of rate control plate 110 and then into the various circuitous fluid channels of the rate control plate in the manner previously described. The fluid will then flow into the circumferentially spaced-apart fluid passageways formed in the selector housing 242. In operating the device in the manner previously described herein, by rotating the selector member 116, which is carried by selector member housing 242, inlet passageway 144a can be selectively brought into index with one of the radial extensions 147 of the axially extending passageways formed in selector member 242, thereby providing fluid communication between outlet passageway 148 and the selected one of the circuitous flow passageways formed in rate control plate 110 via annular passageway 151 and the selected axially extending passageway formed in the selector member 242. Since outlet passageway 148 is in fluid communication with the administration set 82 of the invention via passageway 151, the rate of fluid flow toward the patient can be precisely controlled by selecting a rate control passageway of appropriate length, width, depth and geometry that is formed in rate control plate 110.

As previously described, by using a conventional syringe, or like device, pierceable elastomeric drug recovery septum 119 can be used to recover any medicament that may remain in reservoir 227 following the fluid delivery step.

Figure 77:
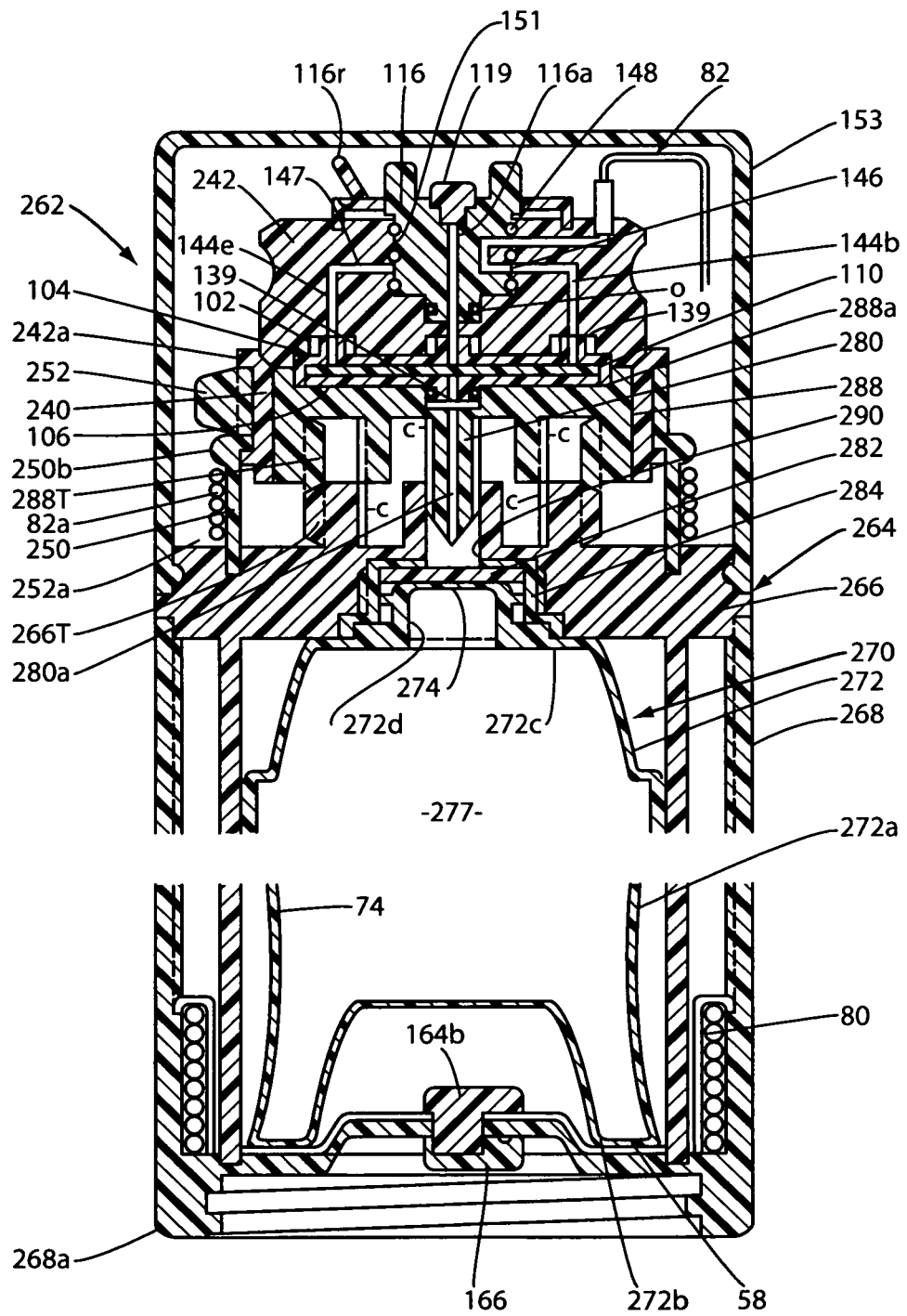
FIG. 77 is a foreshortened, longitudinal, cross-sectional view of an alternate form of the fluid dispensing device of the invention.
Figure 78:
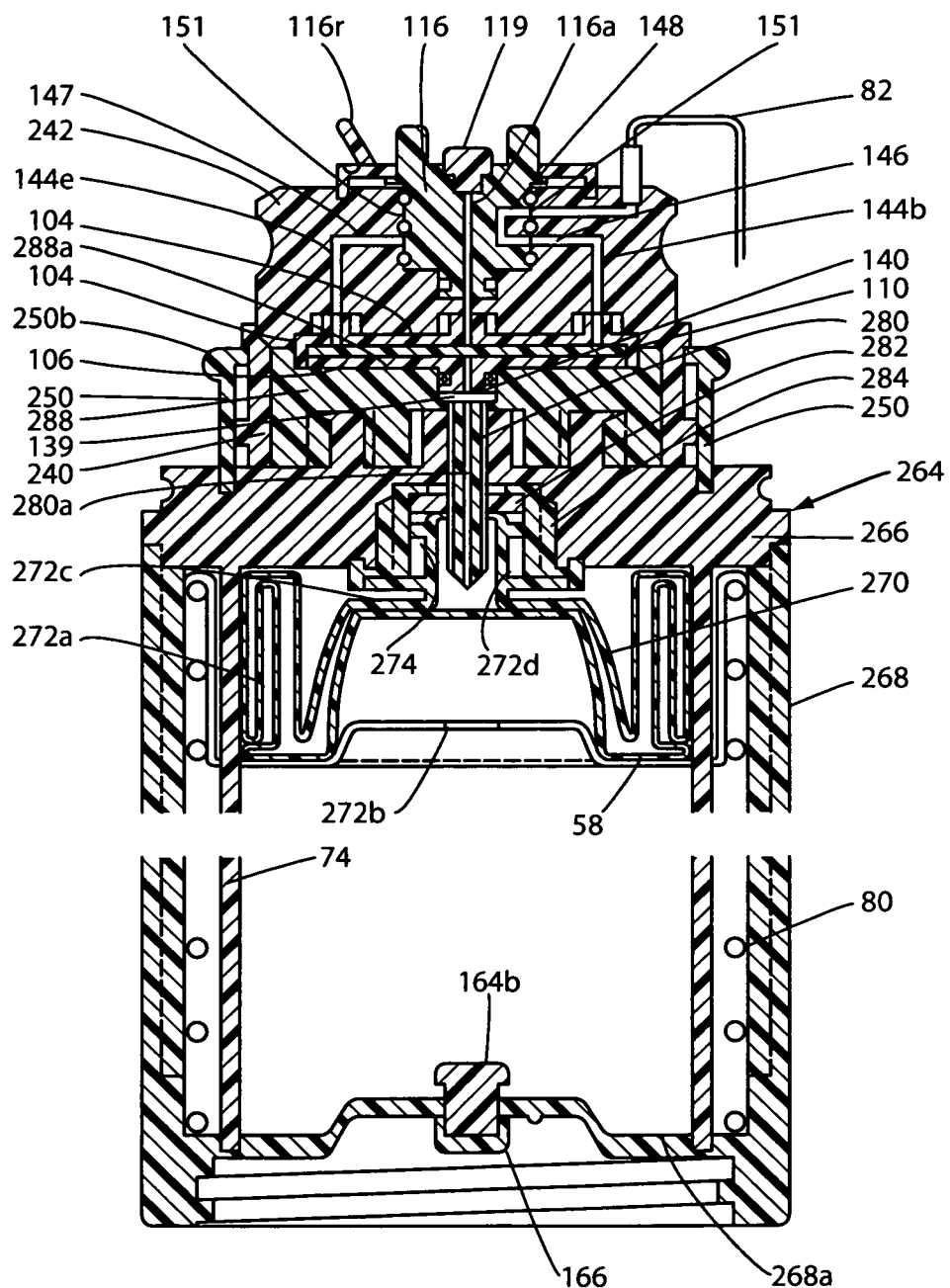
FIG. 78 is a foreshortened longitudinal, cross-sectional view similar to FIG. 77, but showing the various components of the device as they appear following delivery to the patient of the fluid contained within the device reservoir.

Turning next to FIGS. 77 through 82, still another form of the dispensing device of the present invention for dispensing medicaments to a patient is there shown and generally designated by the numeral 262. This alternate form of dispensing device is similar in some respects to that shown in FIGS. 63 through 76 and like numerals are used in FIGS. 77 through 82 to identify like components. As best seen in FIGS. 77 and 78, the supporting structure 264 is similar in many respects to supporting structure 214 and here comprises a connector assembly 266 and a generally cylindrically shaped outer housing 268 that is interconnected with the connector assembly in the manner best seen in FIG. 77 of the drawings.

Disposed within outer housing 268 is the carriage assembly 58, which is of identical construction and operation to that previously described and is releasably locked in its first position by locking means also identical in construction and operation to the locking means previously described herein. Carried by carriage assembly 58 is a reservoir defining assembly 270, which is of a somewhat different construction. This important reservoir defining assembly here includes an integrally formed collapsible container assembly 272 having a continuous wall including a sidewall 272*a*, an interconnected bottom wall 272*b*, an interconnected top wall 272*c* and an interconnected neck portion 272*d* which is sealed at the time of manufacture by a thin pierceable closure wall 274. Neck portion 272*d*, which is preferably integrally formed with top wall 272*c*, forms a part of the novel reservoir access means of the invention. The collapsible container of container assembly 272 comprises a unitary structure that defines a fluid reservoir 277 that, in a manner presently to be described, is accessible via a penetrating member 280 that is adapted to pierce thin closure wall 274 as well as a pierceable membrane 282 which is positioned over closure wall 274 by means of a closure cap 284 which is affixed to the neck portion 272*d* of container assembly 272 (see FIGS. 80 and 81). Penetrating member 280, pierceable membrane 282 and closure cap 284 also form a part of the novel reservoir access means of the invention. Container assembly 272 can be interconnected with connector member 266 as a snapfit by a threaded construction or any other convenient mechanism.

In the preferred form of this latest alternate embodiment of the invention, closure wall 274 is sealably interconnected with neck portion 272*d* in accordance with the previously described aseptic blow-fill-seal technique.

The primary difference between this latest form of dispensing device of the invention and those previously described herein resides in the somewhat differently configured container assembly 272 and the somewhat differently configured penetrating member 280. In constructing the container assembly 272, the basic container is formed using the aseptic blow-fill-seal technique earlier described herein and the reservoir portion of the container is sealed by reservoir accessing means which comprises the thin closure wall 274. The piercable membrane 282 is then positioned over the closure wall 274 and the cap 284 is positioned over the piercable membrane and secured to neck portion 272*d* by any suitable means such as adhesive bonding or sonic welding. Membrane 282, cap 284 and neck portion 272*d* all comprise a part of the reservoir accessing means of this latest form of the invention. It is important to note that closure wall 274 effectively prevents the medicament contained within the fluid reservoir from coming in contact with the membrane 282 at any time prior to accessing the reservoir.

As in the earlier described embodiments of the invention, novel guide means are provided for guiding travel of carriage assembly 58 between the first position shown in FIG. 77 and the second position shown in FIG. 78. This important guide means is of identical construction and operation to that previously described herein.

Once again, in order to controllably move the carriage assembly from its first position to its second position, novel stored energy means are provided. This novel stored energy means, which is operably associated with carriage assembly 58, is here provided in the form of a coiled spring 80, which is also identical in construction and operation to that previously described.

As in the earlier described embodiments of the invention, when the locking means of the invention is manipulated in a manner to unlock the carriage assembly from base portion 268*a* of the outer housing 268, spring 80 will move from its retracted position shown in FIG. 77 to its expanded position shown in FIG. 78 and in so doing will controllably move the carriage assembly from its starting position shown in FIG. 77 to its fully deployed or extended position shown in FIG. 78. As the carriage assembly moves toward its deployed position, the collapsible sidewall 272*a* of the collapsible container 272 will move into the collapsed configuration shown in FIGS. 78 and 82. As the collapsible container collapses, the medicinal fluid contained within the container will be controllably expelled therefrom.

To further control the flow of medicinal fluid from reservoir 277 toward the administration set 82 of the invention and then on to the patient, flow control means are provided. Once again, this novel fluid flow control means, comprises two cooperating components, namely a rate control means for controlling the rate of fluid flow from the collapsible reservoir and an operating means for controlling fluid flow between the collapsible reservoir and the rate control means. As previously mentioned, the operating means of this latest form of the invention is of a different construction and operation from the previously described operating means. However, the rate control means of this latest form of the invention is similar in construction to that previously described and the rate control assembly of the rate control means is identical in construction and operation to that previously described in connection with Figure drawings 36 through 74A.

The important operating means of this latest embodiment of the invention, which controls fluid flow between collapsible reservoir 277 and the rate control means, here comprises a penetrating assembly generally designated by the numeral 288 (See FIGS. 77 and 78). Assembly 288, which is disposed within a skirt 240 formed on a selector member housing 242, includes the previously identified penetrating member 280 which is sealably received within a guide passageway 290 formed on support member 266 (FIG. 77). Assembly 288 also includes a cavity 288*a*, which closely receives a portion of the rate control assembly 104.

In this latest embodiment of the invention, selector member housing 242, along with septum penetrating assembly 288 is movable within a guide sleeve 250 that extends outwardly from support member 266, from the first position shown in FIG. 77 to the second position shown in FIG. 78. In addition to guiding the travel of the penetrating assembly, guide sleeve 250 defines a cylindrical space 252*a* about which the administration line 82*a* of the administration set 82 can be coiled in the manner best seen in FIG. 77.

As in the earlier described embodiment, selector member housing 242 is retained in its first position by a tear strip 252 that is removably receivable between a circumferentially extending rib 242*a* formed on housing 242 and the upper extremity 250*b* of guide sleeve 250. When the tear strip 252 is removed, a rotary force exerted on selector member housing 242 will move the housing along with the penetrating assembly into the second position shown in FIG. 78 and in so doing will cause the penetrating member 280 to pierce the membrane 282 as well as the closure wall 274 in the manner shown in FIG. 78. Piercing of the membrane 282 and the closure wall 274 opens a fluid communication path from reservoir 277 to the rate control assembly 104 via a central fluid passageway 280*a* formed in penetrating member 280. From passageway 280*a*, fluid will flow through conventional particulate filter 139, into inlet 140 of rate control cover 106 of the rate of control assembly 104, into inlet 141 of rate control plate 110 and then into the various circuitous fluid channels of the rate control plate in the manner previously described. The fluid will then flow into the circumferentially spaced-apart fluid passageways formed in the selector housing 242. In operating the device in the manner previously described herein, by rotating the selector member 116, which is carried by selector member housing 242, inlet passageway 144a can be selectively brought into index with one of the radial extensions 147 of the axially extending passageways formed in selector member 242, thereby providing fluid communication between outlet passageway 148 and the selected one of the circuitous flow passageways formed in rate control plate 110 via annular passageway 151 and the selected axially extending passageway formed in the selector member 242. Since outlet passageway 148 is in fluid communication with the administration set 82 of the invention via passageway 151, the rate of fluid flow toward the patient can be precisely controlled by selecting a rate control passageway of appropriate length, width and geometry that is formed in rate control plate 110.

Referring to FIGS. 83 through 87, yet another form of the dispensing device of the present invention for dispensing medicaments to a patient is there shown and generally designated by the numeral 302. This alternate form of dispensing device is similar in most respects to that shown in FIGS. 77 through 82 and like numerals are used in FIGS. 83 through 87 to identify like components. The major difference between this latest embodiment of the invention and that shown in FIGS. 77 through 82 resides in the differently configured reservoir defining container 304. As shown in FIG. 85 container 304, rather than being in the nature of the collapsible bottle, comprises a reservoir defining container formed as a unitary structure having a bellows-like sidewall 304a that is movable from the expanded, starting configuration shown in FIG. 83 to the collapsed configuration shown in FIG. 84. This important reservoir defining container here includes, in addition to sidewall 304a, an interconnected bottom wall 304b, an interconnected top wall 304c and an interconnected neck portion 304d which is sealed at the time of manufacture by an integrally formed, thin closure wall 305. Neck portion 304d which is preferably integrally formed with top wall 304c, forms a part of the novel reservoir access means of the invention. Collapsible container 304 defines a fluid reservoir 307 that, in a manner presently to be described, is accessible via a penetrating member 280 that is adapted to pierce closure wall 305 as well as a pierceable membrane 306 which is positioned over closure wall 305 of by means of a closure cap 309 which is affixed to the neck portion 304d of container assembly 304 (see also FIG. 87).

Figure 83:
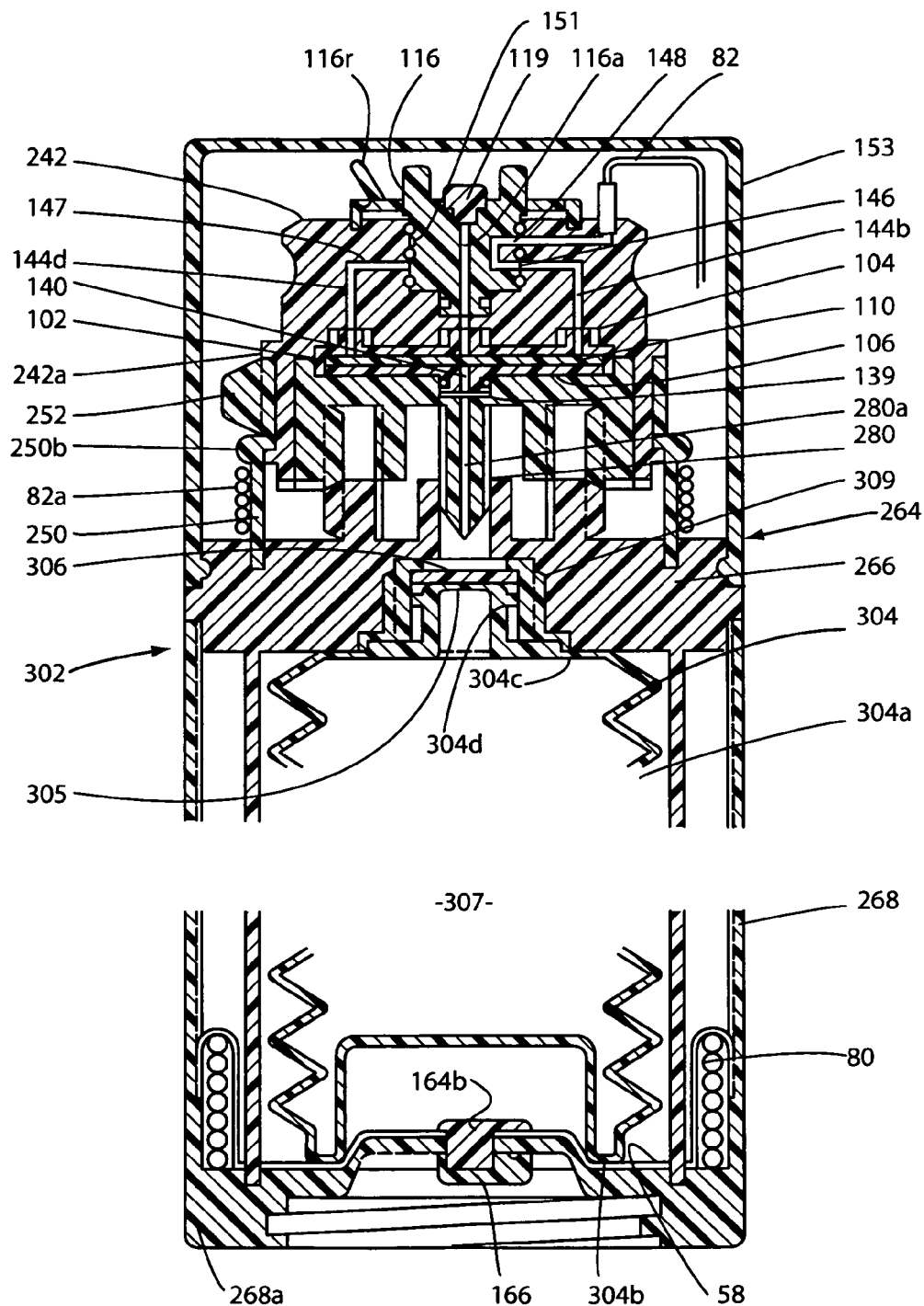
FIG. 83 is a foreshortened, longitudinal, cross-sectional view of yet another alternate form of the fluid dispensing device of the invention.
Figure 84:
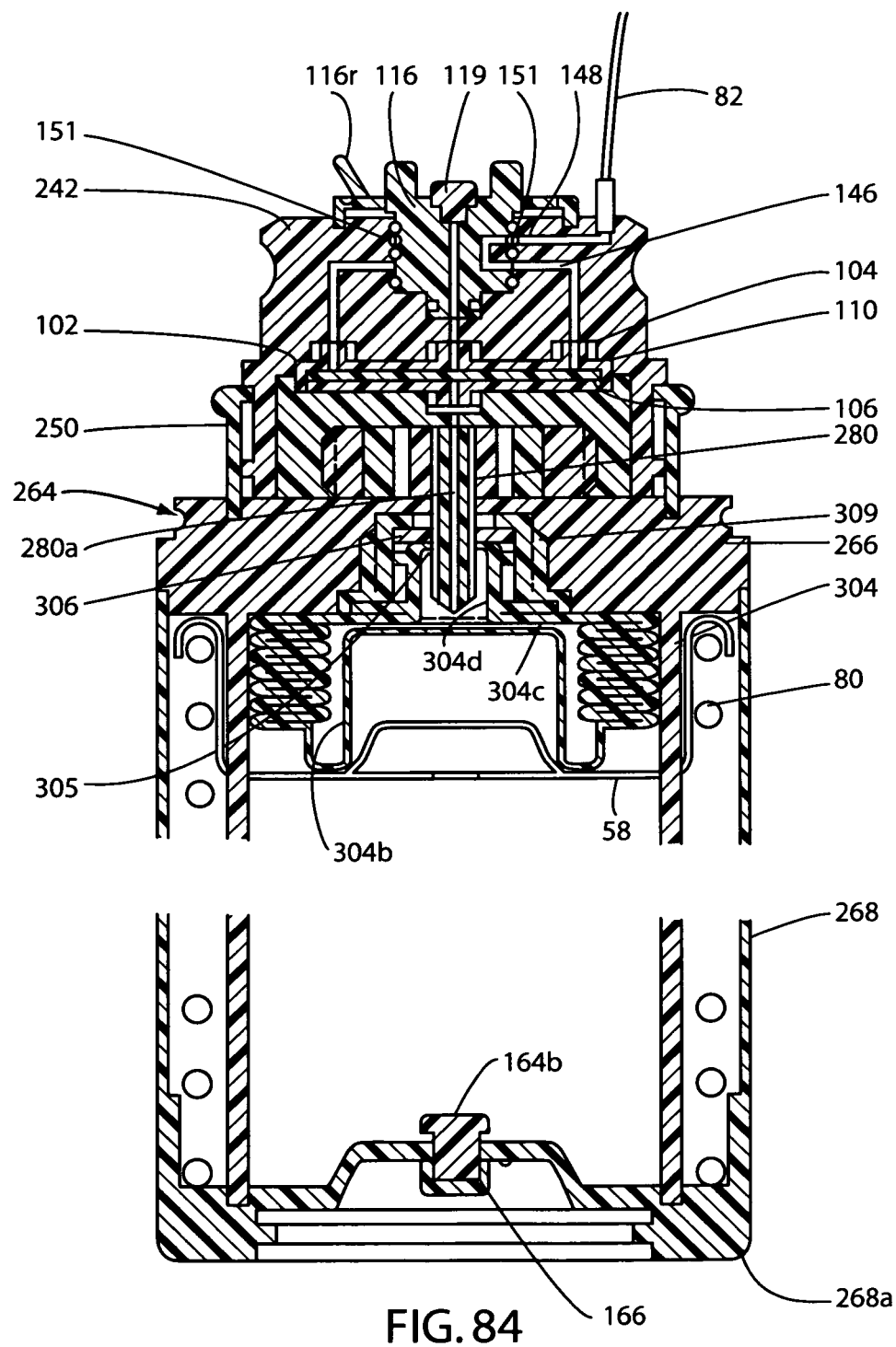
FIG. 84 is a foreshortened longitudinal, cross-sectional view similar to FIG. 83, but showing the various components of the device as they appear following delivery to the patient of the fluid contained within the device reservoir.

As best seen in FIGS. 83 and 84 the supporting structure 264 is substantially identical to the supporting structure of the last described embodiment and here comprises a connector assembly 266 and a generally cylindrically shaped outer housing 268 that is interconnected with the connector assembly in the manner best seen in FIG. 83 of the drawings.

Disposed within outer housing 268 is the carriage assembly 58, which is of identical construction and operation to that previously described and is releasably locked in its first position by locking means also identical in construction and operation to the locking means previously described herein. Carried by carriage assembly 58 is the previously described reservoir defining container 304.

As in the last described embodiment of the invention, closure wall 305 is sealably interconnected with neck portion 304d in accordance with the previously described aseptic blow-fill-seal technique. As in the last described embodiment of the invention, the basic container 304 is formed using the earlier described aseptic blow-fill-seal technique and the reservoir portion of the container is sealed by the thin closure wall 305. The pierceable membrane 306 is then positioned over the closure wall 305 and the cap 309 is positioned over the piercable membrane and secured to the integrally formed neck portion 304d by any suitable means such as adhesive bonding or sonic welding.

As before, novel guide means are provided for guiding travel of carriage assembly 58 between the first position shown in FIG. 83 and the second position shown in FIG. 84. This important guide means is of identical construction and operation to that previously described herein.

Once again, in order to controllably move the carriage assembly from its first position to its second position, novel stored energy means are provided. This novel stored energy means, which is operably associated with carriage assembly 58, is here provided in the form of a coiled spring 80, which is also identical in construction and operation to that previously described.

As in the earlier described embodiments of the invention, when the locking means of the invention is manipulated in a manner to unlock the carriage assembly from base portion 268a of the outer housing 268, spring 80 will move from its compressed position shown in FIG. 83 to its expanded position shown in FIG. 84 and in so doing will controllably move the carriage assembly from its starting position shown in FIG. 83 to its fully deployed or extended position shown in FIG. 84. As the carriage assembly moves toward its deployed position, the accordion-like, collapsible sidewall 304a of the collapsible container 304 will move into the collapsed configuration shown in FIG. 84. As the container collapses, the medicinal fluid contained within the container will be controllably expelled therefrom.

To further control the flow of medicinal fluid from reservoir 307 toward the administration set 82 of the invention and then on to the patient, flow control means are provided. These important flow control means are identical to those previously described in connection with the embodiment of FIGS. 77 through 82 and will not here be further discussed.

As in the last described embodiment, selector member housing 242 is retained in its first position by a tear strip 252 that is removably receivable between a circumferentially extending rib 242a formed on housing 242 and the upper extremity 250b of guide sleeve 250. When the tear strip 252 is removed, a rotary force exerted on selector member housing 242 will move the housing along with the penetrating assembly into the second position shown in FIG. 84 and in so doing will cause the penetrating member 280 to pierce the membrane 306 as well as the closure wall 305. Piercing of the membrane 306 and the closure wall 305 opens a fluid communication path from reservoir 307 to the rate control assembly 104 via a central fluid passageway 280a formed in septum penetrating member 280. From passageway 280a, fluid will flow through conventional particulate filter 139, into inlet 140 of rate control cover 106 of the rate of control assembly 104, into inlet 141 of rate control plate 110 and then into the various circuitous fluid channels of the rate control plate in the manner previously described. The fluid will then flow into the circumferentially spaced-apart fluid passageways formed in the selector housing 242. In operating the device in the manner previously described herein, by rotating the selector member 116, which is carried by selector member housing 242, inlet passageway 144a can be selectively brought into index with one of the radial extensions 147 of the axially extending passageways formed in selector member 242, thereby providing fluid communication between outlet passageway 148 and the selected one of the circuitous flow passageways formed in rate control plate 110 via annular passageway 151 and the selected axially extending passageway formed in the selector member 242. Since outlet passageway 148 is in fluid communication with the administration set 82 of the invention via passageway 151, the rate of fluid flow toward the patient can be precisely controlled by selecting a rate control passageway of appropriate length that is formed in rate control plate 110.

Figure 88:
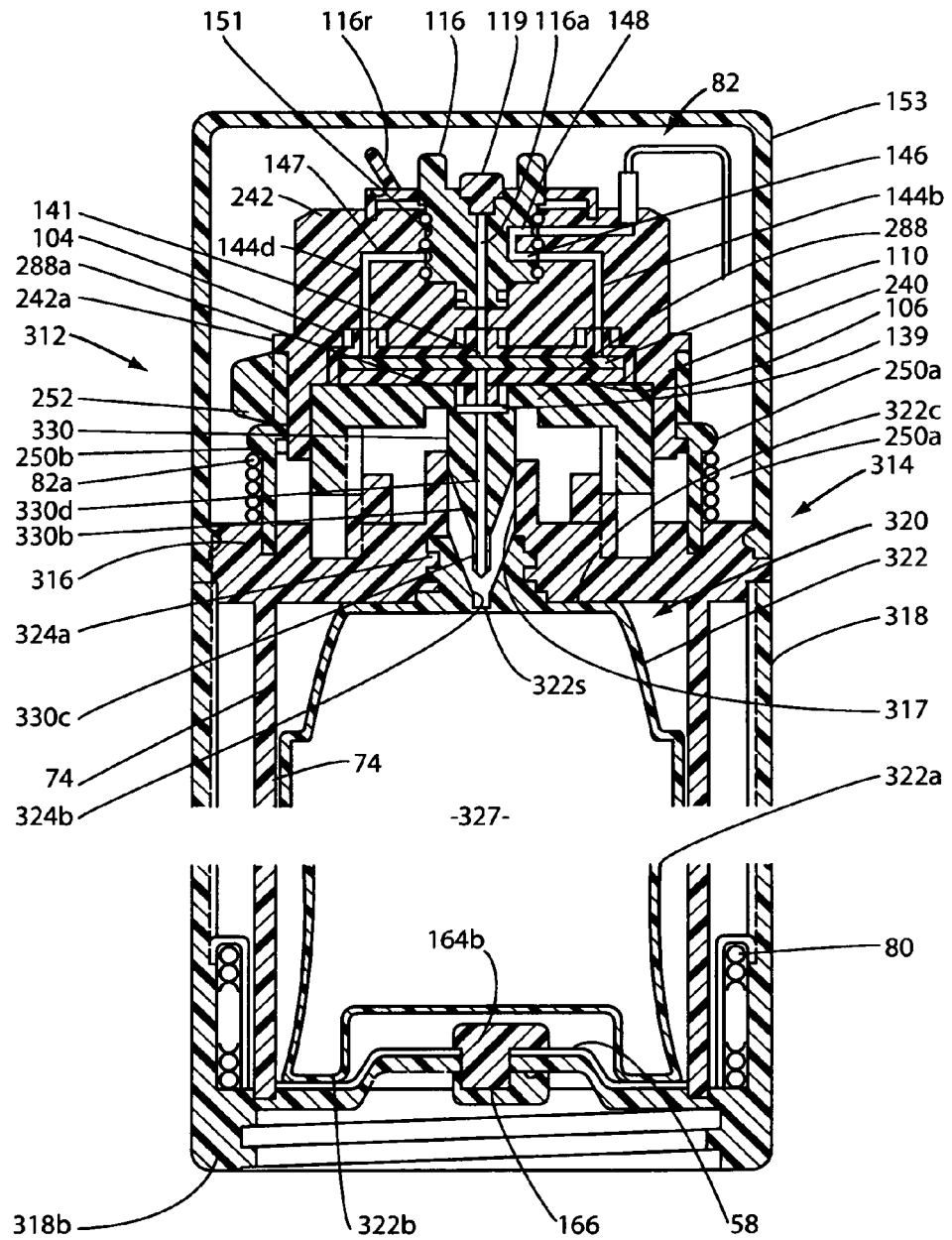
FIG. 88 is a foreshortened, longitudinal, cross-sectional view of an alternate form of the fluid dispensing device of the invention.
Figure 89:
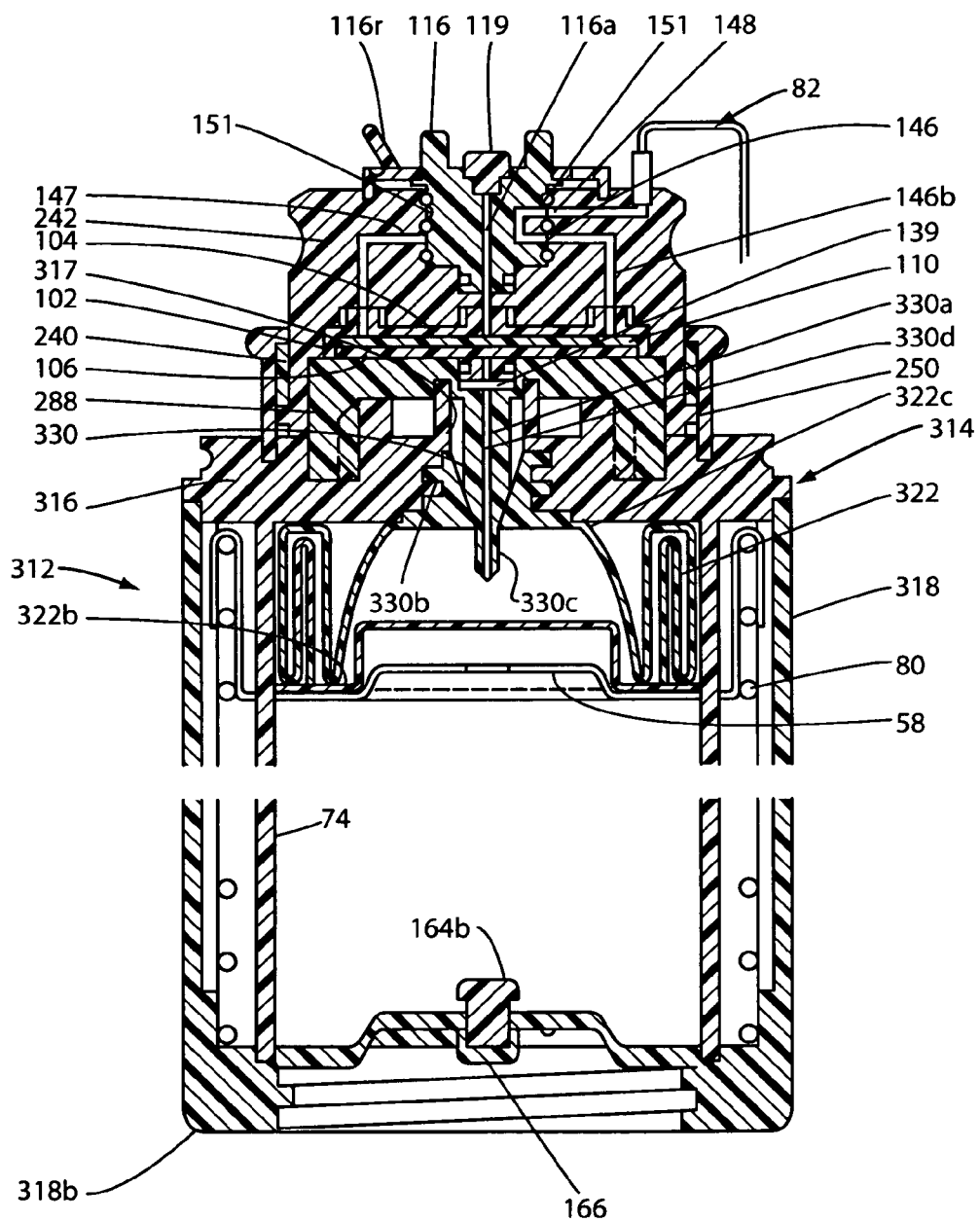
FIG. 89 is a foreshortened longitudinal, cross-sectional view similar to FIG. 88, but showing the various components of the device as they appear following delivery to the patient of the fluid contained within the device reservoir.

Turning next to FIGS. 88 through 91, still another form of the dispensing device of the present invention for dispensing medicaments to a patient is there shown and generally designated by the numeral 312. This alternate form of dispensing device is similar in many respects to that shown in FIGS. 83 through 87 and like numerals are used in FIGS. 88 through 91 to identify like components. As best seen in FIGS. 88 and 89, the supporting structure 314 is similar in many respects to supporting structure 214 and here comprises a connector assembly 316 and a generally cylindrically shaped outer housing 318 that is interconnected with the connector assembly in the manner best seen in FIG. 88 of the drawings.

Disposed within outer housing 318 is the carriage assembly 58, which is of identical construction and operation to that previously described and is releasably locked in its first position by locking means also identical in construction and operation to the locking means previously described herein. Carried by carriage assembly 58 is a reservoir defining assembly 320, which is of a somewhat different construction. This important reservoir defining assembly here includes a collapsible container assembly 322 having a sidewall 322a, an interconnected bottom wall 322b and an interconnected top wall 322c. Connected to top wall 322c and extending therefrom, is a Luer-like connector 324 having external threads 324a and a sealing wall 324b. Connector 324, which is interconnected with top wall 322c is integrally formed and sealably interconnected at the time of manufacture of the collapsible container assembly 322, forms a part of the novel reservoir access means of this latest form of the invention. Collapsible container assembly 322 defines a fluid reservoir 327 that, in a manner presently to be described, is accessible via a slightly differently configured penetrating member 330 that is adapted to pierce top sealing wall 322s and sealably engage tapered sealing wall 324b (FIGS. 88 and 91).

In the preferred form of this latest alternate embodiment of the invention, Luer-like connector 324 is sealably interconnected with top wall 322c in accordance with the previously described aseptic blow-fill-seal technique.

As previously mentioned, the primary differences between this latest form of dispensing device of the invention and those previously described herein resides in the somewhat differently configured container assembly 322 and the somewhat differently configured penetrating member 330. In constructing the container assembly 322, the basic container is formed as a unitary structure using the aseptic blow-fill-seal technique earlier described herein and the reservoir portion of the container is sealed by the interconnected walls of the container and integral sealing wall 322s.

As in the earlier described embodiments of the invention, novel guide means are provided for guiding travel of carriage assembly 58 between the first position shown in FIG. 88 and the second position shown in FIG. 89. This important guide means is of identical construction and operation to that previously described herein.

Once again, in order to controllably move the carriage assembly from its first position to its second position, novel stored energy means are provided. This novel stored energy means, which is operably associated with carriage assembly 58, is here provided in the form of a coiled spring 80, which is also identical in construction and operation to that previously described.

As in the earlier described embodiments of the invention, when the locking means of the invention is manipulated in a manner to unlock the carriage assembly from base portion 318b of the outer housing 318, spring 80 will move from its retracted position shown in FIG. 88 to its expanded position shown in FIG. 89 and in so doing will controllably move the carriage assembly from its starting position shown in FIG. 88 to its fully deployed or extended position shown in FIG. 89. As the carriage assembly moves toward its deployed position, the collapsible sidewall 322a of the collapsible container 322 will move into the collapsed configuration shown in FIGS. 89 and 89A. As the collapsible container collapses, the medicinal fluid contained within the container will be controllably expelled therefrom through fluid passageway 330d formed in the penetrating member 330.

To further control the flow of medicinal fluid from reservoir 327 toward the administration set 82 of the invention and then on to the patient, flow control means are provided. Once again, this novel fluid flow control means, comprises two cooperating components, namely a rate control means for controlling the rate of fluid flow from the collapsible reservoir and an operating means for controlling fluid flow between the collapsible reservoir and the rate control means. These components are, in this latest embodiment of the invention, substantially identical in construction and operation to those described in connection with Figure drawings 63 through 76. As previously mentioned, the penetrating member 330 is of a slightly different construction that is better suited for penetrating top wall 322s of the container assembly. More particularly, penetrating member 330 has a generally cylindrically shaped body portion 330a, an intermediate tapered portion 330b and a reduced diameter penetrating extremity 330c. Tapered portion 330b engages tapered sealing wall 324b forming a substantially fluid seal.

The rate control means of this latest form of the invention is identical in construction and operation to that previously described in connection with Figure drawings 36 through 74A.

Penetrating member 330 comprises a part of the previously described penetrating assembly, which is generally designated in FIGS. 88 and 89 by the numeral 288. Support member 316 includes a guide passageway 317, which guides the travel of the penetrating member 330. Assembly 288 also includes a cavity 288a, which closely receives a portion of the rate control assembly 104.

In this latest embodiment of the invention, selector member housing 242, along with assembly 288 is movable from the first position shown in FIG. 88 to the second position shown in FIG. 89. In addition to guiding the travel of member 242, guide sleeve 250 defines a cylindrical space 250a about which the administration line 82a of the administration set 82 can be coiled in the manner best seen in FIG. 88.

As in the earlier described embodiment, selector member housing 242 is retained in its first position by a tear strip 252 that is removably receivable between a circumferentially extending rib 242a formed on housing 242 and the upper extremity 250b of guide sleeve 250. When the tear strip 252 is removed, a rotary force exerted on selector member housing 242 will move the housing along with the penetrating assembly into the second position shown in FIG. 89 and in so doing will cause the penetrating member 330 to pierce upper wall 322s in the manner shown in FIG. 89. Piercing of wall 322s opens a fluid communication path from reservoir 327 to the rate control assembly 104 via a central fluid passageway 330d formed in septum penetrating member 330. From passageway 330d, fluid will flow through conventional particulate filter 139, into inlet 140 of rate control cover 106 of the rate of control assembly 104, into inlet 141 of rate control plate 110 and then into the various circuitous fluid channels of the rate control plate in the manner previously described. The fluid will then flow into the circumferentially spaced-apart fluid passageways formed in the selector housing 242. In operating the device in the manner previously described herein, by rotating the selector member 116, which is carried by selector member housing 242, inlet passageway 144a can be selectively brought into index with one of the radial extensions 147 of the axially extending passageways formed in selector member 242, thereby providing fluid communication between outlet passageway 148 and the selected one of the circuitous flow passageways formed in rate control plate 110 via annular passageway 151 and the selected axially extending passageway formed in the selector member 242. Since outlet passageway 148 is in fluid communication with the administration set 82 of the invention via passageway 151, the rate of fluid flow toward the patient can be precisely controlled by selecting a rate control passageway of appropriate length that is formed in rate control plate 110.

Turning next to FIGS. 92 through 96, still another form of the dispensing device of the present invention for dispensing medicaments to a patient is there shown and generally designated by the numeral 332. This alternate form of dispensing device is similar in many respects to that shown in FIGS. 88 through 91 and like numerals are used in FIGS. 92 through 96 to identify like components.

Figure 92:
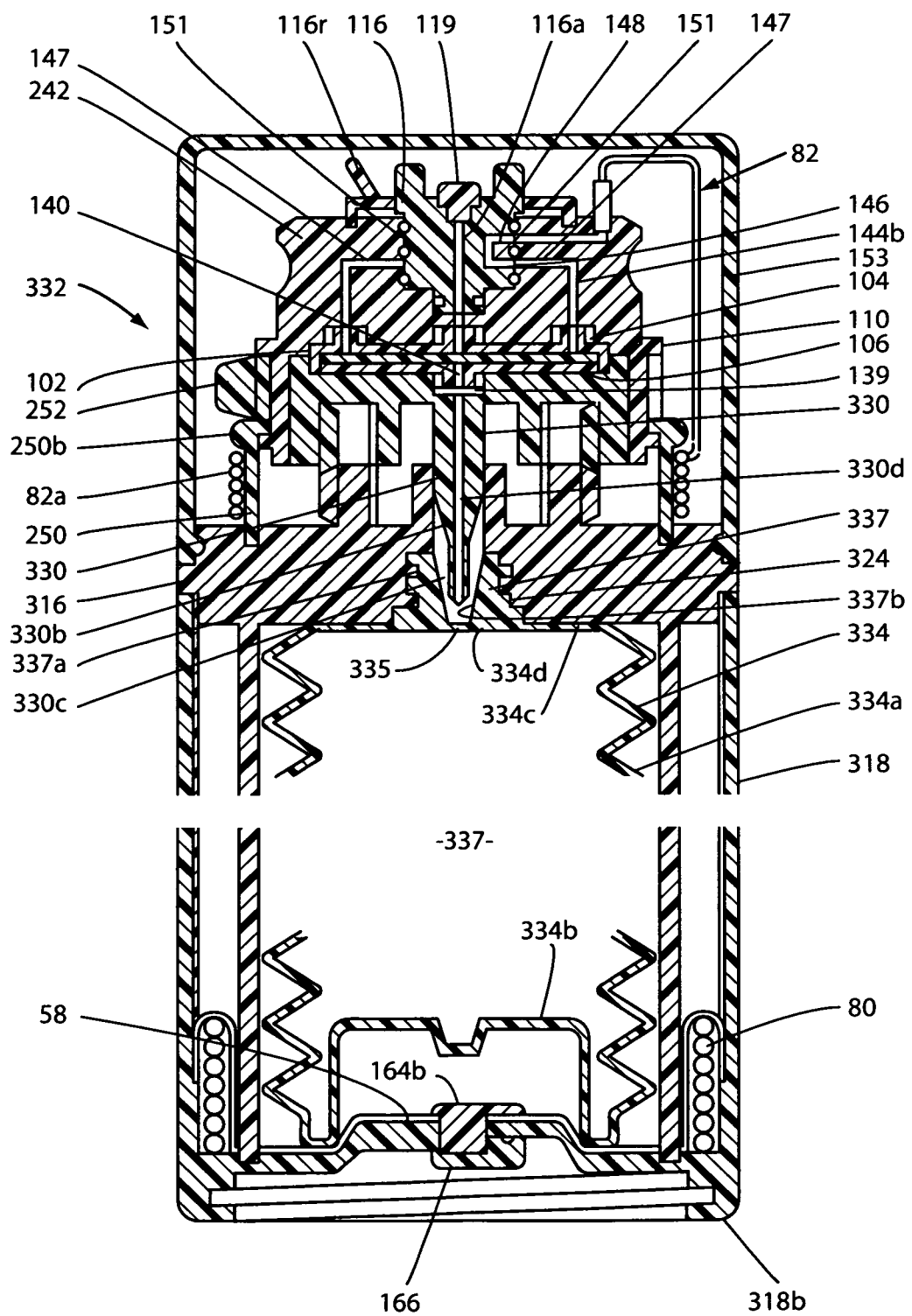
FIG. 92 is a foreshortened, longitudinal, cross-sectional view of still another alternate form of the fluid dispensing device of the invention.

The major difference between this latest embodiment of the invention and that shown in FIGS. 88 through 91 resides in the differently configured reservoir defining container 334. As shown in FIG. 92, container 334, rather than being in the nature of the collapsible bottle, comprises a reservoir defining unitary container having a bellows-like sidewall 334a that is movable from the expanded, starting configuration shown in FIG. 92 to the collapsed configuration shown in FIG. 93. This important reservoir defining container here includes, in addition to sidewall 334a, an interconnected bottom wall 334b, and an interconnected top wall 334c.

Connected to top wall 334c and extending therefrom, is a Luer-like connector 337 having external threads 337a and a tapered sealing wall 337b. Connector 337, which forms a part of the novel reservoir access means of this latest form of the invention, is interconnected with top wall 334c at the time of manufacture of the collapsible container assembly 334. Collapsible container 334 defines a fluid reservoir 337 that is accessible via a penetrating member 330 that is similar to the penetrating member previously described in connection with FIGS. 88 and 89 and is adapted to pierce closure wall 335 in the manner previously described. It is to be noted that tapered portion 330b of the penetrating member engages the tapered wall 337b of container 337 to form a substantially fluid seal.

Figure 93:
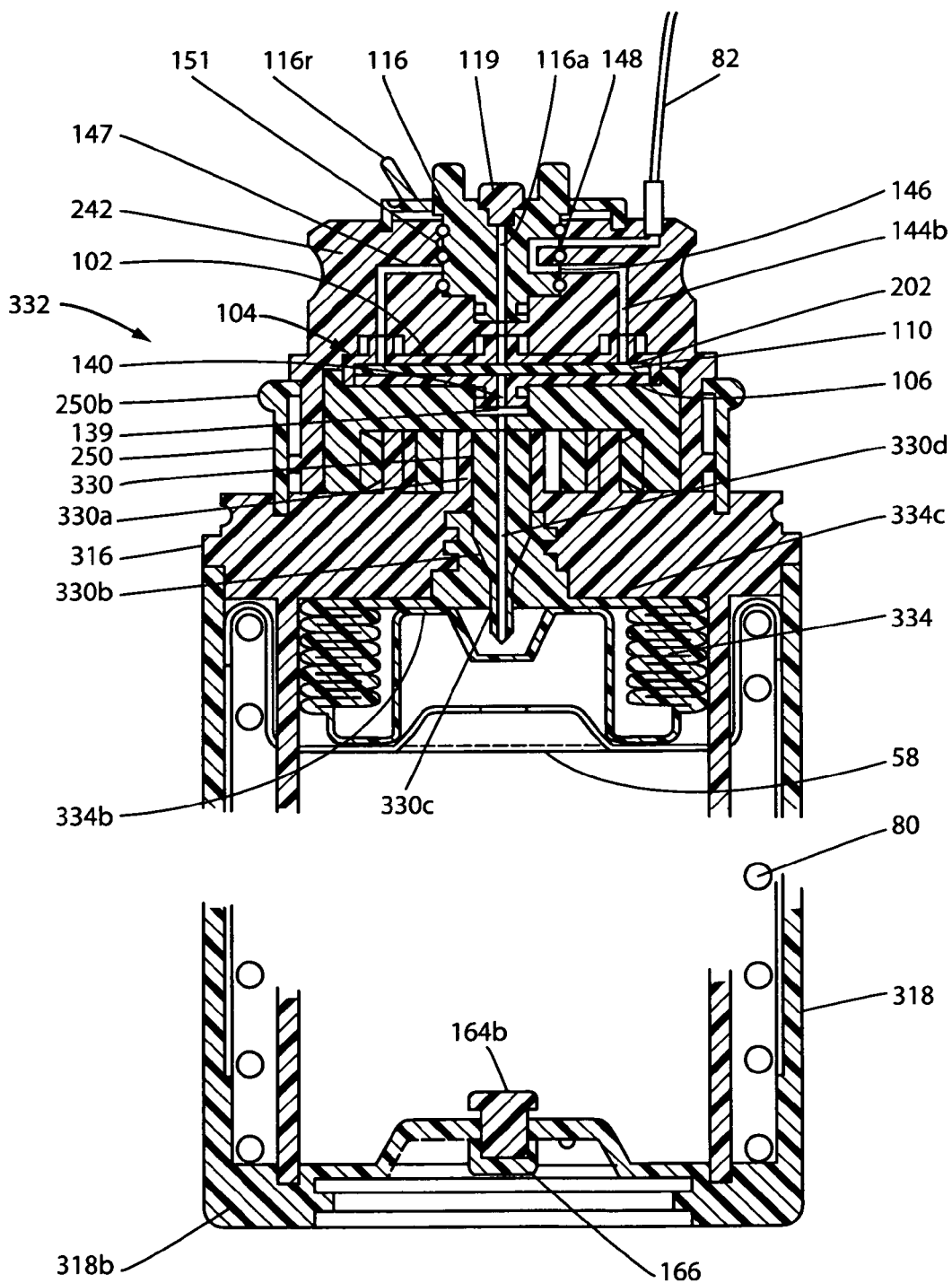
FIG. 93 is a foreshortened, longitudinal, cross-sectional view similar to FIG. 92, but showing the various components of the device as they appear following delivery to the patient of the fluid contained within the device reservoir.

As indicated in FIGS. 92 and 93 the supporting structure 316 is substantially identical to the supporting structure of the last described embodiment. Similarly, the carriage assembly 58 which is carried within cylindrically shaped outer housing 318 is of identical construction and operation to that previously described and is releasably locked in its first position by locking means also identical in construction and operation to the locking means previously described herein. Carried by carriage assembly 58 in the manner illustrated in FIG. 92 is the previously described reservoir defining container 334.

As in the last described embodiment of the invention, closure wall 335 is sealably interconnected with neck portion 337 in accordance with the previously described aseptic blow-fill-seal technique. As before, the basic container 334 is formed using the earlier described aseptic blow fill technique and the reservoir portion of the container is sealed by the thin closure wall 335.

Once again, in order to controllably move the carriage assembly 58 from its first position to its second position, novel stored energy means are provided. This novel stored energy means, which is operably associated with carriage assembly 58, is here provided in the form of a coiled spring 80, which is also identical in construction and operation to that previously described.

As in the earlier described embodiments of the invention, when the locking means of the invention is manipulated in a manner to unlock the carriage assembly from base portion 318b of the outer housing 318, spring 80 will move from its compressed position shown in FIG. 92 to its expanded position shown in FIG. 93 and in so doing will controllably move the carriage assembly from its starting position to its fully deployed or extended position as shown in FIG. 93. As the carriage assembly moves toward its deployed position, the accordion-like, collapsible sidewall 334a of the collapsible container 334 will move into the collapsed configuration shown in FIG. 93. As the container collapses, the medicinal fluid contained within the container will be controllably expelled therefrom.

To further control the flow of medicinal fluid from reservoir 337 toward the administration set 82 of the invention and then on to the patient, flow control means are provided. These important flow control means are identical to those previously described in connection with the embodiment of FIGS. 88 through 91 and will not here be further discussed.

As in the last described embodiment, selector member housing 242 is retained in its first position by a tear strip 252. When the tear strip 252 is removed, a rotary force exerted on selector member housing 242 will move the housing along with the penetrating assembly into the second position shown in FIG. 93 and in so doing will cause the penetrating member 330 to pierce the closure wall 335 and sealably engage sealing wall 337b.

Piercing of the closure wall 335 opens a fluid communication path from reservoir 337 to the rate control assembly 104 via a central fluid passageway 330d formed in penetrating member 330. From passageway 330d, fluid will flow through conventional particulate filter 139, into inlet 140 of rate control cover 106 of the rate control assembly 104, into inlet 141 of rate control plate 110 and then into the various circuitous fluid channels of the rate control plate in the manner previously described. The fluid will then flow into the circumferentially spaced-apart fluid passageways formed in the selector housing 242. In operating the device in the manner previously described herein, by rotating the selector member 116, which is carried by selector member housing 242, inlet passageway 144a can be selectively brought into index with one of the radial extensions 147 of the axially extending passageways formed in selector member 242, thereby providing fluid communication between outlet passageway 148 and the selected one of the circuitous flow passageways formed in rate control plate 110 via annular passageway 151 and the selected axially extending passageway formed in the selector member 242. Since outlet passageway 148 is in fluid communication with the administration set 82 of the invention via passageway 151, the rate of fluid flow toward the patient can be precisely controlled by selecting a rate control passageway of appropriate length that is formed in rate control plate 110.

Turning next to FIGS. 97 through 101, still another form of the dispensing device of the present invention for dispensing medicaments to a patient is there shown and generally designated by the numeral 342. This alternate form of dispensing device is similar in many respects to that shown in FIGS. 88 through 91 and like numerals are used in FIGS. 97 through 101 to identify like components.

Figure 97:
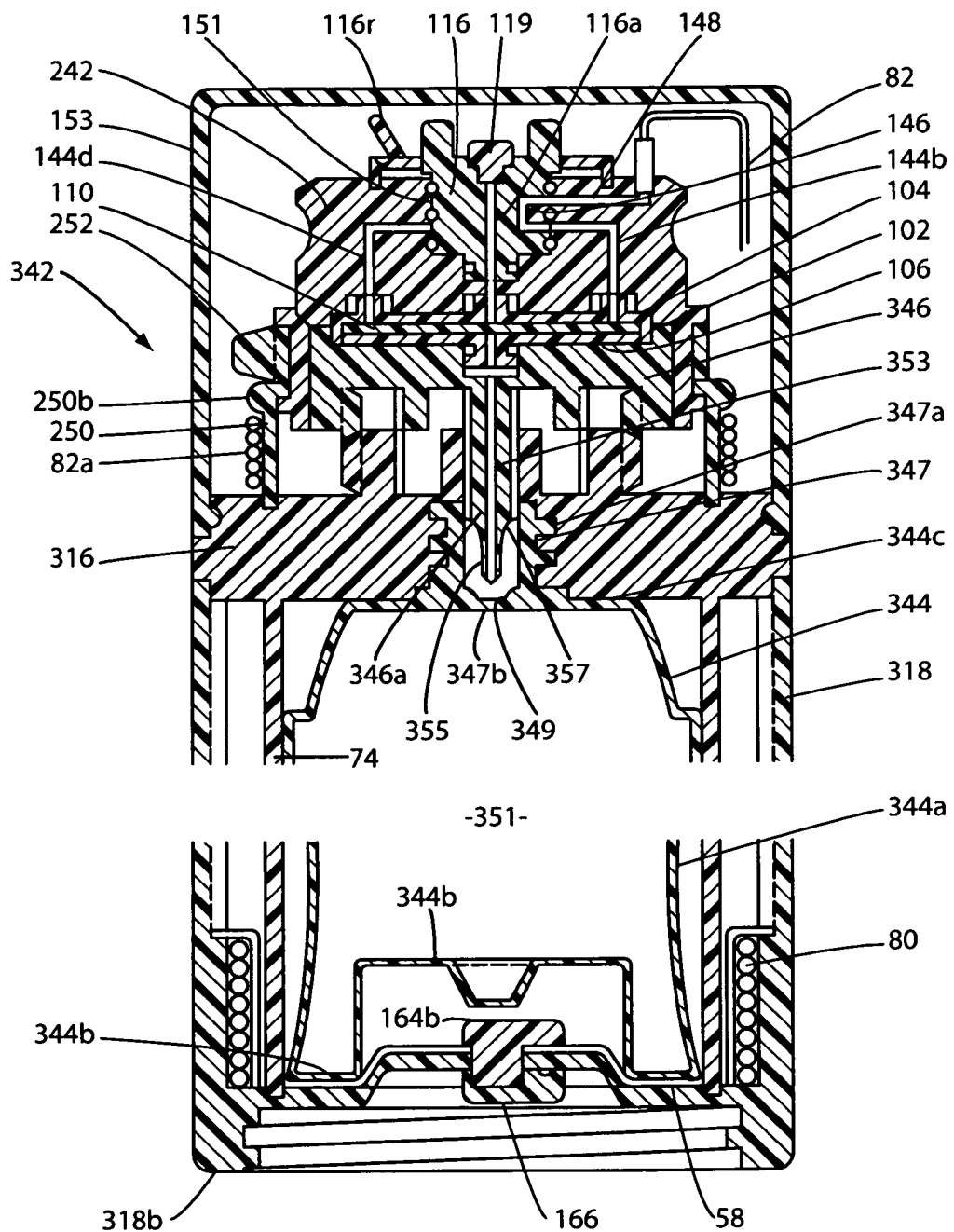
FIG. 97 is a foreshortened, longitudinal, cross-sectional view of another alternate form of the fluid dispensing device of the invention.

The difference between this latest embodiment of the invention and that shown in FIGS. 88 through 91 resides in the slightly differently configured reservoir defining container 344 and the slightly differently configured penetrating assembly 346. As shown in FIG. 97 container 344 is similar in most respects to container 322 of FIG. 88 save that the a Luer-like connector 347 has external threads 347a and is provided with a differently configured sealing wall 349 for sealably engaging the slightly differently configured penetrating member 346a of penetrating assembly 346.

Figure 98:
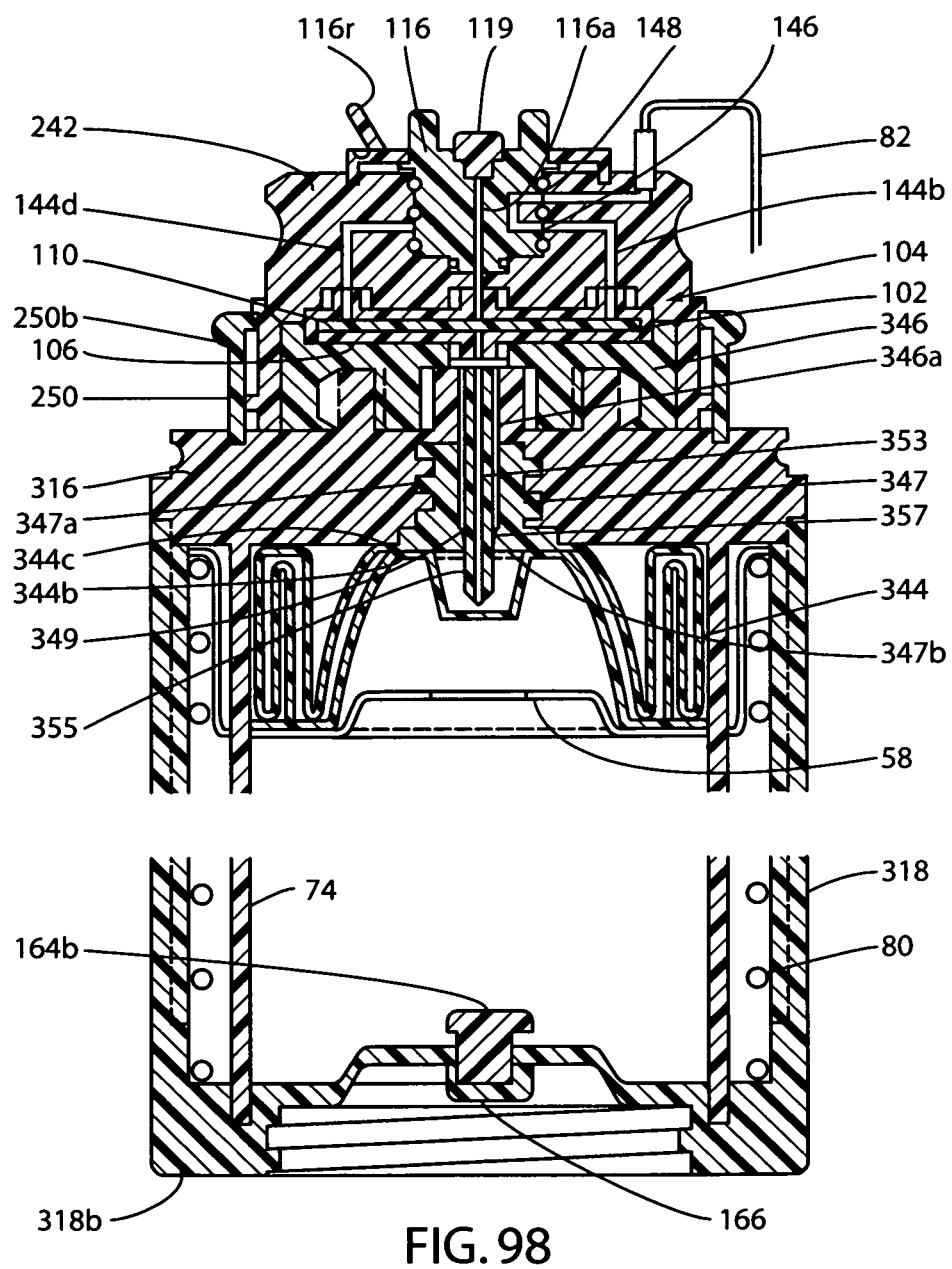
FIG. 98 is a foreshortened longitudinal, cross-sectional view similar to FIG. 97, but showing the various components of the device as they appear following delivery to the patient of the fluid contained within the device reservoir.

Reservoir defining container 344 has sidewall 344a that is movable from the expanded, starting configuration shown in FIG. 97 to the collapsed configuration shown in FIG. 98. This important reservoir defining container here includes, in addition to sidewall 344a, an interconnected bottom wall 344b, an interconnected top wall 344c to which Luer-like connector 347 is attached. Luer-like connector 347 here forms a part of the novel reservoir access means of the invention.

Collapsible unitary container 344 defines a fluid reservoir 351 that is accessible via penetrating member 346a. Penetrating member 346a here comprises an elongated body portion 353 and a reduced diameter penetrating portion 355 that is adapted to pierce closure wall 347b of Luer-like connector 347 in the manner shown in FIG. 98. After penetrating portion 355 pierces closure wall 347b, the tapered interconnection wall 357, which interconnects body portion 353 and reduced diameter penetrating portion 355, sealably engages sealing wall 349 in the manner shown in FIG. 98.

Except for the differently configured collapsible container 344 and the differently configured penetrating member 346a, the apparatus of this latest form of the invention, including the carriage assembly 58, the locking means, the stored energy source and a flow control means operate in the same manner to accomplish the same result as the apparatus discussed in connection with FIGS. 88 through 91.

Turning next to FIGS. 102 through 106, still another form of the dispensing device of the present invention for dispensing medicaments to a patient is there shown and generally designated by the numeral 362. This alternate form of dispensing device is similar in many respects to that shown in FIGS. 97 through 101 and like numerals are used in FIGS. 102 through 106 to identify like components.

Figure 102:
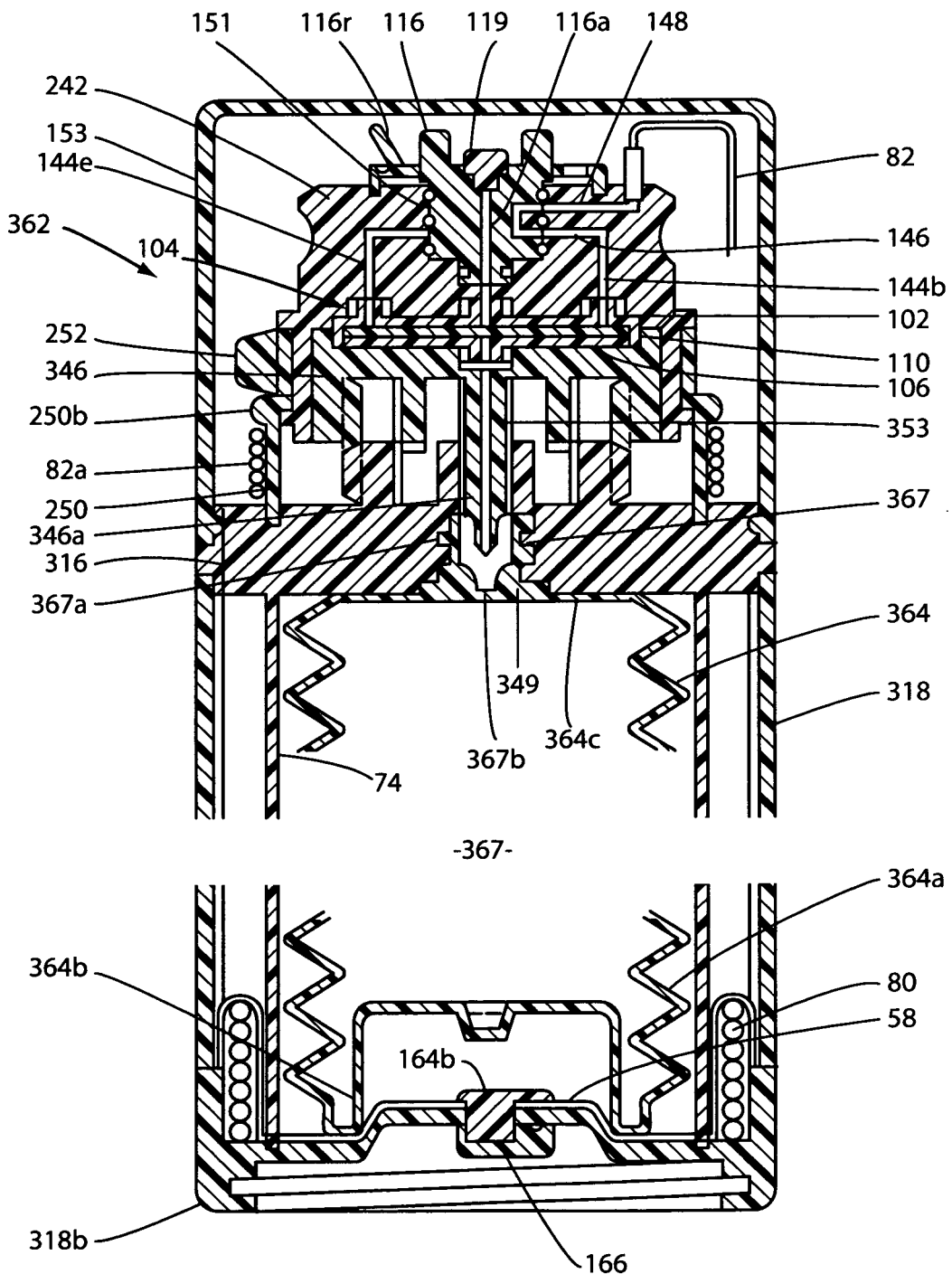
FIG. 102 is a foreshortened, longitudinal, cross-sectional view of yet another alternate form of the fluid dispensing device of the invention.
Figure 103:
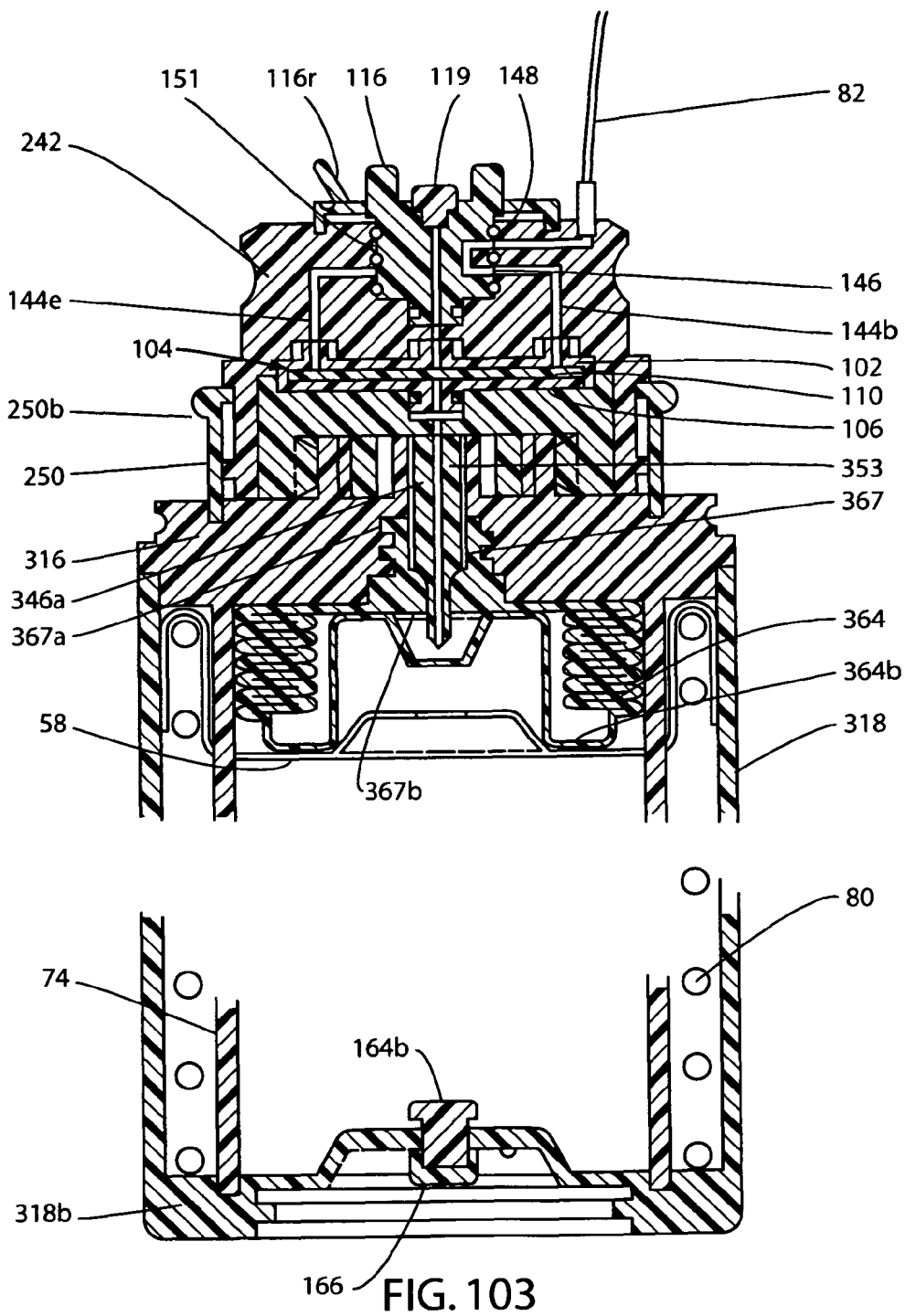
FIG. 103 is a foreshortened longitudinal, cross-sectional view similar to FIG. 102, but showing the various components of the device as they appear following delivery to the patient of the fluid contained within the device reservoir.

The difference between this latest embodiment of the invention and that shown in FIGS. 97 through 101 resides only in the differently configured reservoir defining container 364. As shown in FIG. 102 container 364, rather than being in the nature of the collapsible bottle, comprises a reservoir defining container having a bellows-like sidewall 364a that is movable from the expanded, starting configuration shown in FIG. 102 to the collapsed configuration shown in FIG. 103. This important reservoir defining container here includes, in addition to sidewall 364a, an interconnected bottom wall 364b, and an interconnected top wall 364c.

Connected to top wall 364c and extending therefrom, is a Luer-like connector 367 having external threads 367a and a sealing wall 367b. Connector 367, which is interconnected with top wall 364c at the time of manufacture of the collapsible container assembly 364, here forms a part of the novel reservoir access means of the invention.

Collapsible unitary container 364 defines a fluid reservoir 367 that is accessible via a penetrating member 346a that is identical to the penetrating member previously described in connection with FIGS. 97 and 98 and is adapted to pierce closure wall 367b in the manner previously described.

Except for the differently configured collapsible container 364, the apparatus of this latest form of the invention, including the carriage assembly 58, the locking means, the stored energy source and a flow control means operate in the same manner to accomplish the same result as the apparatus discussed in connection with FIGS. 97 through 101.

Referring now to FIGS. 107 through 111, yet another form of the dispensing device of the present invention for dispensing medicaments to a patient is there shown and generally designated by the numeral 372. This alternate form of dispensing device is similar in many respects to that shown in FIGS. 97 through 101 and like numerals are used in FIGS. 107 through 111 to identify like components.

Figure 107:
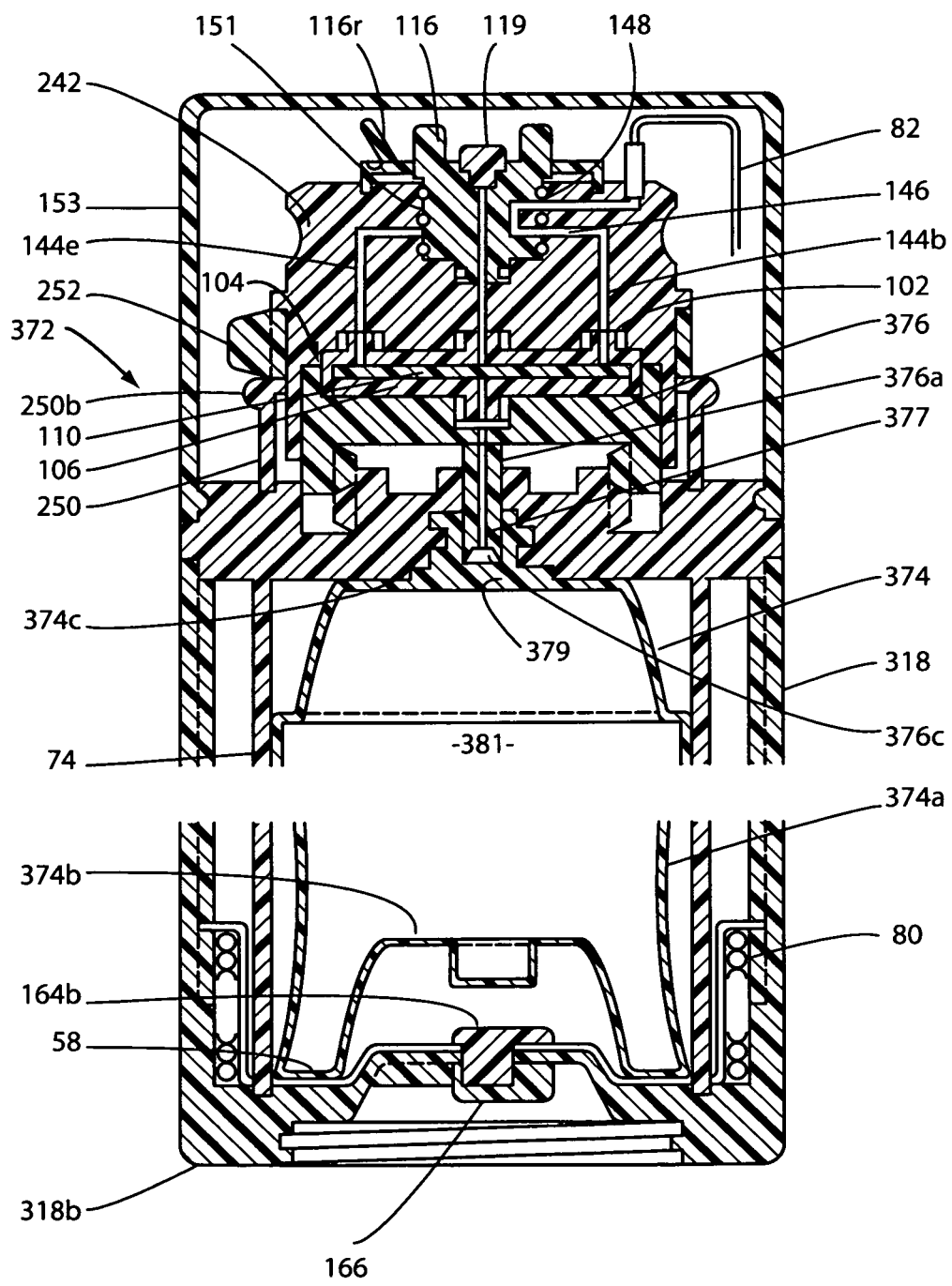
FIG. 107 is a foreshortened, longitudinal, cross-sectional view of still another alternate form of the fluid dispensing device of the invention.

The difference between this latest embodiment of the invention and that shown in FIGS. 97 through 101 resides in the slightly differently configured reservoir defining unitary container 374 and the slightly differently configured penetrating assembly 376. As shown in FIG. 107 container 374 is similar in most respects to container 344 of FIG. 97, save that a Luer-like connector 377 is provided with a differently configured sealing wall 379 for sealably engaging the slightly differently configured penetrating member 376a of penetrating assembly 376. Luer-like connector 377 here forms a part of the novel reservoir access means of the invention.

Figure 108:
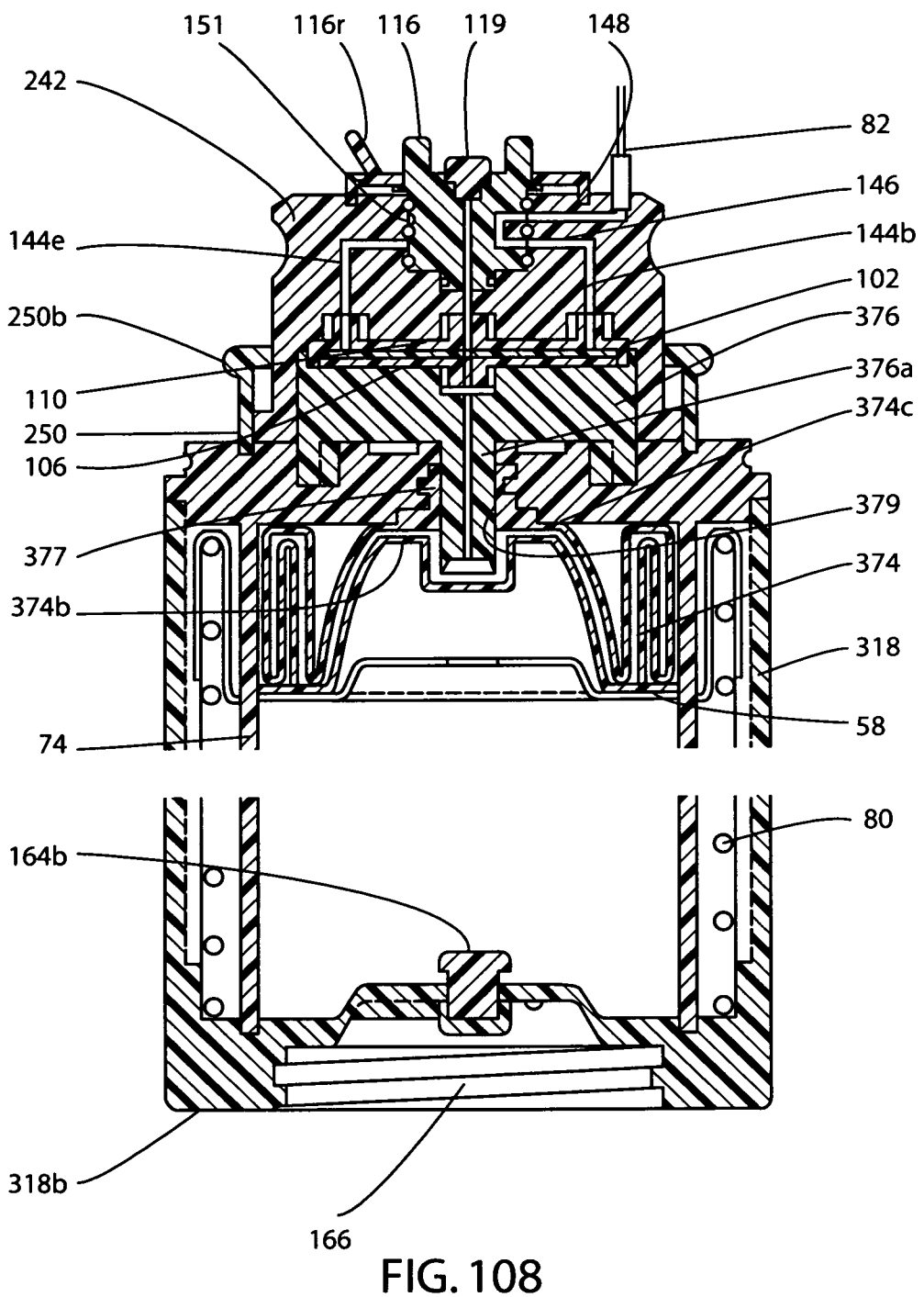
FIG. 108 is a foreshortened longitudinal, cross-sectional view similar to FIG. 107, but showing the various components of the device as they appear following delivery to the patient of the fluid contained within the device reservoir.

Reservoir defining container 374 has sidewall 374a that is movable from the expanded, starting configuration shown in FIG. 107 to the collapsed configuration shown in FIG. 108. This important reservoir defining container here includes, in addition to sidewall 374a, an interconnected bottom wall 374b, an interconnected top wall 374c to which Luer-like connector 377 is attached.

Collapsible container 374 defines a fluid reservoir 381 that is accessible via a punch like penetrating member 376a. Penetrating member 376a here, rather than comprising an elongated body portion and a reduced diameter penetrating portion, comprises a uniform diameter, blunt ended member having an annular cutting element 376c that is adapted to pierce closure wall 379 of Luer-like connector 377 in the manner shown in FIG. 108. After penetrating closure wall 379, portion 376a, sealably engages sealing wall 379 in the manner shown in FIG. 108.

Except for the differently configured collapsible container 374 and the differently configured penetrating assembly 376, the apparatus of this latest form of the invention, including the carriage assembly 58, the locking means, the stored energy source and a flow control means operate in the same manner to accomplish the same result as the apparatus discussed in connection with FIGS. 97 through 101.

Turning next to FIGS. 112 through 116, still another form of the dispensing device of the present invention for dispensing medicaments to a patient is there shown and generally designated by the numeral 382. This alternate form of dispensing device is similar in most respects to that shown in FIGS. 107 through 111 and like numerals are used in FIGS. 112 through 116 to identify like components.

Figure 112:
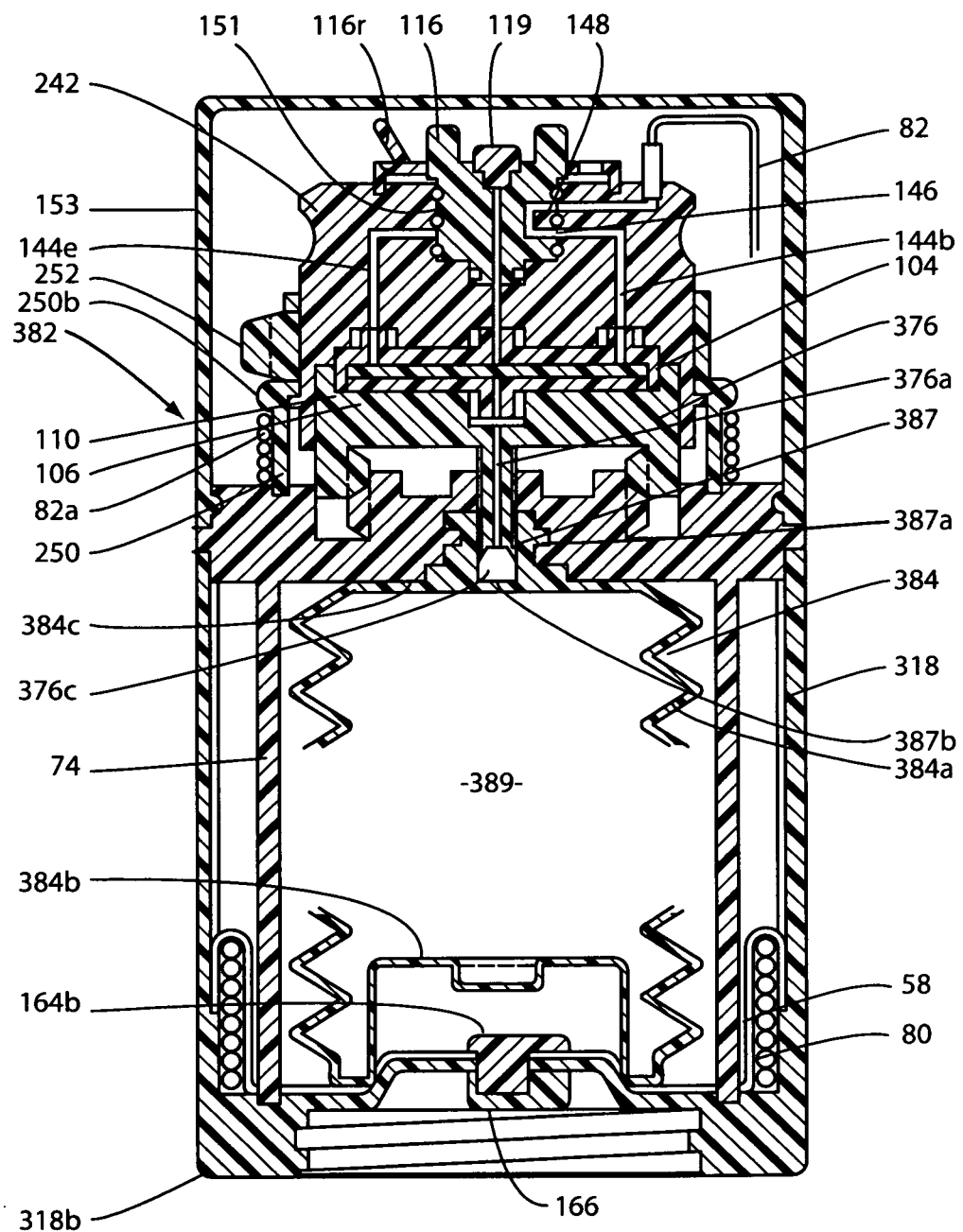
FIG. 112 is a foreshortened, longitudinal, cross-sectional view of yet another alternate form of the fluid dispensing device of the invention.
Figure 113:
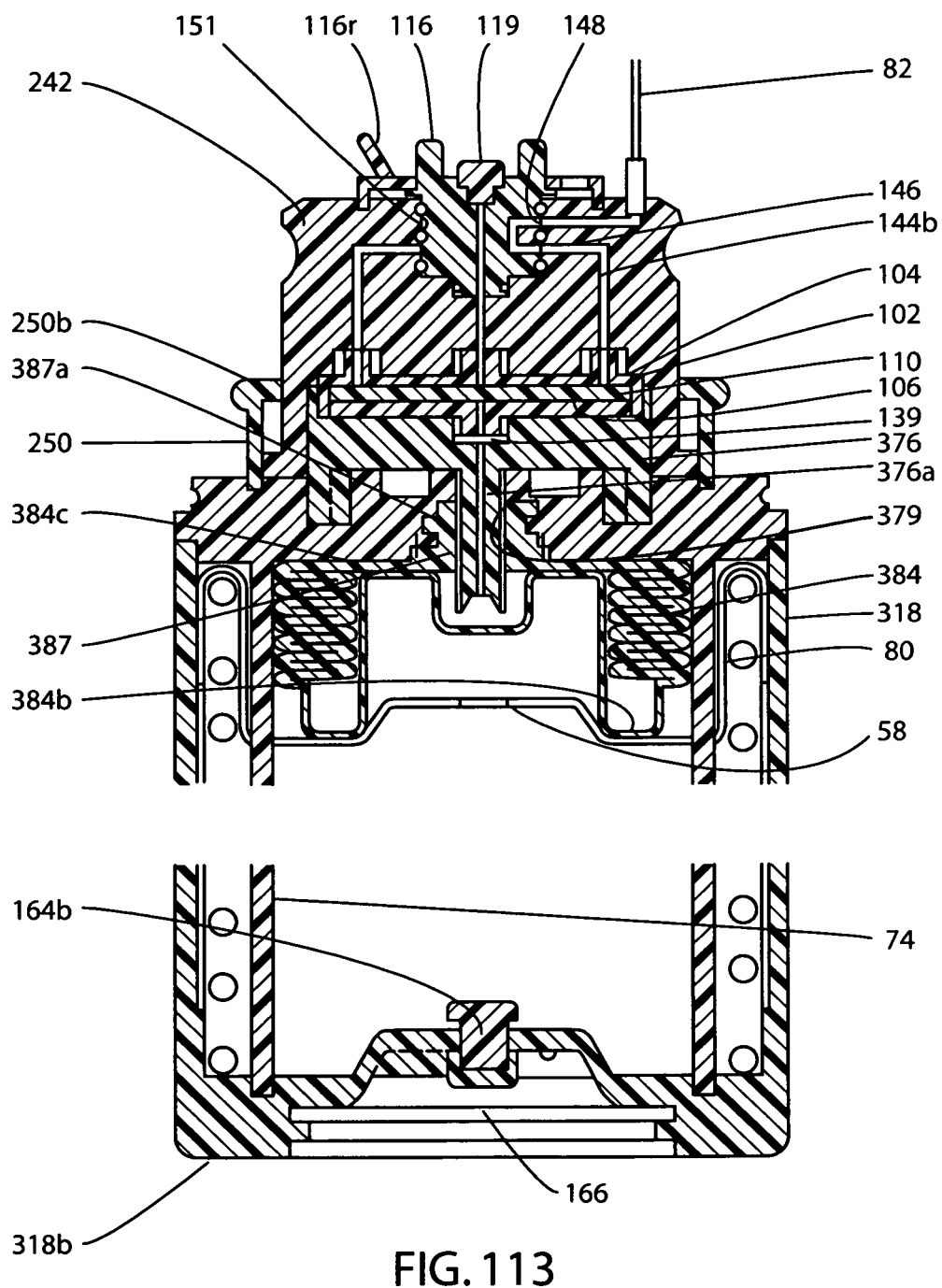
FIG. 113 is a foreshortened longitudinal, cross-sectional view similar to FIG. 112, but showing the various components of the device as they appear following delivery to the patient of the fluid contained within the device reservoir.

The difference between this latest embodiment of the invention and that shown in FIGS. 107 through 111 resides only in the differently configured reservoir defining unitary container 384. As shown in FIG. 112 container 384, rather than being in the nature of the collapsible bottle, comprises a reservoir defining container having a bellows-like sidewall 384a that is movable from the expanded, starting configuration shown in FIG. 112 to the collapsed configuration shown in FIG. 113. This important reservoir defining container here includes, in addition to sidewall 384a, an interconnected bottom wall 384b, and an interconnected top wall 384c.

Connected to top wall 384c and extending therefrom, is a Luer-like connector 387 having external threads 387a and a sealing wall 387b. Connector 387, which is interconnected with top wall 384c at the time of manufacture of the collapsible container assembly 384, here forms a part of the novel reservoir access means of the invention.

Collapsible container 384 defines a fluid reservoir 389 that is accessible via a penetrating member 376a that is identical to the penetrating member previously described in connection with FIGS. 107 and 108 and is adapted to pierce closure wall 387b in the manner previously described.

Except for the differently configured collapsible container 384, the apparatus of this latest form of the invention, including the carriage assembly 58, the locking means, the stored energy source and a flow control means operate in the same manner to accomplish the same result as the apparatus discussed in connection with FIGS. 107 through 111.

Referring next to FIGS. 117 through 122, still another form of the dispensing device of the present invention for dispensing medicaments to a patient is there shown and generally designated by the numeral 392. This alternate form of dispensing device is similar in some respects to the earlier described embodiments shown in FIGS. 77 through 82 and like numerals are used in FIGS. 117 through 122 to identify like components.

The primary difference between this latest form of dispensing device and that previously described in connection with FIGS. 77 through 82 resides in the provision of a novel stored energy source, which is of a totally different construction. More particularly, rather than being in the form of a coil spring, the novel stored energy means of this latest form of the invention comprises a compressible, expandable sponge-like configuration, which is generally designated in the drawings by the numeral 394. This unique stored energy source, which functions to move a carriage 396 from the first compressed position shown in FIG. 117 to the second expanded position shown in FIG. 118 can take several forms. By way of non-limiting example, stored energy source 394 can comprise a micro porous, malodorous, macro-porous, ordered structure and can be constructed from Polypropylene (PP), Ultra High Molecular Weight Polyethylene (UHMWPE), High Density Polyethylene (HDPE), Polyvinylidene Fluoride (PVDF), Ethyle-vinyl Acetate (EVA), Styrene Acrylonitrile (SAN), Polytetrafluroethylene (PTFE) and porous cellulose acetate. A suitable source of these materials is Porex Technologies of Fairburn, Ga. However, practice has shown that any porous plastic material including an open cell, porous sponge material is suitable for use in constructing the stored energy source.

Figure 117:
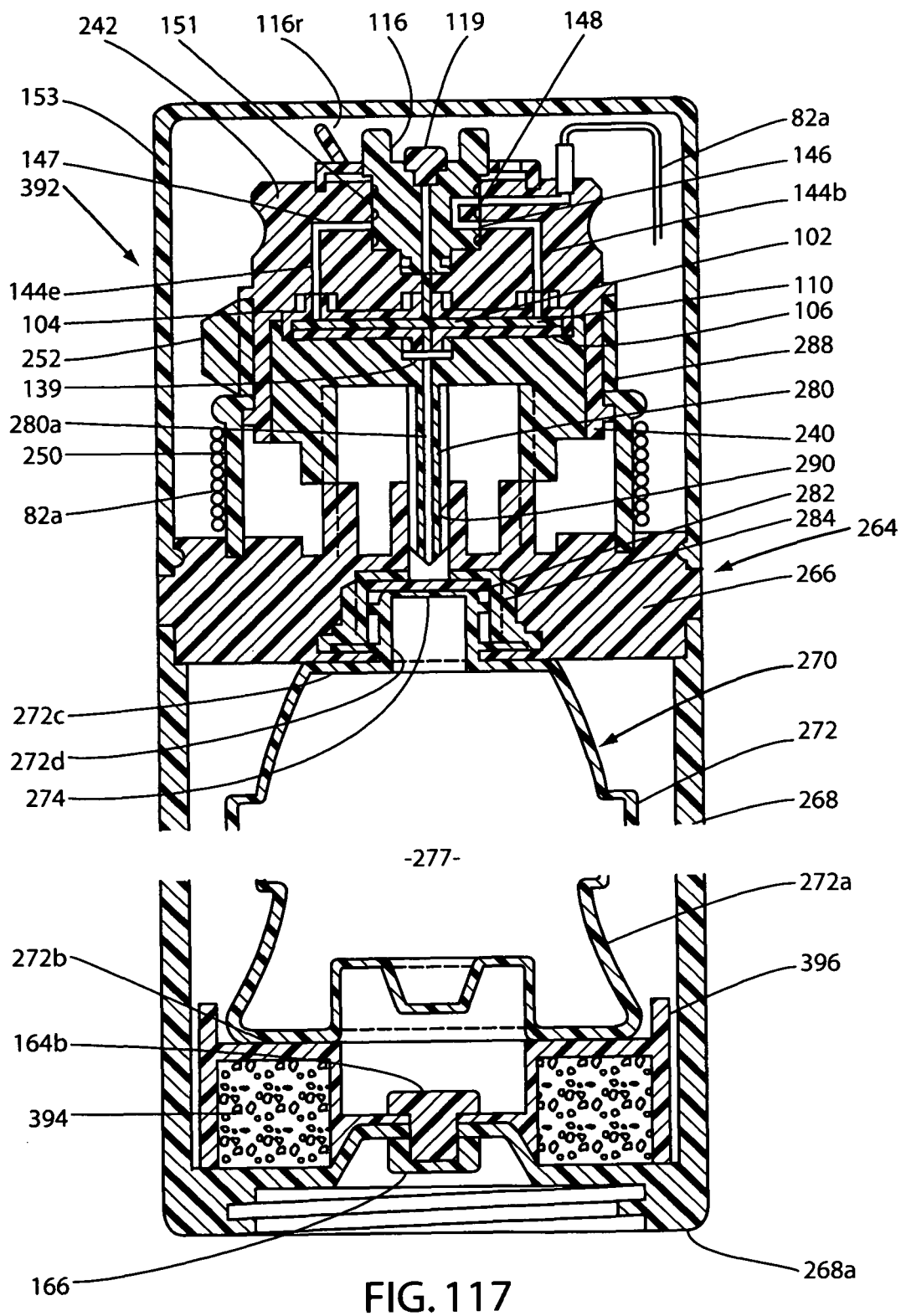

As in the embodiment of the invention shown in FIG. 77, the reservoir defining assembly 270 here comprises a collapsible container assembly 272, which is of identical construction that previously described and is carried by carriage assembly 396 in the manner illustrated in FIG. 117.

As before, the carriage assembly 396 is releasably secured to base portion 268a of the outer housing 268 by a novel locking means. When the locking means of the invention is manipulated in a manner to unlock the carriage assembly 396 from the base portion 268a, sponge 394 will expand from the first compressed position shown in FIG. 117 to the second expanded position shown in FIG. 118 and in so doing will controllably move the carriage assembly from its starting position shown in FIG. 117 to its more fully deployed or extended position shown in FIG. 118. As the carriage assembly moves toward its deployed position, the sidewall 272a of the collapsible container 272 will move into the collapsed configuration shown in FIG. 118. As the collapsible container collapses, the medicinal fluid contained within the container reservoir 277 will be controllably urged outwardly thereof.

To control the flow of medicinal fluid from reservoir 277 toward the administration set 82 of the invention and then on to the patient, flow control means are provided. Once again, this novel fluid flow control means, comprises two cooperating components, namely a rate control means for controlling the rate of fluid flow from the collapsible reservoir and an operating means for controlling fluid flow between the collapsible reservoir and the rate control means. Both the operating means and the rate control means of this latest form of the invention are identical in construction and operation to those described in connection with the embodiment of FIGS. 77 through 82.

As in the earlier described embodiment, the selector member housing 242 is retained in its first position by a tear strip 252. When the tear strip is removed, a rotary force exerted on selector member housing 242 will move the housing along with the penetrating assembly 288 into the second position shown in FIG. 118 and in so doing will cause the penetrating member 280 to pierce the membrane 282 as well as the closure wall 274 in the manner shown in FIG. 118. Piercing of the membrane 282 and the closure wall 274 opens a fluid communication path from reservoir 277 to the rate control assembly 104 via a central fluid passageway 280a formed in penetrating member 280. From reservoir 277, the fluid will flow through central fluid passageway 280a of penetrating member 280, through conventional particulate filter 139, through the rate control assembly 104, through the selector member 116 and toward the patient via the administration set 82.

Referring next to FIGS. 123 through 127, yet another form of the dispensing device of the present invention for dispensing medicaments to a patient is there shown and generally designated by the numeral 402. This alternate form of dispensing apparatus is similar in most respects to that shown in FIGS. 117 through 122 and like numerals are used in FIGS. 123 through 127 to identify like components. The major difference between this latest embodiment of the invention and that shown in FIGS. 117 through 122 resides in the differently configured reservoir defining container 404.

Figure 123:
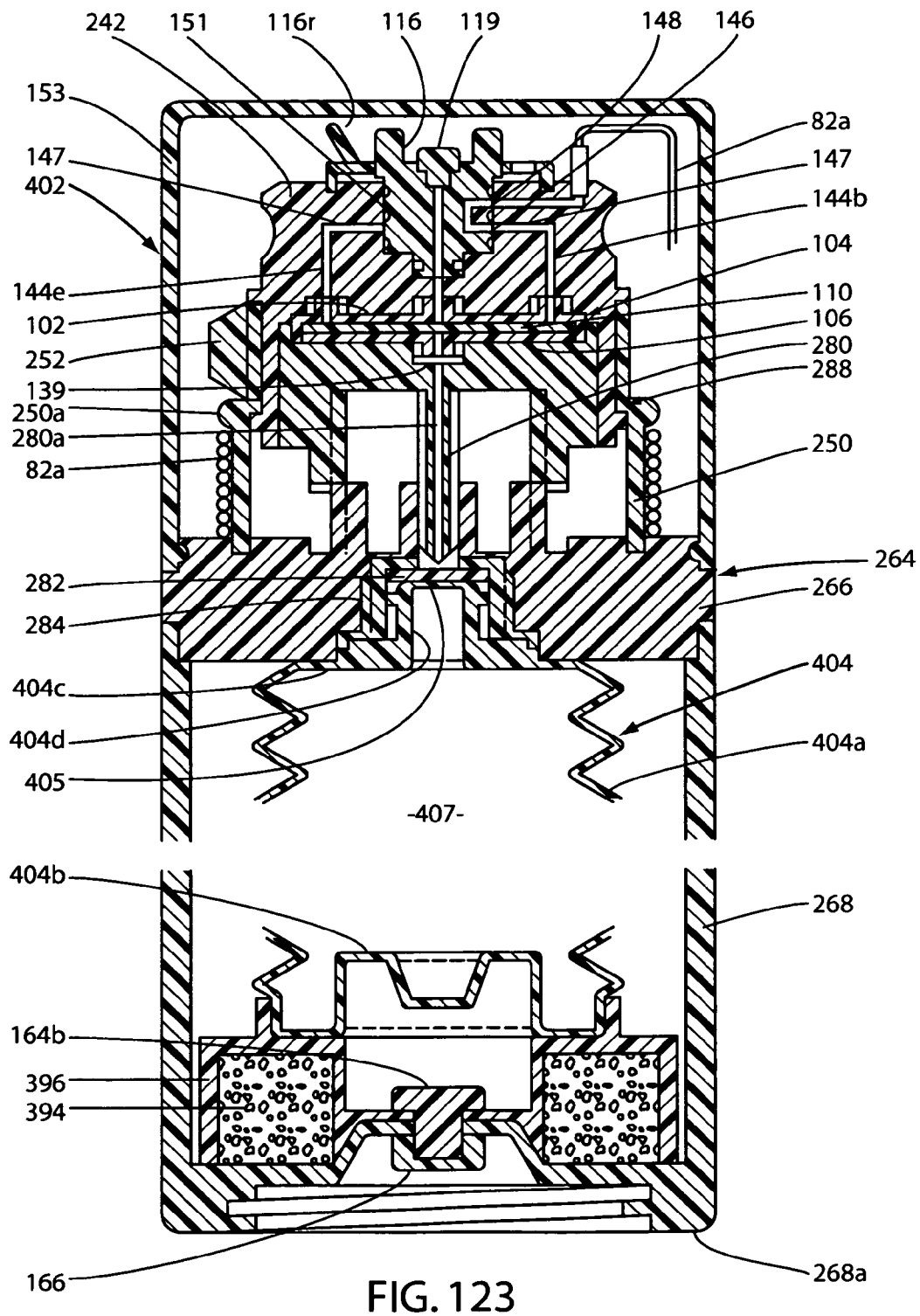
Figure 124:
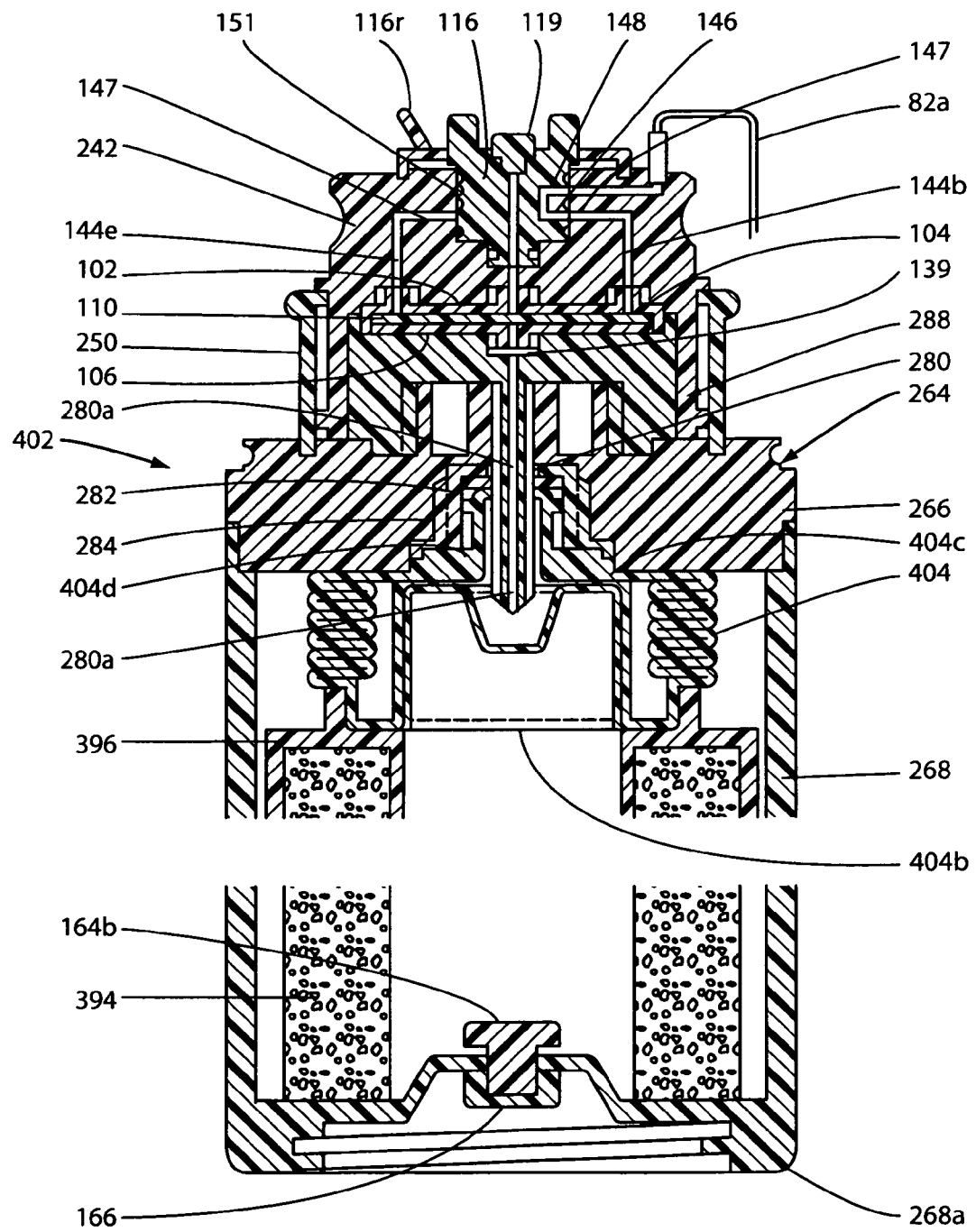

As shown in FIGS. 123 and 126, container 404, rather than being in the nature of a collapsible bottle, comprises a reservoir defining container having a bellows-like sidewall 404a that is movable from the expanded, starting configuration shown in FIG. 123 to the collapsed configuration shown in FIG. 124. This important reservoir defining container here includes, in addition to sidewall 404a, an interconnected bottom wall 404b, an interconnected top wall 404c and an interconnected neck portion 404d, which is sealed at the time of manufacture by a thin closure wall 405. Neck portion 404d forms a part of the novel reservoir access means of the invention. Collapsible container 404 defines a fluid reservoir 407 that is accessible via a penetrating member 280 that is identical to that previously described. Penetrating member 280 is adapted to pierce closure wall 405 as well as a pierceable membrane 282, which is positioned over closure wall 405 of by means of a closure cap 284, which is affixed to the neck portion 404d of container assembly 404.

As best seen in FIGS. 123 and 124 the supporting structure is substantially identical to the supporting structure of the last described embodiment and here comprises a connector assembly 266 and a generally cylindrically shaped outer housing 268 that is interconnected with the connector assembly in the manner best seen in FIG. 123 of the drawings.

Disposed within outer housing 268 is the carriage assembly 396, which is of identical construction and operation to that previously described and is releasably locked in its first position by locking means also identical in construction and operation to the locking means previously described herein.

Carried by carriage assembly is the previously described reservoir defining container 404.

As in the last described embodiment of the invention, closure wall 405 is sealably interconnected with neck portion 404*d* in accordance with the previously described aseptic blow-fill-seal technique. As before, the basic container 404 is formed using the earlier described aseptic blow-fill-seal technique and the reservoir portion of the container is sealed by the thin closure wall 405. The piercable membrane 282 is then positioned over the closure wall 405 and the cap 284 is positioned over the piercable membrane and secured to neck portion 404*d* by any suitable means such as adhesive bonding or sonic welding.

Once again, in order to controllably move the carriage assembly from its first position to its second position, novel stored energy means are provided. This novel stored energy means, which is operably associated with carriage assembly 396, is here provided in the form of a compressible, expandable sponge-like configuration 394, which is identical in construction and operation to that previously described.

As in the earlier described embodiments of the invention, when the locking means of the invention is manipulated in a manner to unlock the carriage assembly from base portion 268*a* of the outer housing 268, sponge 394 will expand and in so doing will controllably move the carriage assembly from its starting position shown in FIG. 123 to its fully deployed or extended position shown in FIG. 124. As the carriage assembly moves toward its deployed position, the sidewall 404*a* of the collapsible container 404 will move into the collapsed configuration shown in FIG. 124. As the collapsible container collapses, the medicinal fluid contained within the container will be controllably expelled therefrom.

To control the flow of medicinal fluid from reservoir 407 toward the administration set 82 of the invention and then on to the patient, flow control means are provided. Once again, this novel fluid flow control means, comprises two cooperating components, namely a rate control means for controlling the rate of fluid flow from the collapsible reservoir and an operating means for controlling fluid flow between the collapsible reservoir and the rate control means. Both the operating means and the rate control means of this latest form of the invention are identical in construction and operation to those described in connection with the embodiment of FIGS. 117 and 118.

As in the earlier described embodiment, selector member housing 242 is retained in its first position by a tear strip 252. When the tear strip is removed, a rotary force exerted on selector member housing 242 will move the housing along with the penetrating assembly into the second position shown in FIG. 124 and in so doing will cause the penetrating member 280 to pierce the membrane 282 as well as the closure wall 405 in the manner shown in FIG. 124. Piercing of the membrane 282 and the closure wall 405 opens a fluid communication path from reservoir 407 to the rate control assembly 104 via a central fluid passageway 280*a* formed in penetrating member 280. From reservoir 407, the fluid will flow through central fluid passageway 280*a* of penetrating member 280, through conventional particulate filter 139, through the rate control assembly 104, through the selector member 116 and toward the patient via the administration set 82.

Turning next to FIGS. 128 through 132, yet another form of the dispensing device of the present invention for dispensing medicaments to a patient is there shown and generally designated by the numeral 412. This alternate form of dispensing apparatus is similar in many respects to that shown in FIGS. 123 through 126 and like numerals are used in FIGS. 128 through 132 to identify like components. As best seen in FIGS. 128 and 129 the supporting structure 414 is similar in many respects to supporting structure 264 of FIGS. 123 and 124 and here comprises a connector assembly 416 and a generally cylindrically shaped outer housing 418 that is interconnected with the connector assembly in the manner best seen in FIG. 128 of the drawings.

Disposed within outer housing 418 is the carriage assembly 396, which is of identical construction and operation to that described in connection with the preceding embodiment and is releasably locked in its first position by locking means also identical in construction and operation to the locking means previously described herein. Carried by carriage assembly 396 is a reservoir defining assembly 420, which is of a somewhat different construction. This important reservoir defining assembly here includes a collapsible container assembly 420 having a sidewall 420*a*, an interconnected bottom wall 420*b* and an interconnected top wall 420*c*. Connected to top wall 420*c* and extending therefrom, is a Luer-like connector 422 having external threads 422*a* and a sealing wall 422*b*. Connector 422, which is interconnected with top wall 420*c* at the time of manufacture of the collapsible container assembly, forms a part of the novel reservoir access means of this latest form of the invention. Collapsible container assembly 420 defines a fluid reservoir 425 that is accessible via a penetrating member 280 that is identical to that previously described and is adapted to pierce the closure wall 422*c* of Luer-like connector 422 and sealably engage a sealing wall 422*b* formed on connector 422.

In the preferred form of this latest alternate embodiment of the invention, Luer-like connector 422 is integrally formed and sealably interconnected with top wall 420*c* in accordance with the previously described aseptic blow-fill-seal technique. In order to controllably move the carriage assembly from its first position to its second position, novel stored energy means are provided. This novel stored energy means, which is operably associated with carriage assembly 396, is here provided in the form of a compressible, expandable sponge-like configuration 394, which is identical in construction and operation to that previously described.

As in the earlier described embodiments of the invention, when the locking means of the invention is manipulated in a manner to unlock the carriage assembly from base portion 418*a* of the outer housing 418, sponge 394 will expand from its first compressed position shown in FIG. 128 to its second, more expanded position shown in FIG. 129 and in so doing will controllably move the carriage assembly from its starting position shown in FIG. 128 to its fully deployed or extended position shown in FIG. 129. As the carriage assembly moves toward its deployed position, the collapsible sidewall 420*a* of the collapsible container 420 will move into the collapsed configuration shown in FIG. 129. As the container collapses, the medicinal fluid contained within the container will be controllably expelled therefrom.

To further control the flow of medicinal fluid from reservoir 425 toward the administration set 82 of the invention and then on to the patient, flow control means are provided. These important flow control means are identical to those previously described in connection with the embodiment of FIGS. 122 and 123 and will not here be further discussed.

As in the last described embodiment, selector member housing 242 is retained in its first position by a tear strip 252. When the tear strip 252 is removed, a rotary force exerted on selector member housing 242 will move the housing along with the penetrating assembly 288 into the second position shown in FIG. 129 and in so doing will cause the penetrating member 280 to penetrate top wall 422*c* of the Luer-like connector 422.

Piercing of wall 422c opens a fluid communication path from reservoir 425 to the rate control assembly 104 via a central fluid passageway 280a formed in penetrating member 280. From passageway 280a, fluid will flow through conventional particulate filter 139, into the inlet of the rate of control assembly 104 and into the circumferentially spaced-apart fluid passageways formed in the selector housing 242. In operating the device in the manner previously described herein, by rotating the selector member 116, which is carried by selector member housing 242, the rate of fluid flow toward the patient can be precisely controlled by selecting a rate control passageway of appropriate length, width and geometry that is formed in rate control plate 110.

Turning next to FIGS. 133 and 134, yet another form of the dispensing device of the present invention for dispensing medicaments to a patient is there shown and generally designated by the numeral 422. This alternate form of dispensing apparatus is similar in many respects to that shown in FIGS. 128 through 132 and like numerals are used in FIGS. 133 and 134 to identify like components. The major difference between this latest embodiment of the invention and that shown in FIGS. 128 through 132 resides in the differently configured reservoir defining container 424.

As shown in FIGS. 133 and 134, container 424, rather than being in the nature of the collapsible bottle, comprises a reservoir defining container having a bellows-like sidewall 424a that is movable from the expanded, starting configuration shown in FIG. 133 to the collapsed configuration shown in FIG. 134. This important reservoir defining container here includes, in addition to sidewall 424a, an interconnected bottom wall 424b, an interconnected top wall 424c and an interconnected neck portion 424d, which is integrally formed and sealed at the time of manufacture by a thin closure wall 425. Neck portion 424d forms a part of the novel reservoir access means of the invention. Collapsible container 424 defines a fluid reservoir 427 that is accessible via a penetrating member 280 that is identical to that previously described. Penetrating member 280 is adapted to pierce closure wall 425 in the manner shown in FIG. 134.

The supporting structure 414 is substantially identical to the supporting structure of the last described embodiment and here comprises a connector assembly 416 and a generally cylindrically shaped outer housing 418 that is interconnected with the connector assembly in the manner best seen in FIG. 133 of the drawings.

Disposed within outer housing 418 is the carriage assembly 396, which is of identical construction and operation to that previously described and is releasably locked in its first position by locking means also identical in construction and operation to the locking means previously described herein. Carried by carriage assembly is the previously described reservoir defining container 424.

As in the last described embodiment of the invention, closure wall 425 is sealably interconnected with neck portion 424d in accordance with the previously described aseptic blow-fill-seal technique. Once again, in order to controllably move the carriage assembly from its first position to its second position, novel stored energy means are provided. This novel stored energy means, which is operably associated with carriage assembly 396, is here provided in the form of a compressible, expandable sponge-like configuration 394, which is identical in construction and operation to that previously described.

As in the earlier described embodiments of the invention, when the locking means of the invention is manipulated in a manner to unlock the carriage assembly from base portion 418a of the outer housing 418, sponge 394 will expand and in so doing will controllably move the carriage assembly from its starting position shown in FIG. 133 to its fully deployed or extended position shown in FIG. 134. As the carriage assembly moves toward its deployed position, the sidewall 424a of the collapsible container 424 will move into the collapsed configuration shown in FIG. 134. As the collapsible container collapses, the medicinal fluid contained within the container will be controllably expelled therefrom.

To control the flow of medicinal fluid from reservoir 427 toward the administration set 82 of the invention and then on to the patient, flow control means are provided. Once again, this novel fluid flow control means, comprises two cooperating components, namely a rate control means for controlling the rate of fluid flow from the collapsible reservoir and an operating means for controlling fluid flow between the collapsible reservoir and the rate control means. Both the operating means and the rate control means of this latest form of the invention are identical in construction and operation to those described in connection with the embodiment of FIGS. 128 and 129.

As in the earlier described embodiment, selector member housing 242 is retained in its first position by a tear strip 252. When the tear strip is removed, a rotary force exerted on selector member housing 242 will move the housing along with the penetrating assembly into the second position shown in FIG. 134 and in so doing will cause the penetrating member 280 to pierce the closure wall 425 in the manner shown in FIG. 134. Piercing of the closure wall 425 opens a fluid communication path from reservoir 427 to the rate control assembly 104 via a central fluid passageway 280a formed in penetrating member 280. From reservoir 427, the fluid will flow through central fluid passageway 280a of penetrating member 280, through conventional particulate filter 139, through the rate control assembly 104, through the selector member 116 and toward the patient via the administration set 82.

Having now described the invention in detail in accordance with the requirements of the patent statutes, those skilled in this art will have no difficulty in making changes and modifications in the individual parts or their relative assembly in order to meet specific requirements or conditions. Such changes and modifications may be made without departing from the scope and spirit of the invention, as set forth in the following claims.

The invention claimed is:

1. A dispensing device for dispensing medicaments to a patient comprising:
    (a) a supporting structure;
    (b) a pre-filled collapsible container having a continuous wall formed of a single material carried by said supporting structure, said collapsible container comprising an hermetically sealed reservoir, including an accordion-like member, said hermetically sealed reservoir having an outlet port and including sealing means for sealing said outlet port, said sealing means comprising a nipple connected to said accordion-like member, said nipple having a severable tip portion;
    (c) stored energy means carried by said supporting structure and operably associated with said collapsible reservoir for collapsing said collapsible reservoir to expel fluid therefrom;
    (d) an administration set, including an administration line interconnected with said outlet of said collapsible reservoir; and
    (e) fluid flow control means carried by said supporting structure for controlling fluid flow from said collapsible reservoir toward said administration set, said fluid flow control means comprising rate control means carried by said supporting structure for controlling the rate of fluid flow from said collapsible reservoir toward said administration set and operating means carried by said supporting structure for controlling fluid flow between said collapsible container and said rate control means, said operating means comprising an operating shaft rotatably carried by said supporting structure, said operating shaft carrying a knife for severing said tip portion of said nipple.

2. The dispensing device as defined in claim 1 in which said stored energy means comprises an expandable sponge operably interconnected with said collapsible reservoir.

3. A dispensing device for dispensing medicaments to a patient comprising:
   (a) a supporting structure comprising a base assembly and a housing interconnected with said base assembly;
   (b) a carriage assembly interconnected with said supporting structure for movement between a first position and a second position;
   (c) a unitary pre-filled collapsible container comprising a bellows structure and having an uninterrupted wall carried by said carriage assembly, said collapsible container comprising a reservoir having an outlet port and including sealing means for sealing said outlet port, said sealing means comprising a nipple connected to said uninterrupted wall, said nipple having a severable tip portion;
   (d) a stored energy means operably associated with said carriage assembly for moving said carriage assembly between said first and second positions, said stored energy means comprising a spring;
   (e) an administration set, including an administration line interconnected with said outlet port of said collapsible reservoir; and
   (f) fluid flow control means carried by said base assembly of said supporting structure for controlling fluid flow from said collapsible reservoir toward said administration set, said fluid flow control means comprising:
      (i) rate control means carried by said supporting structure for controlling the rate of fluid flow from said collapsible reservoir toward said administration set; and
      (ii) operating means carried by said supporting structure for controlling fluid flow between said collapsible container and said rate control means, said operating means comprising an operating shaft rotatably carried by said base assembly of said supporting structure for movement between a first position blocking fluid flow from said collapsible reservoir toward said administration set and a second position permitting fluid flow from said collapsible reservoir toward said administration set, said operating shaft carrying a knife having a cutting edge for severing said tip portion of said nipple.

4. A dispensing device for dispensing medicaments to a patient comprising:
   (a) a supporting structure comprising a base assembly and a housing interconnected with said base assembly;
   (b) a carriage assembly interconnected with said supporting structure for movement between a first position and a second position;
   (c) a unitary pre-filled collapsible container having an uninterrupted wall carried by said carriage assembly, said collapsible container comprising a reservoir having an outlet port, said uninterrupted wall including an accordion-like member and including sealing means for sealing said outlet port, said sealing means comprising a nipple connected to said accordion-like member, said nipple having a sealed, severable tip portion;
   (d) a stored energy means operably associated with said carriage assembly for moving said carriage assembly between said first and second positions, said stored energy means comprising a spring;
   (e) an administration set, including an administration line interconnected with said outlet port of said collapsible reservoir; and
   (f) fluid flow control means carried by said base assembly of said supporting structure for controlling fluid flow from said collapsible reservoir toward said administration set, said fluid flow control means comprising:
      (i) rate control means carried by said supporting structure for controlling the rate of fluid flow from said collapsible reservoir toward said administration set; and
      (ii) operating means carried by said supporting structure for controlling fluid flow between said collapsible container and said rate control means, said operating means comprising an operating shaft rotatably carried by said base assembly of said supporting structure for movement between a first position blocking fluid flow from said collapsible reservoir toward said administration set and a second position permitting fluid flow from said collapsible reservoir toward said administration set, said operating shaft having a body portion having a cavity located to receive said severable tip portion of said nipple.

5. A dispensing device for dispensing medicaments to a patient comprising:
   (a) a supporting structure comprising a base assembly and a housing interconnected with said base assembly;
   (b) a carriage assembly interconnected with said supporting structure for movement between a first position and a second position;
   (c) a unitary pre-filled collapsible container having an uninterrupted wall carried by said carriage assembly said uninterrupted wall including an accordion-like member, said collapsible container being integrally formed and comprising a reservoir having an outlet port, said outlet port being closed by a frangible member comprising a nipple connected to said accordion-like member, said nipple having a sealed, severable tip portion;
   (d) a stored energy means operably associated with said carriage assembly for moving said carriage assembly between said first and second positions, said stored energy means comprising a spring;
   (e) an administration set, including an administration line interconnected with said outlet port of said collapsible reservoir; and
   (f) fluid flow control means carried by said base assembly of said supporting structure for controlling fluid flow from said collapsible reservoir toward said administration set, said fluid flow control means comprising:
      (i) rate control means carried by said supporting structure for controlling the rate of fluid flow from said collapsible reservoir toward set administration set; and
      (ii) operating means carried by said supporting structure for controlling fluid flow between said collapsible container and said rate control means, said operating means comprising an operating shaft rotatably carried by said base assembly of said supporting structure for movement between a first position blocking fluid flow from said collapsible reservoir toward said administration set and a second position permitting fluid flow from said collapsible reservoir toward said administration set, said operating shaft carrying a spring knife having a cutting edge for severing said tip portion of said nipple.

* * * * *